(12) United States Patent
Kausch-Busies et al.

(10) Patent No.: US 10,765,116 B2
(45) Date of Patent: Sep. 8, 2020

(54) 2-[3-(ALKYLSULFONYL)-2H-INDAZOL-2-YL]-3H-IMIDAZO[4,5-B]PYRIDINE DERIVATIVES AND SIMILAR COMPOUNDS AS PESTICIDES

(71) Applicants: BAYER CROPSCIENCE AKTIENGESELLSCHAFT, Monheim am Rhein (DE); BAYER AKTIENGESELLSCHAFT, Leverkusen (DE)

(72) Inventors: Nina Kausch-Busies, Bergisch Gladbach (DE); Rüdiger Fischer, Pulheim (DE); Laura Hoffmeister, Düsseldorf (DE); David Wilcke, Düsseldorf (DE); Dominik Hager, Monheim (DE); Matthieu Willot, Düsseldorf (DE); Marc Mosrin, Köln (DE); Kerstin Ilg, Köln (DE); Ulrich Görgens, Ratingen (DE); Andreas Turberg, Haan (DE)

(73) Assignees: BAYER CROPSCIENCE AKTIENGESELLSCHAFT, Monheim am Rhein (DE); BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/463,327

(22) PCT Filed: Nov. 22, 2017

(86) PCT No.: PCT/EP2017/080009
§ 371 (c)(1),
(2) Date: May 22, 2019

(87) PCT Pub. No.: WO2018/095953
PCT Pub. Date: May 31, 2018

(65) Prior Publication Data
US 2019/0274306 A1 Sep. 12, 2019

(30) Foreign Application Priority Data
Nov. 23, 2016 (EP) .................... 16200177

(51) Int. Cl.
*C07D 471/04* (2006.01)
*A01N 43/90* (2006.01)
*C07D 519/00* (2006.01)

(52) U.S. Cl.
CPC .......... *A01N 43/90* (2013.01); *C07D 471/04* (2013.01); *C07D 519/00* (2013.01)

(58) Field of Classification Search
CPC ..... C07D 471/04; A01N 43/90; A61K 31/437
(Continued)

(56) References Cited

U.S. PATENT DOCUMENTS 10,188,108 B2 1/2019 Fischer
2018/0022760 A1 1/2018 Kudo
(Continued)

FOREIGN PATENT DOCUMENTS

WO WO2010125985 A1 11/2010
WO WO2012074135 A1 6/2012
(Continued)

OTHER PUBLICATIONS

Fathhalla, O.A. et al.: Synthesis of certain tetrahydroacridine derivatives of anticipated medicinal value. Res. Chem. Intermed., vol. 39, pp. 3487-3505, 2013.*
Abass, M. (2005). "Chemistry of substituted quinolinones. part 8. Synthesis and cyclization reactions of ethyl 5-amino-1-(1-methyl-2-oxoquinolin-4-yl)-3-methylsulfanylpyrazole-4-carboxylate", Chemical Abstracts Service, Columbus, Ohio, US, XP002767322, 4 pages.
Fathalla, O.A. et al. (2012). "Synthyses, reaction and charactrization of quinoline derivatives", International Journal of Pharmacy, 2(2): 299-305.

(Continued)

Primary Examiner — Charanjit Aulakh
(74) Attorney, Agent, or Firm — Morrison & Foerster LLP

(57) ABSTRACT

The invention relates to compounds of the formula (Ia) or (Ib), in which Aa, Ab, Ac, Ad, $R^1$, $R^{10}$ $R^{11}$, $R^{12}$, $R^{13}$, $R^{14}$, $R^{15}$, $R^{16}$, $R^{17}$, Q, R4, $R^5$, $R^6$ and have the meanings indicated in the claims, and to agrochemical formulations containing the compounds according to formula (Ia) or (Ib) for use as acaricides and/or insecticides for combating animal pests, primarily arthropods and in particular insects and arachnids. 2-[3-(alkylsulfonyl)-2H-indazol-2-yl]-3H-imidazo[4,5-b]pyridine derivatives and similar compounds are particularly preferable.

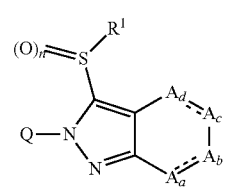

Ia

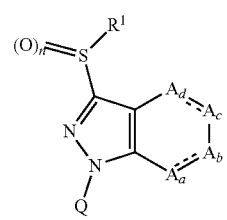

Ib

20 Claims, No Drawings

(58) Field of Classification Search
USPC .......................................... 546/118; 514/303
See application file for complete search history.

(56) References Cited

U.S. PATENT DOCUMENTS

2018/0305353 A1   10/2018   Fischer
2019/0062344 A1   2/2019   Kudo
2019/0248811 A1   8/2019   Fischer

FOREIGN PATENT DOCUMENTS

| WO | WO2016091731 A1 | 6/2016 |
| WO | WO2016107742 A1 | 7/2016 |
| WO | WO2016129684 A1 | 8/2016 |
| WO | WO2016142326 A1 | 9/2016 |
| WO | WO2016142327 A1 | 9/2016 |
| WO | WO2016162318 A1 | 10/2016 |
| WO | WO2017072039 A1 | 5/2017 |
| WO | WO2017093180 A1 | 6/2017 |
| WO | WO2017125340 A1 | 7/2017 |
| WO | WO2017144341 A1 | 8/2017 |
| WO | WO2017155103 A1 | 9/2017 |
| WO | WO2017174414 A1 | 10/2017 |
| WO | WO2018033455 A1 | 2/2018 |

OTHER PUBLICATIONS

International Search Report dated Dec. 18, 2017 for PCT Application No. PCT/EP2017/08009, filed Nov. 22, 2017, 3 pages.

\* cited by examiner

2-[3-(ALKYLSULFONYL)-2H-INDAZOL-2-YL]-3H-IMIDAZO[4,5-B]PYRIDINE DERIVATIVES AND SIMILAR COMPOUNDS AS PESTICIDES

CROSS REFERENCE TO RELATED APPLICATIONS

This application is a national stage application under 35 U.S.C. § 371 of International Application No. PCT/EP2017/080009, filed internationally on Nov. 22, 2017, which claims the benefit of priority to European Application No. 16200177.0, filed Nov. 23, 2016.

The present invention relates to novel fused heterocycle derivatives of the formula (Ia) or (Ib), to agrochemical formulations comprising the compounds of formula (Ia) or (Ib) and to the employment thereof as acaricides and/or insecticides for control of animal pests, particularly of arthropods and especially of insects and arachnids.

Fused bicyclic heterocycle derivatives having insecticidal properties have already been described in the literature, for example in WO 2010/125985, WO 2012/074135, WO 2016/162318, WO 2017/093180, WO 2017/072039, WO 2017/125340, WO 2017/144341, EP 16184163.0, EP 16189445.6, EP 16163912.5, WO 2016/107742, WO 2016/091731, WO 2016/129684, WO 2016/142326, WO 2016/142327 and WO 2017/155103.

Modern insecticides and acaricides have to meet many demands, for example in relation to extent, persistence and spectrum of their action and possible use. Questions of toxicity, sparing of beneficial species and pollinators, environmental properties, application rates, combinability with other active ingredients or formulation auxiliaries play a role, as does the question of the complexity involved in the synthesis of an active ingredient, and resistances can also occur, to mention just a few parameters. For all these reasons alone, the search for novel crop protection compositions cannot be considered complete, and there is a constant need for novel compounds having improved properties compared to the known compounds, at least in relation to individual aspects.

It was an object of the present invention to provide compounds for use for controlling animal pests, which compounds widen the spectrum of the pesticides in various aspects.

Novel fused bicyclic heterocycle derivatives have now been found, these having advantages over the compounds already known, examples of which include better biological or environmental properties, a wider range of application methods, better insecticidal or acaricidal action, and good compatibility with crop plants. The fused bicyclic heterocycle derivatives can be used in combination with further agents for improving efficacy, especially against insects that are difficult to control.

This object, and further objects which are not stated explicitly but can be discerned or derived from the connections discussed herein, are achieved by novel compounds of the formula (Ia) or (Ib)

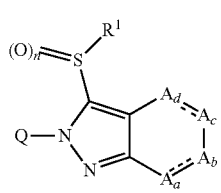

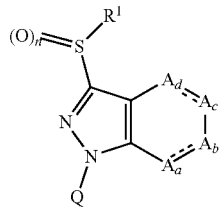

where ⌁ represent single bonds or double bonds,
in which (configuration 1),
if ⌁ represent exclusively double bonds and hence Aa to Ad together with the carbon atoms adjacent to Aa and Ad in each case form an aromatic ring,
Aa is nitrogen or $C(R^{10})$,
Ab is nitrogen or $C(R^{11})$,
Ac is nitrogen or $C(R^{12})$, and
Ad is nitrogen or $C(R^{13})$,
where not more than two of Aa, Ab, Ac and Ad can be nitrogens,
or, if ⌁ represent exclusively single bonds,
Aa is $C(R^{10})(R^{14})$,
Ab is $C(R^{11})(R^{15})$,
Ac is $C(R^{12})(R^{16})$ and
Ad is $C(R^{13})(R^{17})$,
$R^1$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$alkyl, $(C_1-C_6)$alkylsulfinyl-$(C_1-C_6)$alkyl, $(C_1-C_6)$haloalkylsulfinyl-$(C_1-C_6)$alkyl, $(C_1-C_6)$alkylsulfonyl-$(C_1-C_6)$alkyl, $(C_1-C_6)$haloalkylsulfonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulfinyl-$(C_1-C_6)$alkyl, $(C_1-C_6)$alkoxy-$(C_1-C_6)$alkylsulfonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulfonylamino, aminosulfonyl-$(C_1-C_6)$alkyl, $(C_1-C_6)$alkylaminosulfonyl-$(C_1-C_6)$alkyl, di$(C_1-C_6)$alkylaminosulfonyl-$(C_1-C_6)$alkyl, or is in each case singly or multiply, identically or differently aryl-, hetaryl- or heterocyclyl-substituted $(C_1-C_6)$alkyl, $(C_1-C_6)$alkoxy, $(C_2-C_6)$alkenyl, $(C_2-C_6)$alkynyl, $(C_3-C_8)$cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulfinyl, $(C_1-C_6)$alkylsulfonyl, $(C_1-C_6)$alkylsulfimino, $(C_1-C_6)$alkylsulfimino-$(C_1-C_6)$alkyl, $(C_1-C_6)$alkylsulfimino-$(C_2-C_6)$alkylcarbonyl, $(C_1-C_6)$alkylsulfoximino, $(C_1-C_6)$alkylsulfoximino-$(C_1-C_6)$alkyl, $(C_1-C_6)$alkylsulfoximino-$(C_2-C_6)$alkylcarbonyl, $(C_1-C_6)$alkoxycarbonyl, $(C_1-C_6)$alkylcarbonyl, $(C_3-C_6)$trialkylsilyl or benzyl, or $R^1$ is aryl, hetaryl or heterocyclyl, each optionally mono- or polysubstituted identically or differently by halogen, cyano, nitro, hydroxyl, amino, carboxyl, carbamoyl, $(C_1-C_6)$alkyl, $(C_3-C_8)$cycloalkyl, $(C_1-C_6)$-alkoxy, $(C_1-C_6)$haloalkyl, $(C_1-C_6)$haloalkoxy, $(C_1-C_6)$alkylthio, $(C_1-C_6)$alkylsulfinyl, $(C_1-C_6)$alkylsulfonyl, $(C_1-C_6)$alkylsulfimino, $(C_1-C_6)$alkylsulfimino-$(C_1-C_6)$alkyl, $(C_1-C_6)$alkylsulfimino-$(C_2-C_6)$alkylcarbonyl, $(C_1-C_6)$alkylsulfoximino, $(C_1-C_6)$alkylsulfoximino-$(C_1-C_6)$alkyl, $(C_1-C_6)$alkylsulfoximino-$(C_2-C_6)$alkylcarbonyl, $(C_1-C_6)$alkoxycarbonyl, $(C_1-C_6)$alkylcarbonyl, $(C_3-C_6)$trialkylsilyl, $(=O)$ (in the case of heterocyclyl only) or $(=O)_2$ (in the case of heterocyclyl only), $R^{10}$, $R^{11}$, $R^{12}$, $R^{13}$, $R^{14}$, $R^{15}$, $R^{16}$, $R^{17}$ are independently hydrogen, cyano, halogen, nitro, hydroxyl, amino, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di$(C_1-C_6)$alkylaminocarbonyl, di$(C_1-C_6)$alkylaminothiocarbonyl, $(C_2-C_6)$alkenylaminocarbonyl, di$(C_2-C_6)$alkenylaminocarbonyl, $(C_3-C_8)$cycloalkylaminocarbonyl, $(C_1-C_6)$alkylsulfonylamino, $(C_1-C_6)$alkylamino, di$(C_1-C_6)$alkylamino, aminosulfonyl, $(C_1-C_6)$alkylaminosulfonyl, di$(C_1-C_6)$alkylaminosulfonyl, $(C_1-C_6)$alkylsulfoximino, aminothiocarbonyl, $(C_1-C_6)$alkylaminothiocarbonyl, di$(C_1-C_6)$alkylaminothiocarbonyl, $(C_3-C_8)$cycloalkylamino, $(C_1-C_6)$alkylcarbamoyl (including —NHCOO$(C_1-C_6)$alkyl, —N$(C_1-C_6)$alkylCOO$(C_1-C_6)$alkyl, —OCONH$(C_1-C_6)$alkyl or —OCON$(C_1-C_6)$dialkyl), $(C_1-C_6)$alkylcarbonylamino ($(C_1-C_6)$alkylCONH), $(C_1-C_6)$alkylurea (including —NHCONH$(C_1-C_6)$alkyl, and —NHCON$(C_1-C_6)$dialkyl) or is in each case optionally singly or multiply, identically or differently substituted aryl or hetaryl, where (in the case of hetaryl) at least one carbonyl group may optionally be present and where possible substituents in each case are as follows: cyano, carboxyl, halogen, nitro, hydroxyl, amino, tri-$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$alkylcarbonyl-$(C_1-C_6)$alkyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di$(C_1-C_6)$alkylamino, aminosulfonyl, $(C_1-C_6)$alkylaminosulfonyl, di$(C_1-C_6)$alkylaminosulfonyl, $(C_1-C_6)$alkylsulfoximino, aminothiocarbonyl, $(C_1-C_6)$alkylaminothiocarbonyl, di$(C_1-C_6)$alkylaminothiocarbonyl, $(C_3-C_8)$cycloalkylamino or $(C_1-C_6)$alkylcarbonylamino, where only one or two of the $R^{10}$, $R^{11}$, $R^{12}$, $R^{13}$, $R^{14}$, $R^{15}$, $R^{16}$ and $R^{17}$ radicals are a substituent other than hydrogen, and, if any of $R^{10}$ and $R^{14}$, $R^{11}$ and $R^{15}$, $R^{12}$ and $R^{16}$ or $R^{13}$ and $R^{17}$ are both not hydrogen, $R^{14}$, $R^{15}$, $R^{16}$ and $R^{17}$ are each independently only cyano, halogen, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl or $(C_1-C_6)$cyanoalkyl, Q is a partly saturated or saturated heterocyclic or heteroaromatic 8-, 9-, 11- or 12-membered fused bicyclic or tricyclic ring system, where at least one carbonyl group may optionally be present and where the ring system may optionally be mono- or polysubstituted identically or differently, and where the substituents may independently be selected from cyano, halogen, nitro, hydroxyl, amino, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$alkynyloxy-$(C_1-C_4)$alkyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$haloalkoxy-$(C_1-C_6)$alkyl, $(C_2-C_6)$alkenyloxy-$(C_1-C_6)$alkyl, $(C_2-C_6)$haloalkenyloxy-$(C_1-C_6)$alkyl, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$alkylcarbonyl-$(C_1-C_6)$alkyl, $(C_1-C_6)$alkylthiocarbonyl, $(C_1-C_6)$haloalkylcarbonyl, (C₁-C₆)alkylcarbonyloxy, (C₁-C₆)alkoxycarbonyl, (C₁-C₆)haloalkoxycarbonyl, aminocarbonyl, (C₁-C₆)alkylaminocarbonyl, (C₁-C₆)alkylaminothiocarbonyl, di(C₁-C₆)alkylaminocarbonyl, di(C₁-C₆)alkylaminothiocarbonyl, (C₂-C₆)alkenylaminocarbonyl, di(C₂-C₆)alkenylaminocarbonyl, (C₃-C₈)cycloalkylaminocarbonyl, (C₁-C₆)alkylsulfonylamino, (C₁-C₆)alkylamino, di(C₁-C₆)alkylamino, aminosulfonyl, (C₁-C₆)alkylaminosulfonyl, di(C₁-C₆)alkylaminosulfonyl, (C₁-C₆)alkylsulfoximino, aminothiocarbonyl, (C₁-C₆)alkylaminothiocarbonyl, di(C₁-C₆)alkylaminothiocarbonyl, (C₃-C₈)cycloalkylamino or (C₁-C₆)alkylcarbonylamino or where the substituents may independently be selected from phenyl or a 5- or 6-membered heteroaromatic ring, where phenyl or the ring may optionally be mono- or polysubstituted identically or differently by C₁-C₆-alkyl, C₂-C₆-alkenyl, C₂-C₆-alkynyl, C₃-C₆-cycloalkyl, C₁-C₆-haloalkyl, C₂-C₆-haloalkenyl, C₂-C₆-haloalkynyl, C₃-C₆-halocycloalkyl, halogen, CN, C₁-C₄-alkoxy, C₁-C₄-haloalkoxy, n is 0, 1 or 2.

It has additionally been found that the compounds of the formulae (Ia) and (Ib) have very good efficacy as pesticides, preferably as insecticides and/or acaricides, and additionally generally have very good plant compatibility, especially with respect to crop plants.

The compounds according to the invention are defined in general terms by the formulae (Ia) and (Ib). Preferred substituents or ranges of the radicals given in the formulae mentioned above and below are illustrated hereinafter:

Configuration 2

Compounds of the formula I(a) or I(b) in which, preferably, if ⚍ represent exclusively double bonds and hence Aa to Ad together with the carbon atoms adjacent to Aa and Ad in each case form an aromatic ring, Aa is nitrogen or C(R¹⁰),
Ab is nitrogen or C(R¹¹),
Ac is nitrogen or C(R²), and
Ad is nitrogen or C(R¹³),
where not more than two of Aa, Ab, Ac and Ad can be nitrogens, or, if ⚍ represent exclusively single bonds, Aa is C(R¹⁰)(R¹⁴),
Ab is C(R¹¹)(R¹⁵),
Ac is C(R¹²)(R¹⁶) and
Ad is C(R¹³)(R¹¹), R¹ is preferably (C₁-C₄)alkyl, (C₁-C₄)hydroxyalkyl, (C₁-C₄)haloalkyl, (C₁-C₄)cyanoalkyl, (C₁-C₄)alkoxy-(C₁-C₄)alkyl, (C₁-C₄)haloalkoxy-(C₁-C₄)alkyl, (C₂-C₄)alkenyl, (C₂-C₄)alkenyloxy-(C₁-C₄)alkyl, (C₂-C₄)haloalkenyloxy-(C₁-C₄)alkyl, (C₂-C₄)haloalkenyl, (C₂-C₄)cyanoalkenyl, (C₂-C₄)alkynyl, (C₂-C₄)alkynyloxy-(C₁-C₄)alkyl, (C₂-C₄)haloalkynyloxy-(C₁-C₄)alkyl, (C₂-C₄)haloalkynyl, (C₂-C₄)cyanoalkynyl, (C₃-C₆)cycloalkyl, (C₃-C₆)cycloalkyl(C₃-C₆)cycloalkyl, (C₁-C₄)alkyl-(C₃-C₆)cycloalkyl, halo(C₃-C₆)cycloalkyl, (C₁-C₄)alkylamino, di(C₁-C₄)alkylamino, (C₃-C₆)cycloalkylamino, (C₁-C₄)alkylcarbonylamino, (C₁-C₄)alkylthio-(C₁-C₄)alkyl, (C₁-C₄)haloalkylthio-(C₁-C₄)alkyl, (C₁-C₄)alkylsulfinyl-(C₁-C₄)alkyl, (C₁-C₄)haloalkylsulfinyl-(C₁-C₄)alkyl, (C₁-C₄)alkylsulfonyl-(C₁-C₄)alkyl, (C₁-C₄)alkylcarbonyl-(C₁-C₄)alkyl, (C₁-C₄)haloalkylcarbonyl-(C₁-C₄)alkyl or (C₁-C₄)alkylsulfonylamino, R¹⁰, R¹¹, R¹², R¹³, R¹⁴, R¹⁵, R¹⁶, R¹⁷ are preferably independently hydrogen, cyano, halogen, nitro, hydroxyl, amino, tri(C₁-C₄)alkylsilyl, (C₃-C₆)cycloalkyl, (C₃-C₆)cycloalkyl-(C₃-C₆)cycloalkyl, (C₁-C₄)alkyl-(C₃-C₆)cycloalkyl, halo(C₃-C₆)cycloalkyl, (C₁-C₄)alkyl, (C₁-C₄)haloalkyl, (C₁-C₄)cyanoalkyl, (C₁-C₄)hydroxyalkyl, (C₁-C₄)alkoxy-(C₁-C₄)alkyl, (C₂-C₄)alkenyl, (C₂-C₄)haloalkenyl, (C₂-C₄)cyanoalkenyl, (C₂-C₄)alkynyl, (C₂-C₄)haloalkynyl, (C₂-C₄)cyanoalkynyl, (C₁-C₄)alkoxy, (C₁-C₄)haloalkoxy, (C₁-C₄)cyanoalkoxy, (C₁-C₄)alkoxy-(C₁-C₄)alkoxy, (C₁-C₄)alkylhydroxyimino, (C₁-C₄)alkoxyimino, (C₁-C₄)alkyl-(C₁-C₄)alkoxyimino, (C₁-C₄)haloalkyl-(C₁-C₄)alkoxyimino, (C₁-C₄)alkylthio, (C₁-C₄)haloalkylthio, (C₁-C₄)alkylthio-(C₁-C₄)alkyl, (C₁-C₄)alkylsulfinyl, (C₁-C₄)haloalkylsulfinyl, (C₁-C₄)alkylsulfinyl-(C₁-C₄)alkyl, (C₁-C₄)alkylsulfonyl, (C₁-C₄)haloalkylsulfonyl, (C₁-C₄)alkylsulfonyl-(C₁-C₄)alkyl, (C₁-C₄)alkylsulfonyloxy, (C₁-C₄)alkylcarbonyl, (C₁-C₄)haloalkylcarbonyl, aminocarbonyl, aminothiocarbonyl, (C₁-C₄)alkylaminocarbonyl, di(C₁-C₄)alkylaminocarbonyl, (C₃-C₆)cycloalkylaminocarbonyl, (C₁-C₄)alkylsulfonylamino, (C₁-C₄)alkylamino, di(C₁-C₄)alkylamino, aminosulfonyl, (C₁-C₄)alkylaminosulfonyl, di(C₁-C₄)alkylaminosulfonyl, aminothiocarbonyl, (C₁-C₄)alkylcarbamoyl (including —NHCOO(C₁-C₄)alkyl, —N(C₁-C₄)alkylCOO(C₁-C₄)alkyl, —OCONH(C₁-C₄)alkyl or —OCON(C₁-C₄)dialkyl), (C₁-C₄)alkylcarbonylamino, (C₁-C₄)alkylurea (including —NHCONH(C₁-C₄)alkyl, and —NHCON(C₁-C₄)dialkyl)

or are preferably phenyl or hetaryl, each of which is optionally mono- or disubstituted identically or differently, where (in the case of hetaryl) at least one carbonyl group may optionally be present and/or where possible substituents are in each case as follows: cyano, halogen, nitro, acetyl, amino, (C₃-C₆)cycloalkyl, (C₃-C₆)cycloalkyl-(C₃-C₆)cycloalkyl, (C₁-C₄)alkyl-(C₃-C₆)cycloalkyl, halo(C₃-C₆)cycloalkyl, (C₁-C₄)alkyl, (C₁-C₄)haloalkyl, (C₁-C₄)cyanoalkyl, (C₁-C₄)hydroxyalkyl, (C₁-C₄)alkoxy-(C₁-C₄)alkyl, (C₂-C₄)alkenyl, (C₂-C₄)haloalkenyl, (C₂-C₄)cyanoalkenyl, (C₂-C₄)alkynyl, (C₂-C₄)haloalkynyl, (C₂-C₄)cyanoalkynyl, (C₁-C₄)alkoxy, (C₁-C₄)haloalkoxy, (C₁-C₄)cyanoalkoxy, (C₁-C₄)alkoxy-(C₁-C₄)alkoxy, (C₁-C₄)alkylhydroxyimino, (C₁-C₄)alkoxyimino, (C₁-C₄)alkyl-(C₁-C₄)alkoxyimino, (C₁-C₄)haloalkyl-(C₁-C₄)alkoxyimino, (C₁-C₄)alkylthio, (C₁-C₄)haloalkylthio, (C₁-C₄)alkylthio-(C₁-C₄)alkyl, (C₁-C₄)alkylsulfinyl, (C₁-C₄)haloalkylsulfinyl, (C₁-C₄)alkylsulfinyl-(C₁-C₄)alkyl, (C₁-C₄)alkylsulfonyl, (C₁-C₄)haloalkylsulfonyl, (C₁-C₄)alkylsulfonyl-(C₁-C₄)alkyl, (C₁-C₄)alkylsulfonyloxy, (C₁-C₄)alkylcarbonyl, (C₁-C₄)haloalkylcarbonyl, aminocarbonyl, (C₁-C₄)alkylaminocarbonyl, di(C₁-C₄)alkylaminocarbonyl, (C₁-C₄)alkylsulfonylamino, (C₁-C₄)alkylamino, di(C₁-C₄)alkylamino, aminosulfonyl, (C₁-C₄)alkylaminosulfonyl, di(C₁-C₄)alkylaminosulfonyl or (C₁-C₄)alkylcarbonylamino, where only one or two of the R¹⁰, R¹¹, R¹², R¹³, R¹⁴, R¹⁵, R¹⁶, R¹⁷ radicals are a substituent other than hydrogen, and, if any of R¹⁰ and R¹⁴, R¹¹ and R¹⁵, R¹² and R¹⁶ or R¹³ and R¹⁷ are both not hydrogen, R¹⁴, R¹⁵, R¹⁶ and R¹⁷ are each independently only cyano, halogen, (C₃-C₆)cycloalkyl, (C₃-C₆)cycloalkyl-(C₃-C₆)cycloalkyl, (C₁-C₄)alkyl-(C₃-C₆)cycloallyl, halo(C₃-C₆)cycloalkyl, (C₁-C₄)alkyl, (C₁-C₄)haloalkyl or (C₁-C₄)cyanoalkyl, Q is preferably a heteroaromatic 9-membered or 12-membered fused bicyclic or tricyclic ring system from the group of Q1 to Q15:

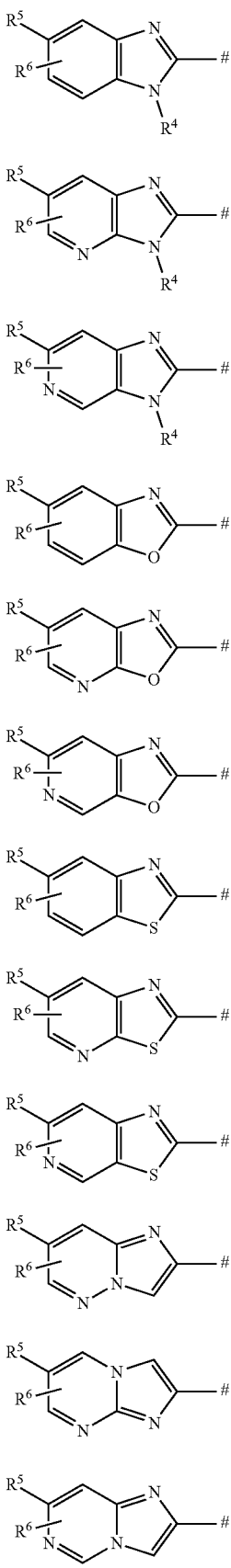

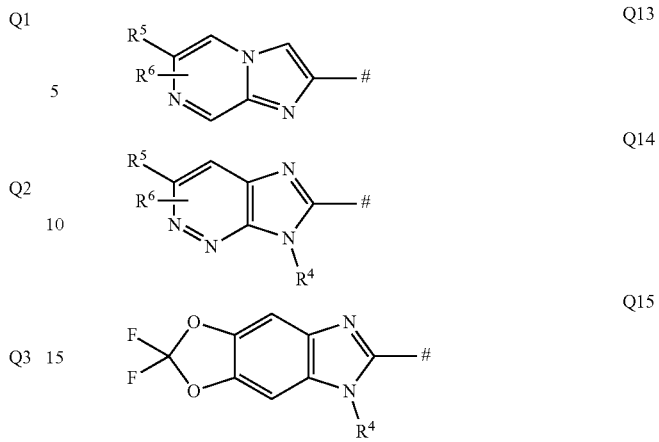

where
R⁴ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$haloalkynyl or $(C_3-C_6)$cycloalkyl and R⁵, R⁶ are independently hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$haloalkyl-$(C_3-C_6)$cycloalkyl, cyano-$(C_3-C_6)$cycloalkyl, halo-$(C_3-C_6)$cycloalkyl, $(C_1-C_4)$alkoxy, $(C_1-C_4)$haloalkoxy, $(C_1-C_4)$alkoxyimino, $(C_1-C_4)$haloalkoxyimino $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl, $(C_1-C_4)$haloalkylcarbonyl, aminocarbonyl, $(C_1-C_4)$alkylaminocarbonyl, di$(C_1-C_4)$alkylaminocarbonyl, $(C_1-C_4)$alkylsulfonylamino, $(C_1-C_4)$alkylamino, di$(C_1-C_4)$alkylamino, aminosulfonyl, $(C_1-C_4)$alkylaminosulfonyl or di$(C_1-C_4)$alkylaminosulfonyl
and
n is preferably 0, 1 or 2.

Configuration 3

Compounds of the formula I(a) or I(b) in which, more preferably,
if ⁄⁄ represent exclusively double bonds and hence Aa to Ad together with the carbon atoms adjacent to Aa and Ad in each case form an aromatic ring,
Aa is nitrogen or $C(R^{10})$,
Ab is nitrogen or $C(R^{11})$,
Ac is nitrogen or $C(R^{12})$, and
Ad is nitrogen or $C(R^{13})$,
where not more than two of Aa, Ab, Ac and Ad can be nitrogens,
or, if ⁄⁄ represent exclusively single bonds,
Aa is $C(R^{10})(R^{14})$,
Ab is $C(R^{11})(R^{15})$,
Ac is $C(R^{12})(R^{16})$ and
Ad is $C(R^{13})(R^{17})$,
R¹ is more preferably $(C_1-C_4)$alkyl, $(C_1-C_4)$hydroxyalkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, ($C_1$-$C_4$)alkylthio-($C_1$-$C_4$)alkyl, ($C_1$-$C_4$)alkylsulfinyl-($C_1$-$C_4$)alkyl or ($C_1$-$C_4$)alkylsulfonyl-($C_1$-$C_4$)alkyl, $R^{10}$, $R^{11}$, $R^{12}$, $R^{13}$, $R^{14}$, $R^{15}$, $R^{16}$, $R^{17}$ are independently more preferably hydrogen, cyano, halogen, nitro, hydroxyl, amino, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_3$-$C_6$)cycloalkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, ($C_1$-$C_4$)alkylcarbamoyl (including —NHCOO($C_1$-$C_4$)alkyl and —N($C_1$-$C_4$)alkylCOO($C_1$-$C_4$)alkyl), ($C_1$-$C_4$)alkylcarbonylamino, ($C_1$-$C_4$)alkylurea (including —NHCONH($C_1$-$C_4$)alkyl and —NHCON($C_1$-$C_4$)dialkyl)

or are more preferably phenyl or hetaryl, each of which is optionally mono- or disubstituted identically or differently, where (in the case of hetaryl) at least one carbonyl group may optionally be present and/or where possible substituents are in each case as follows: cyano, halogen, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, ($C_1$-$C_4$)alkylcarbonylamino, where only one or two of the $R^{10}$, $R^{11}$, $R^{12}$, $R^{13}$, $R^{14}$, $R^{15}$, $R^{16}$, $R^{17}$ radicals are a substituent other than hydrogen, and, if any of $R^{10}$ and $R^{14}$, $R^{11}$ and $R^{15}$, $R^{12}$ and $R^{16}$ or $R^{13}$ and $R^{17}$ are both not hydrogen, $R^{14}$, $R^{15}$, $R^{16}$ and $R^{17}$ are each independently only cyano, halogen, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalyl, halo($C_3$-$C_6$)cycloalkyl, ($C_1$-$C_4$)alkyl, ($C_1$-$C_4$)haloalkyl or ($C_1$-$C_4$)cyanoalkyl, Q is more preferably a heteroaromatic 9-membered or 12-membered fused bicyclic or tricyclic ring system from the group of Q1 to Q15, where $R^4$ is hydrogen, ($C_1$-$C_4$)alkyl, ($C_3$-$C_6$)cycloalkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)haloalkenyl, ($C_2$-$C_4$)alkynyl or ($C_2$-$C_4$)haloalkynyl and $R^5$, $R^6$ are independently hydrogen, cyano, halogen, ($C_1$-$C_4$)alkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)haloalkyl-($C_3$-$C_6$)cycloalkyl, cyano-($C_3$-$C_6$)cycloalkyl, halo($C_3$-$C_6$)cycloalkyl, ($C_1$-$C_4$)alkoxy, ($C_1$-$C_4$)haloalkoxy, ($C_1$-$C_4$)alkoxyimino, ($C_1$-$C_4$)haloalkoxyimino ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)haloalkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl or di($C_1$-$C_4$)alkylaminosulfonyl and n is more preferably 0, 1 or 2.

Configuration 4

Compounds of the formula I(a) or I(b) in which, even more preferably, if ⟋⟋ represent exclusively double bonds and hence Aa to Ad together with the carbon atoms adjacent to Aa and Ad in each case form an aromatic ring, Aa is nitrogen or C($R^{10}$), Ab is nitrogen or C($R^{11}$), Ac is nitrogen or C($R^{12}$), and Ad is nitrogen or C($R^{13}$), where not more than two of Aa, Ab, Ac and Ad can be nitrogens, or, if ⟋⟋ represent exclusively single bonds, Aa is C($R^{10}$)($R^{14}$), Ab is C($R^{11}$)($R^{15}$), Ac is C($R^{12}$)($R^{16}$) and Ad is C($R^{13}$)($R^{11}$), $R^1$ is even more preferably methyl, ethyl, n-propyl, i-propyl, cyclopropyl, n-butyl, i-butyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^{10}$, $R^{11}$, $R^{12}$, $R^{13}$, $R^{14}$, $R^{15}$, $R^{16}$, $R^{17}$ are even more preferably independently hydrogen, cyano, halogen, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)haloalkylthio, ($C_1$-$C_4$)haloalkylsulfinyl, ($C_1$-$C_4$)haloalkylsulfonyl, aminocarbonyl, ($C_1$-$C_4$)alkylaminocarbonyl, ($C_3$-$C_6$)cycloalkylaminocarbonyl, ($C_1$-$C_4$)alkylcarbamoyl (including —NHCOO($C_1$-$C_4$)alkyl and —N($C_1$-$C_4$)alkylCOO ($C_1$-$C_4$)alkyl), ($C_1$-$C_4$)alkylcarbonylamino or ($C_1$-$C_4$)alkylurea (including —NHCONH($C_1$-$C_4$)alkyl and —NHCON($C_1$-$C_4$)dialkyl), where only one or two of the $R^{10}$, $R^{11}$, $R^{12}$, $R^{13}$, $R^{14}$, $R^{15}$, $R^{16}$, $R^{17}$ radicals are a substituent other than hydrogen, and, if any of $R^{10}$ and $R^{14}$, $R^{11}$ and $R^{15}$, $R^{12}$ and $R^{16}$ or $R^{13}$ and $R^{17}$ are both not hydrogen, $R^{14}$, $R^{15}$, $R^{16}$ and $R^{17}$ are each independently only cyano, halogen, ($C_1$-$C_4$)alkyl or ($C_1$-$C_4$)haloalkyl, Q is even more preferably a heteroaromatic 9-membered or 12-membered fused bicyclic or tricyclic ring system from the group of Q2, Q3, Q5, Q6, Q8, Q9, Q14 or Q15, where $R^4$ is even more preferably ($C_1$-$C_4$)alkyl, ($C_1$-$C_4$)haloalkyl, ($C_3$-$C_6$)cycloalkyl or ($C_1$-$C_4$)alkoxy-($C_1$-$C_4$)alkyl, $R^5$ is even more preferably cyano, halogen, ($C_1$-$C_4$)haloalkyl, halo-($C_3$-$C_6$)cycloalkyl, ($C_1$-$C_4$)haloalkoxy, ($C_1$-$C_4$)haloalkylthio, ($C_1$-$C_4$)haloalkylsulfinyl, ($C_1$-$C_4$)alkylsulfonyl, ($C_1$-$C_4$)haloalkylsulfonyl, ($C_1$-$C_4$)haloalkylcarbonyl or ($C_1$-$C_4$)haloalkylsulfonyloxy, $R^6$ is even more preferably hydrogen, cyano, halogen, $(C_1-C_4)$alkyl, $(C_1-C_4)$haloalkyl or $(C_3-C_6)$cycloalkyl and n is even more preferably 0, 1 or 2.

Configuration 5-1

Compounds of the formula I(a) or I(b) in which, in particular, if ⇌ represent exclusively double bonds and hence Aa to Ad together with the carbon atoms adjacent to Aa and Ad in each case form an aromatic ring, Aa is $C(R^{10})$,
Ab is nitrogen or $C(R^{11})$,
Ac is $C(R^{12})$ and
Ad is $C(R^{13})$,
or, if ⇌ represent exclusively single bonds,
Aa is $C(R^{10})(R^{14})$,
Ab is $C(R^{11})(R^{15})$,
Ac is $C(R^{12})(R^{16})$ and
Ad is $C(R^{13})(R^{17})$,
$R^1$ is particularly ethyl,
$R^{10}$, $R^{11}$, $R^{12}$, $R^{13}$ are particularly independently hydrogen, fluorine, chlorine, bromine, iodine, cyano, methyl, ethyl, trifluoromethyl, trifluoromethoxy, 2,2,2-trifluoroethoxy, acetylamino (methylcarbonylamino, —NHCOMe), cyclopropylamido (cyclopropylaminocarbonyl), methylcarbamoyl (—NHCOOMe), methylurea (—NHCONHMe) or cyclopropyl,
where only one or two of the $R^{10}$, $R^{11}$, $R^{12}$, $R^{13}$ radicals are a substituent other than hydrogen,
$R^{14}$, $R^{15}$, $R^{16}$, $R^{17}$ are particularly independently hydrogen or $(C_1-C_4)$alkyl, preferably hydrogen,
Q is particularly a heteroaromatic 9-membered fused bicyclic ring system from the group of Q2, Q3 and Q14

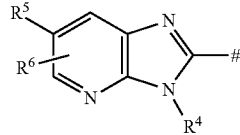
Q2

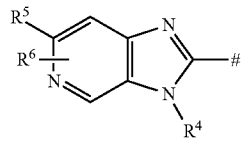
Q3

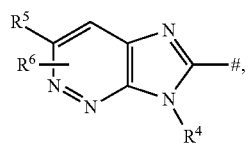
Q14 where
$R^4$ is particularly methyl,
$R^5$ is particularly trifluoromethyl or pentafluoroethyl,
$R^6$ is particularly hydrogen and
n is particularly 0, 1 or 2.

Configuration 5-2

Compounds of the formula I(a) or I(b) in which, in particular, if ⇌ represent exclusively double bonds and hence Aa to Ad together with the carbon atoms adjacent to Aa and Ad in each case form an aromatic ring, Aa is $C(R^{10})$,
Ab is $C(R^{11})$,
Ac is $C(R^{12})$ and
Ad is $C(R^{13})$,
or, if ⇌ represent exclusively single bonds,
Aa is $C(R^{10})(R^{14})$,
Ab is $C(R^{11})(R^{15})$,
Ac is $C(R^{12})(R^{16})$ and
Ad is $C(R^{13})(R^{17})$,
$R^1$ is particularly ethyl,
$R^{10}$, $R^{11}$, $R^{12}$, $R^{13}$ are particularly independently hydrogen, fluorine, chlorine, bromine, iodine, cyano, methyl, ethyl, trifluoromethyl, trifluoromethoxy, 2,2,2-trifluoroethoxy, acetylamino (methylcarbonylamino), cyclopropylamido (cyclopropylaminocarbonyl), methylcarbamoyl (—NHCOOMe), methylurea (—NHCONHMe) or cyclopropyl,
where only one or two of the $R^{10}$, $R^{11}$, $R^{12}$, $R^{13}$ radicals are a substituent other than hydrogen,
$R^{14}$, $R^{15}$, $R^{16}$, $R^{17}$ are particularly independently hydrogen or $(C_1-C_4)$alkyl, preferably hydrogen,
Q is particularly a heteroaromatic 9-membered fused bicyclic ring system from the group of Q2, Q3, Q5 and Q14

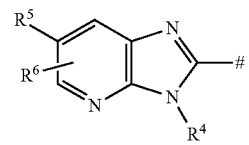
Q2

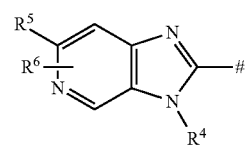
Q3

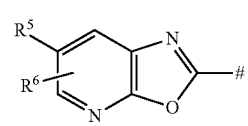
Q5

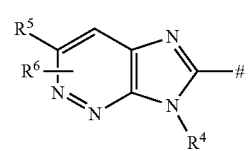
Q14 where
$R^4$ is particularly methyl,
$R^5$ is particularly trifluoromethyl or pentafluoroethyl,
$R^6$ is particularly hydrogen and
n is particularly 0, 1 or 2.

Configuration 6-1

Compounds of the formula I(a) or I(b) in which, especially, if ⇌ represent exclusively double bonds and hence Aa to Ad together with the carbon atoms adjacent to Aa and Ad in each case form an aromatic ring, Aa is $C(R^{10})$,
Ab is nitrogen or $C(R^{11})$,
Ac is $C(R^{12})$ and
Ad is $C(R^{13})$, where
$R^{10}$ is especially hydrogen, chlorine or trifluoromethyl,
$R^{11}$ is especially hydrogen, chlorine, —NHCOMe or trifluoromethyl,
$R^{12}$ is especially hydrogen, chlorine or trifluoromethyl, $R^{13}$ is especially hydrogen, chlorine or trifluoromethyl,
or, if ⌁ represent exclusively single bonds,
Aa is $C(R^{10})(R^{14})$,
Ab is $C(R^{11})(R^{15})$,
Ac is $C(R^{12})(R^{16})$ and
Ad is $C(R^{13})(R^{17})$, where
$R^{10}$, $R^{12}$, $R^{13}$, $R^{14}$, $R^{16}$, $R^{17}$ are especially hydrogen,
$R^{11}$ is especially hydrogen or methyl and
$R^{15}$ is especially hydrogen or methyl,
$R^1$ is especially ethyl,
Q is especially a heteroaromatic 9-membered fused bicyclic ring system from the group of Q2 and Q3

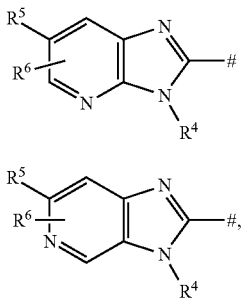

where
$R^4$ is especially methyl,
$R^5$ is especially trifluoromethyl or pentafluoroethyl,
$R^6$ is especially hydrogen and
n is especially 0, 1 or 2.

Configuration 6-2:
Compounds of the formula I(a) or I(b) in which, especially,
⌁ represent exclusively double bonds and hence Aa to Ad together with the carbon atoms adjacent to Aa and Ad in each case form an aromatic ring,
Aa is $C(R^{10})$,
Ab is $C(R^{11})$,
Ac is $C(R^{12})$ and
Ad is $C(R^{13})$,
$R^1$ is especially ethyl,
$R^{10}$ is especially hydrogen, chlorine or trifluoromethyl,
$R^{11}$ is especially hydrogen, chlorine or trifluoromethyl,
$R^{12}$ is especially hydrogen, chlorine or trifluoromethyl,
$R^{13}$ is especially hydrogen, chlorine or trifluoromethyl,
where only one of the $R^{10}$, $R^{11}$, $R^{12}$ or $R^{13}$ radicals is a substituent other than hydrogen,
Q is especially a heteroaromatic 9-membered fused bicyclic ring system from the group of Q2 and Q3

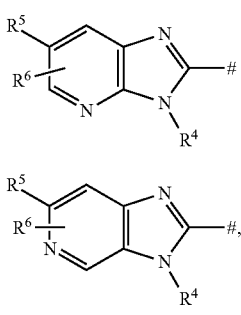

where
$R^4$ is especially methyl,
$R^5$ is especially trifluoromethyl or pentafluoroethyl,
$R^6$ is especially hydrogen and
n is especially 0, 1 or 2.

In the following, the term Configuration (5) is synonymous with Configuration 5-1 or Configuration 5-2, and Configuration (6) is synonymous with Configuration 6-1 or 6-2.

The substituent Aa is identical to the substituent $A_a$; the substituent Ab is identical to the substituent $A_b$, the substituent Ac is identical to the substituent $A_c$, the substituent Ad is identical to the substituent $A_d$.

In a preferred embodiment, the invention relates to compounds of the formula (Ia) or (Ib) where Q is Q2, Q3, Q5, Q6, Q8, Q9, Q14 or Q15, where
$R^4$ is $(C_1-C_4)$alkyl, $(C_1-C_4)$haloalkyl, $(C_3-C_6)$cycloalkyl or $(C_1-C_4)$alkoxy-$(C_1-C_4)$alkyl,
$R^5$ is cyano, halogen, $(C_1-C_4)$haloalkyl, halo-$(C_3-C_6)$cycloalkyl, $(C_1-C_4)$haloalkoxy, $(C_1-C_4)$haloalkylthio, $(C_1-C_4)$haloalkylsulfinyl, $(C_1-C_4)$alkylsulfonyl, $(C_1-C_4)$haloalkylsulfonyl, $(C_1-C_4)$haloalkylcarbonyl or $(C_1-C_4)$haloalkylsulfonyloxy,
$R^6$ is hydrogen, cyano, halogen, $(C_1-C_4)$alkyl, $(C_1-C_4)$haloalkyl or $(C_3-C_6)$cycloalkyl and
Aa, Ab, Ac, Ad, $R^1$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (5) or configuration (6).

In a particularly preferred embodiment, the invention relates to compounds of the formula (Ia) or (Ib) where Q is Q2, Q3 or Q14, where
$R^4$ is methyl,
$R^5$ is trifluoromethyl or pentafluoroethyl,
$R^6$ is hydrogen
and Aa, Ab, Ac, Ad, $R^1$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (6).

In a very particularly preferred embodiment, the invention relates to compounds of the formula (Ia) or (Ib) where Q is Q2 or Q3, where
$R^4$ is methyl,
$R^5$ is trifluoromethyl or pentafluoroethyl,
$R^6$ is hydrogen
and Aa, Ab, Ac, Ad, $R^1$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5).

In a preferred embodiment, the invention relates to compounds of the formula (Ia) or (Ib) where Q is Q2, Q3, Q5, Q6, Q8, Q9, Q14 or Q15, where
$R^4$ is $(C_1-C_4)$alkyl, $(C_1-C_4)$haloalkyl, $(C_3-C_6)$cycloalkyl or $(C_1-C_4)$alkoxy-$(C_1-C_4)$alkyl,
$R^6$ is hydrogen, cyano, halogen, $(C_1-C_4)$alkyl, $(C_1-C_4)$haloalkyl or $(C_3-C_6)$cycloalkyl and
Aa, Ab, Ac, Ad, $R^1$, $R^5$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (5) or configuration (6).

In a particularly preferred embodiment, the invention relates to compounds of the formula (Ia) or (Ib) where Q is Q2, Q3 or Q14, where
$R^4$ is methyl,
$R^6$ is hydrogen and Aa, Ab, Ac, Ad, $R^1$, $R^5$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (6).

In a very particularly preferred embodiment, the invention relates to compounds of the formula (Ia) or (Ib) where Q is Q2 or Q3, where
$R^4$ is methyl,
$R^6$ is hydrogen
and Aa, Ab, Ac, Ad, $R^1$, $R^5$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5).

In a preferred embodiment, the invention relates to compounds of the formula (Ia) or (Ib) where Q is Q2, Q3, Q5, Q6, Q8, Q9, Q14 or Q15, where
$R^4$ is $(C_1-C_4)$alkyl, preferably methyl, and
Aa, Ab, Ac, Ad, $R^1$, $R^5$, $R^6$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

In a particularly preferred embodiment, the invention relates to compounds of the formula (Ia) or (Ib) where Q is Q2, Q3 or Q14, where
$R^4$ is $(C_1-C_4)$alkyl, preferably methyl, and
Aa, Ab, Ac, Ad, $R^1$, $R^5$, $R^6$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

In a very particularly preferred embodiment, the invention relates to compounds of the formula (Ia) or (Ib) where Q is Q2 or Q3, where
$R^4$ is $(C_1-C_4)$alkyl, preferably methyl, and
Aa, Ab, Ac, Ad, $R^1$, $R^5$, $R^6$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

In a preferred embodiment, the invention relates to compounds of the formula (Ia) or (Ib) where Q is Q2, Q3, Q5, Q6, Q8, Q9, Q14 or Q15, where
$R^6$ is hydrogen and
Aa, Ab, Ac, Ad, $R^1$, $R^4$, $R^5$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

In a particularly preferred embodiment, the invention relates to compounds of the formula (Ia) or (Ib) where Q is Q2, Q3 or Q14, where
$R^6$ is hydrogen and
Aa, Ab, Ac, Ad, $R^1$, $R^4$, $R^5$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

In a very particularly preferred embodiment, the invention relates to compounds of the formula (Ia) or (Ib) where Q is Q2 or Q3, where
$R^6$ is hydrogen and
Aa, Ab, Ac, Ad, $R^1$, $R^4$, $R^5$, $R^{10}$ $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

In a further preferred embodiment, the invention relates to compounds of the formula (Ia) or (Ib) where $R^1$ is ethyl and
Aa, Ab, Ac, Ad, $R^{10}$, $R^{11}$, $R^{12}$, $R^{13}$, $R^{14}$, $R^{15}$, $R^{16}$, $R^{17}$, Q, $R^4$, $R^5$, $R^6$ and n have the definitions described in configuration (1) or configuration (2) or configuration (3) or configuration (4).

Preferably, for the formulae (Ia) and (Ib), this gives rise to the following structures (Ia1) to (Ia4) and (Ib1) to (Ib4):

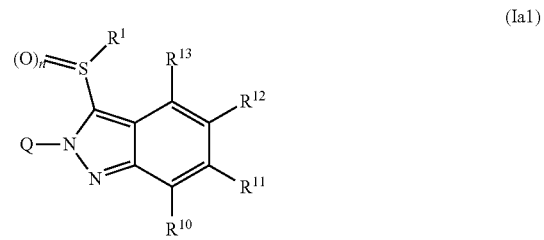

(Ia1)

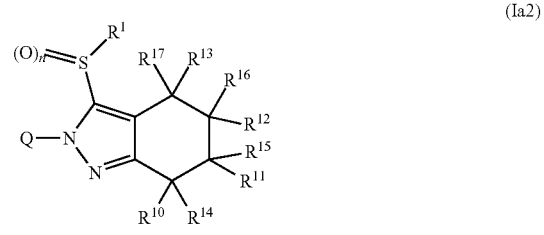

(Ia2)

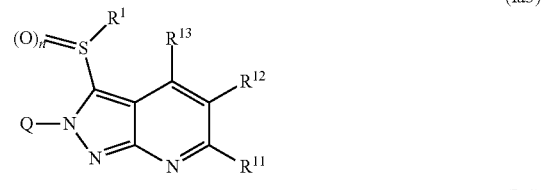

(Ia3)

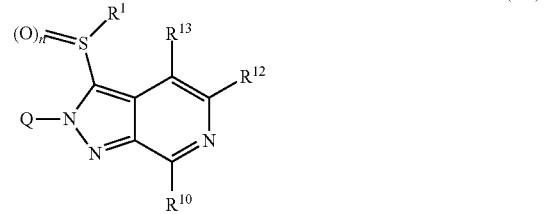

(Ia4)

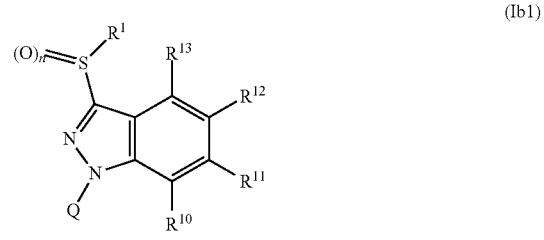

(Ib1)

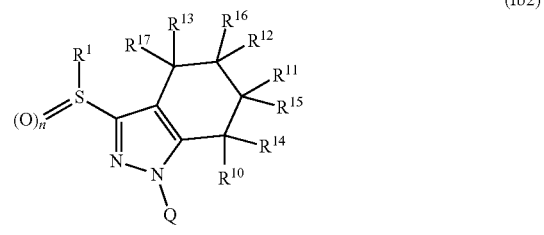

(Ib2)

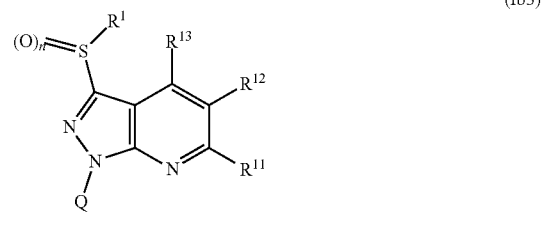

(Ib3)

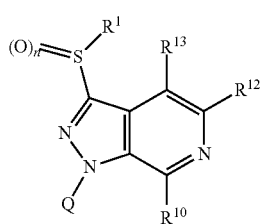
(Ib4)

where R$^1$, R$^{10}$, R$^{11}$, R$^{12}$, R$^{13}$, R$^{14}$, R$^{15}$, R$^{16}$, R$^{17}$, Q, R$^4$, R$^5$, R$^6$ and n have the definitions described in configuration (1) or configuration (2) or configuration (3) or configuration (4) or configuration (5) or configuration (6).

Even more preferably, this gives rise to the compounds of the formulae (Ia5) to (Ia16):

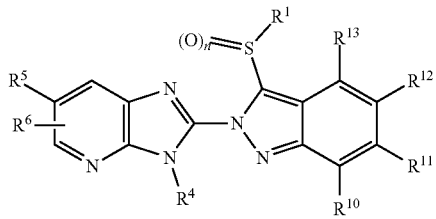
(Ia5)

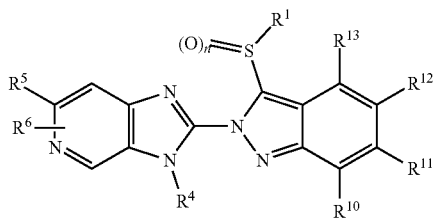
(Ia6)

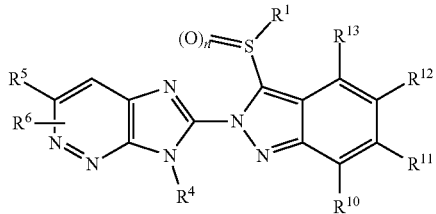
(Ia7)

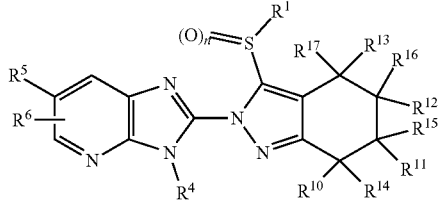
(Ia8)

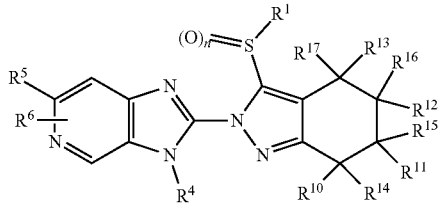
(Ia9)

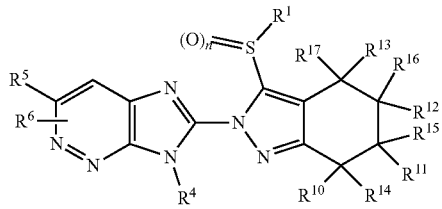
(Ia10)

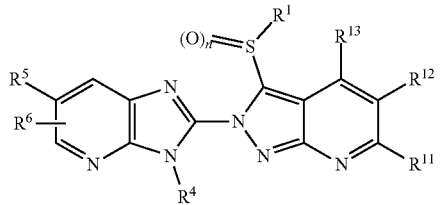
(Ia11)

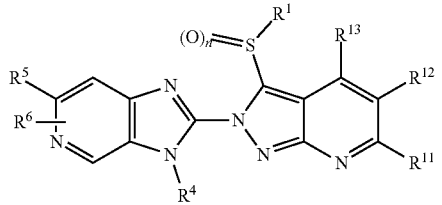
(Ia12)

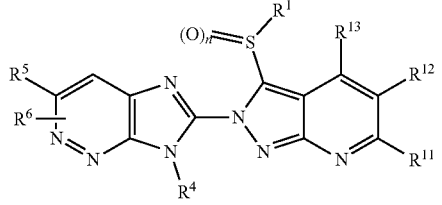
(Ia13)

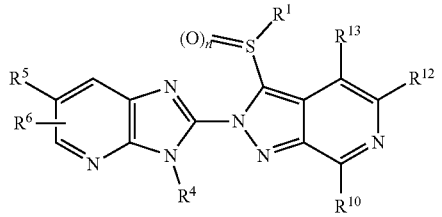
(Ia14)

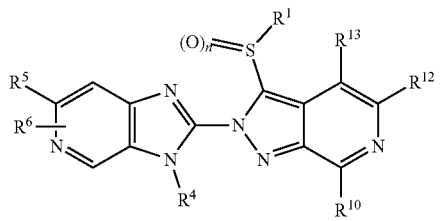
(Ia15)

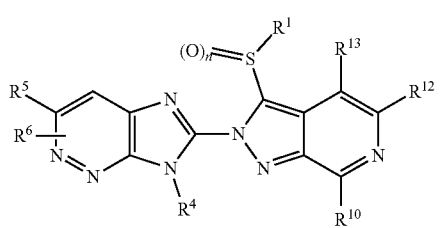
(Ia16)

where R$^1$, R$^{10}$, R$^{11}$, R$^{12}$, R$^{13}$, R$^{14}$, R$^{15}$, R$^{16}$, R$^{17}$, R$^4$, R$^5$, R$^6$ and n have the definitions described in configuration (1)

or configuration (2) or configuration (3) or configuration (4) or configuration (5) or configuration (6).

Especially preferred here are the compounds of the formulae (Ia5) to (Ia10) and formula (Ia14) and particularly the compounds (Ia5) to (Ia7) and (Ia14).

This especially gives rise to the structures (Ia17) to (Ia25):

(Ia17)
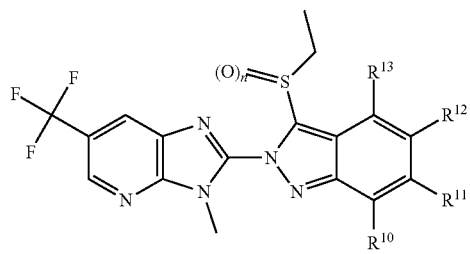

(Ia18)
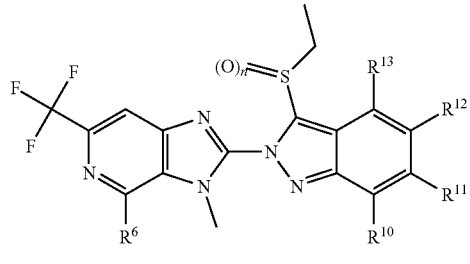

(Ia19)
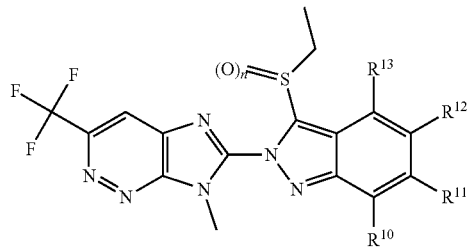

(Ia20)
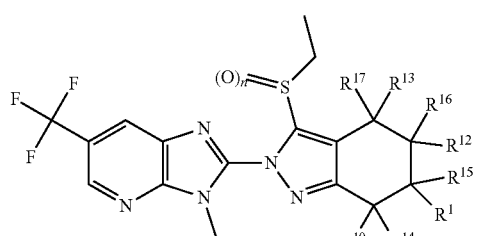

(Ia21)

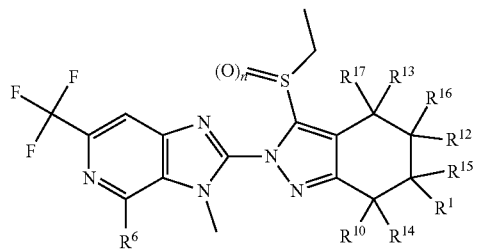

(Ia22)
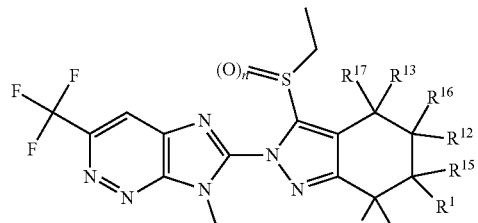

(Ia23)
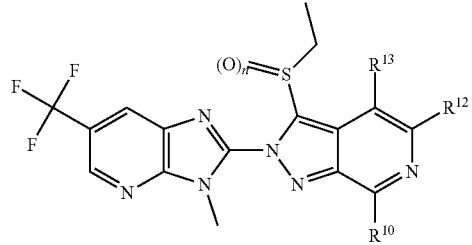

(Ia24)
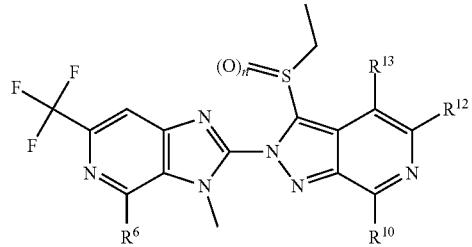

(Ia25)

where $R^6$, $R^{10}$, $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

Especially preferred here are the compounds of the formulae (Ia17) to (Ia19) and (Ia23).

Further preferably, in the formulae (Ia) and (Ib), if ⌇ represents exclusively single bonds, Aa is $C(R^{10})(R^{14})$, Ab is $C(R^{11})(R^{15})$, Ac is $C(R^{12})(R^{16})$ and Ad is $C(R^{13})(R^{17})$, Q is not Q10, Q11, Q12 or Q13.

The compounds according to the invention are preferably compounds of the formula (Ia), more preferably of the formulae (Ia1) or (Ia2) and most preferably of the formula (Ia1).

Further particularly preferred are the compounds of the formula I-1 to I-5 and I-7 to I-19.

Further especially preferred are the compound of the formula I-1, I-2, I-3, I-4, I-5, I-7, I-8, I-9, I-10, I-11, I-18, I-19.

I-1
I-2
I-3
I-4
I-5
I-7
I-8
I-9
I-10
I-11
I-12
I-13

-continued

I-14
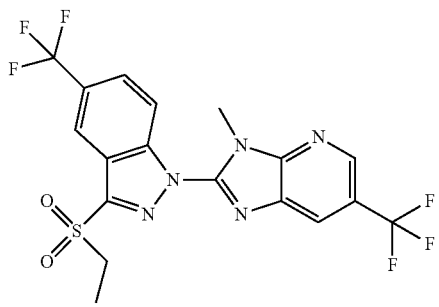

I-15
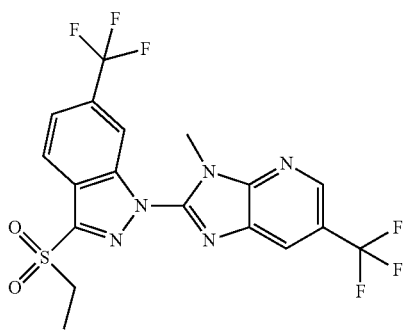

I-16
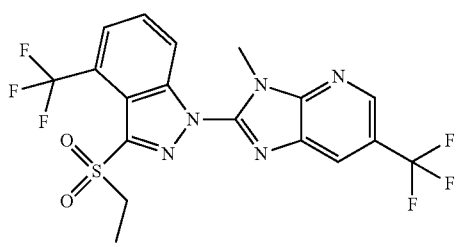

I-17
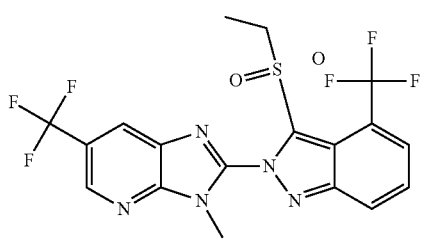

I-18
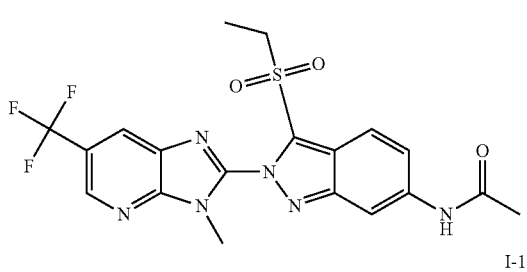

I-19
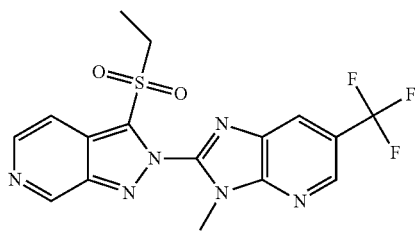

Particularly preferred are the compounds of the formulae (Ia) or (Ib), preferably of the formula (Ia), according to the embodiments described above, in particular according to configuration (1) or configuration (2) or configuration (3) or configuration (4) or configuration (5) or configuration (6), where, in the case that for the compounds of the formula (Ia) ⇌ represents exclusively double bonds,
$R^1$ is $C_1$-$C_6$ alkyl,
Aa and Ad are CH,
Ab is $C(R^{11})$,
Ac is $C(R^{12})$
and
Q is Q2, where
$R^4$ is $C_1$-$C_6$ alkyl,
$R^6$ is hydrogen and
$R^5$ is $(C_1$-$C_6)$haloalkyl, $(C_1$-$C_6)$haloalkylthio, $(C_1$-$C_6)$haloalkylsulfinyl or $(C_1$-$C_6)$haloalkylsulfonyl,
at least one of the radicals $R^{11}$ or $R^{12}$ is not hydrogen, halogen or $(C_1$-$C_6)$haloalkyl.

Further particularly preferred are the compounds of the formulae (Ia) or (Ib), preferably of the formula (Ia), according to the embodiments described above, in particular according to configuration (1) or configuration (2) or configuration (3) or configuration (4) or configuration (5) or configuration (6), where, in the case that for the compounds of the formula (Ia)
⇌ represents exclusively double bonds,
$R^1$ is $C_1$-$C_6$ alkyl,
Aa and Ad are CH,
Ab is $C(R^{11})$,
Ac is $C(R^{12})$
$R^{11}$ and $R^{12}$ are independently hydrogen, halogen or $(C_1$-$C_6)$haloalkyl
and
Q is Q2,
$R^4$ is $C_1$-$C_6$ alkyl and
$R^6$ is hydrogen,
$R^5$ is not $(C_1$-$C_6)$haloalkyl, $(C_1$-$C_6)$haloalkylthio, $(C_1$-$C_6)$haloalkylsulfinyl or $(C_1$-$C_6)$haloalkylsulfonyl.

Further particularly preferred are the compounds of the formulae (Ia) or (Ib), preferably of the formula (Ia), according to the embodiments described above, in particular according to configuration (1) or configuration (2) or configuration (3) or configuration (4) or configuration (5) or configuration (6), where compounds of the formula (Y)

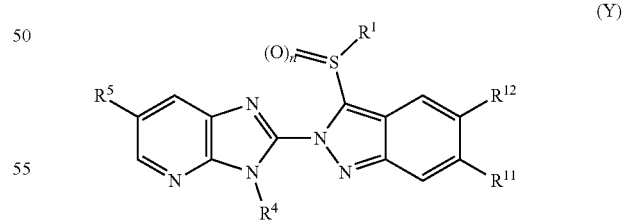

(Y)

in which
$R^1$ is $(C_1$-$C_6)$alkyl,
$R^4$ is $(C_1$-$C_6)$alkyl,
$R^5$ is $(C_1$-$C_6)$haloalkyl, $(C_1$-$C_6)$haloalkylthio, $(C_1$-$C_6)$haloalkylsulfinyl or $(C_1$-$C_6)$haloalkylsulfonyl,
$R^{11}$ and $R^{12}$ are independently each hydrogen, halogen or $(C_1$-$C_6)$ haloalkyl and
n is 0, 1 or 2
are excepted.

Further particularly preferred are the compounds of the formulae (Ia) or (Ib), preferably of the formula (Ia), according to the embodiments described above, in particular according to configuration (1) or configuration (2) or configuration (3) or configuration (4) or configuration (5) or configuration (6), where compounds of the formula (Y) in which
R¹ is ethyl,
R⁴ is methyl,
R⁵ is trifluoromethyl,
R¹¹ is hydrogen,
R¹² is trifluoromethyl and
n is 0 or 2
are excepted.

A particularly preferred aspect of the invention comprises the compounds of the formulae (Ia) or (Ib), preferably of the formula (Ia), in which ⚏ represents exclusively single bonds.

Especially preferred here the structure resulting for the formula (Ia) is the following structure (Ia2),

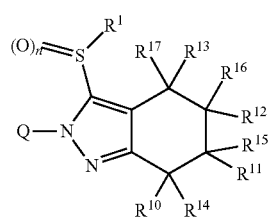
(Ia2)

where $R^1$, $R^{10}$, $R^{11}$, $R^{12}$, $R^{13}$, $R^{14}$, $R^{15}$, $R^{16}$, $R^{17}$, Q, $R^4$, $R^5$, $R^6$ and n have the definitions described in configuration (1) or configuration (2) or configuration (3) or configuration (4) or configuration (5) or configuration (6).

Resulting with very particular preference are the compounds of the formulae (Ia8) to (Ia10)

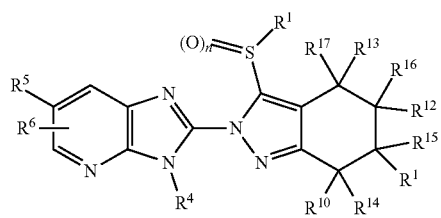
(Ia8)

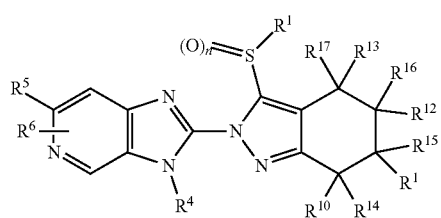
(Ia9)

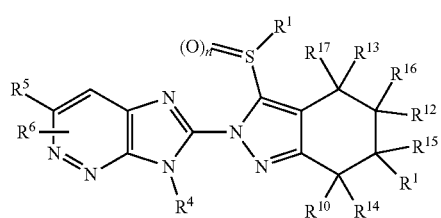
(Ia10)

where $R^1$, $R^{10}$, $R^{11}$, $R^{12}$, $R^{13}$, $R^{14}$, $R^{15}$, $R^{16}$, $R^{17}$, $R^4$, $R^5$, $R^6$ and n have the definitions described in configuration (1) or configuration (2) or configuration (3) or configuration (4) or configuration (5) or configuration (6).

Emphasis here is given to the compounds of the formulae (Ia8) and (Ia9).

Arising in particular are the structures (Ia20) to (Ia22)

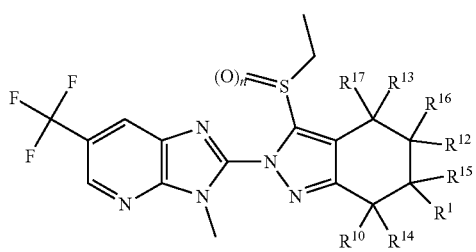
(Ia20)

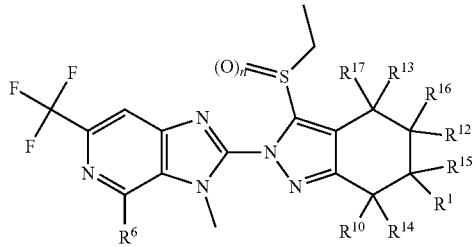
(Ia21)

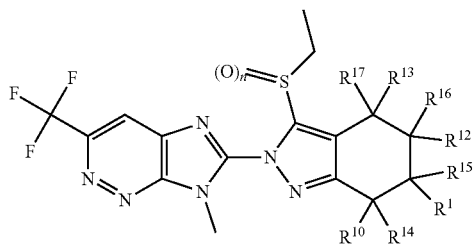
(Ia22)

where $R^6$, $R^{10}$, $R^{11}$, $R^{12}$, $R^{13}$, $R^{14}$, $R^{15}$, $R^{16}$, $R^{17}$ and n have the definitions described in configuration (1) or configuration (2) or configuration (3) or configuration (4) or configuration (5) or configuration (6).

Especially preferred here are also the structures of the formulae I-10 and I-11.

Further preferred are compounds of the formulae (Ia) or (Ib), preferably of the formula (Ia), where at least one of the variables Aa, Ab, Ac and Ad is nitrogen, more preferably one of the variables Aa, Ab, Ac and Ad is nitrogen. Very preferably here exclusively the variable Ab is nitrogen.

By definition, unless stated otherwise, halogen is selected from the group of fluorine, chlorine, bromine and iodine, preferably in turn from the group of fluorine, chlorine and bromine.

In the context of the present invention, unless defined differently elsewhere, the term "alkyl", either on its own or else in combination with further terms, for example haloalkyl, is understood to mean a radical of a saturated, aliphatic hydrocarbon group which has 1 to 12 carbon atoms and may be branched or unbranched. Examples of $C_1$-$C_{12}$ alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. The term "alkoxy", either on its own or else in combination with further terms, for example haloalkoxy, is understood in the present case to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms may be identical or different. Unless stated otherwise, optionally substituted radicals may be mono- or polysubstituted, where the substituents in the case of polysubstitutions may be the same or different.

According to the invention, unless defined differently elsewhere, the term "aryl" is understood to mean an aromatic radical having 6 to 14 carbon atoms, preferably phenyl, naphthyl, anthryl or phenanthrenyl, more preferably phenyl.

Unless defined differently elsewhere, the term "arylalkyl" is understood to mean a combination of the radicals "aryl" and "alkyl" defined in accordance with the invention, where the radical is generally bonded via the alkyl group; examples of these are benzyl, phenylethyl or α-methylbenzyl, particular preference being given to benzyl.

Unless defined differently elsewhere, "hetaryl" denotes a mono-, bi- or tricyclic heterocyclic group of carbon atoms and at least one heteroatom, where at least one cycle is aromatic. Preferably, the hetaryl group contains 3, 4, 5, 6, 7 or 8 carbon atoms selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, imidazopyridinyl and indolizinyl.

Depending on the nature of the substituents, the compounds of the formula (Ia) or (Ib) may be in the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

The compounds of the formula (I) can also be present as salts, in particular acid addition salts and metal salt complexes. The compounds of the formula (I) and their acid addition salts and metal salt complexes have good efficacy, especially for control of animal pests.

Suitable salts of the compounds of the general formula (I) include customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulfates, trihydrosulfates, or phosphates, salts with organic carboxylic acids or organic sulfonic acids, for example formates, acetates, trifluoroacetates, maleates, tartrates, methanesulfonates, benzenesulfonates or para-toluenesulfonates, salts with basic amino acids, for example arginates, aspartates or glutamates, and the like.

The radical definitions or illustrations given in general terms or listed within ranges of preference apply correspondingly to end products and to starting materials and intermediates. These radical definitions can be combined with one another as desired, i.e. including combinations between the respective ranges of preference.

Preference is given in accordance with the invention to using compounds of the formula (Ia) or (Ib) in which there is a combination of the definitions listed above as being preferred.

Particular preference is given in accordance with the invention to using compounds of the formula (Ia) or (Ib) in which there is a combination of the definitions listed above as being more preferred.

Very particular preference is given in accordance with the invention to using compounds of the formula (Ia) or (Ib) in which there is a combination of the definitions listed above as being even more preferred.

In particular, in accordance with the invention, compounds of the formula (Ia) or (Ib) in which there is a combination of the definitions listed above as particular definitions are used.

Especially, in accordance with the invention, compounds of the formula (Ia) or (Ib) in which there is a combination of the definitions listed above as especial definitions are used.

The compounds of the formulae (Ia) or (Ib) according to the invention can be obtained by the processes shown in the following schemes:

Process A

The compounds of the formula (Ia) in which Q is Q1, Q2, Q3, Q4, Q5, Q6, Q7, Q8, Q9, Q14 or Q15 can, when ⫝̸ represents exclusively double bonds, Aa is $C(R^{10})$, Ab is $C(R^{11})$, Ac is $C(R^{12})$ and Ad is $C(R^{13})$, be prepared by known methods as described in Scheme 1 below.

Scheme 1

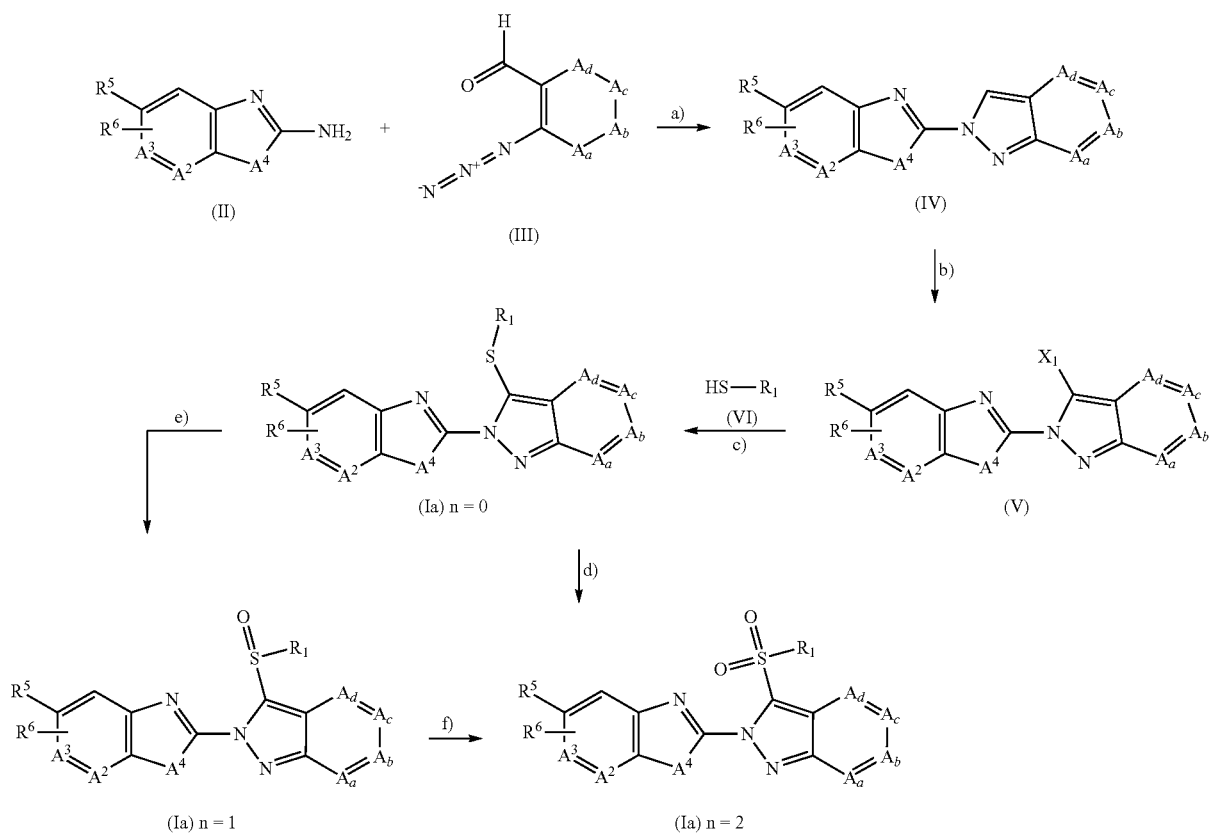

Compounds of the formula (Ia) in which Q is Q10, Q11, Q12 or Q13 are prepared in an entirely analogous manner.

Step a)

The compounds of the formula (IV) can be prepared by reacting the compounds of the formula (II) and (III) (US2009/18132 A1, 2009; U.S. Pat. No. 3,966,760 A1, 1976; Chemical Communications, 2011, 47, 10133).

Compounds of the formula (III) are either commercially available or can be prepared by known processes. In this regard, see, for example, US2012/214837 A1, 2012, WO2015/116882 A1, 2015, Journal of Organic Chemistry, 1995, vol. 60, #7 p. 2254-2256.

Compounds of the formula (II) are either commercially available or can be prepared by known processes. In this regard, see, for example, Bioorganic and medicinal chemistry letters, 2002, vol. 12, #16 p. 2221-2224, WO2011/71725 A1, 2011, US2016/31875 A1, 2016 or, for example, WO2010/19899 A1, 2010, Journal of Medicinal Chemistry, 1999, vol. 42, #1 p. 50-59

The formation of the imine intermediate is promoted by dehydrating additions, for example molecular sieve. Suitable catalysts are Brønsted and Lewis acids, for example acetic acid and tetraisopropyl orthotitanate. The cyclization can be accelerated by addition of copper salts such as CuI and amine ligands such as N,N,N',N-tetramethylethylenediamine.

The conversion to the compound of the formula (IV) can be carried out neat or in a solvent, preference being given to conducting the reaction in a solvent selected from customary solvents that are inert under the prevailing reaction conditions. Preference is given to high-boiling solvents such as dimethylformamide or toluene.

The reaction can be conducted under reduced pressure, at standard pressure or under elevated pressure, and at temperatures of 0° C. to 200° C.

Compound II, in the case that Q=Q1, can be prepared by known methods. In this regard, see, for example, European Journal of Medicinal Chemistry, 2014, vol. 78, p. 35-42. It is also possible in an entirely analogous manner to prepare compound IIa in the case that Q=Q15.

Compound II, in the case that Q=Q2, can be prepared by known methods. In this regard, see, for example, Journal of Heterocyclic Chemistry, 1995, vol. 32, #2 p. 467-471. It is also possible in an entirely analogous manner to prepare compound II in the case that Q=Q14. With regard to the preparation of pyridazine precursors for Q14, see also WO2016/039411.

Compound II, in the case that Q=Q3, can be prepared by known methods. In this regard, see, for example, Journal of Heterocyclic Chemistry, 1997, vol. 34, #3 p. 717-727.

Compound II, in the case that Q=Q4, can be prepared by known methods. In this regard, see, for example, WO2013/23184 A1, 2013.

Compound II, in the case that Q=Q5, can be prepared by known methods. In this regard, see, for example, WO2009/147431 A1, 2009. It is also possible in an entirely analogous manner to prepare compound II in the case that Q=Q6.

Compound II, in the case that Q=Q7, can be prepared by known methods. In this regard, see, for example, Synlett, 2016, vol. 27, #12 art. no. ST-2015-B0983-L, p. 1798-1802.

Compound II, in the case that Q=Q8, can be prepared by known methods. In this regard, see, for example, Chemical and pharmaceutical bulletin, 1979, vol. 27, #2 p. 410-418. It is also possible in an entirely analogous manner to prepare compound IIa in the case that Q=Q9.

Compound II, in the case that Q=Q10, can be prepared by known methods. In this regard, see, for example, WO2010/19899 A1, 2010.

Compound II, in the case that Q=Q11, can be prepared by known methods. In this regard, see, for example, WO2009/10530 A1, 2009.

Compound II, in the case that Q=Q12, can be prepared by known methods. In this regard, see, for example, WO2005/89763 A1, 2005. It is also possible in an entirely analogous manner to prepare compound II in the case that Q=Q13.

Step b)

The compounds of the formula (V) where $X^1$ may be F, Cl or Br are prepared analogously to commonly known conditions with the aid of an appropriate halogenating reagent. Suitable halogenating reagents are, for example, N-chlorosuccinimide ($X^1$=Cl), N-bromosuccinimide, bromine ($X^1$=Br).

The conversion to the compound of the formula (V) can be carried out neat or in a solvent, preference being given to conducting the reaction in a solvent selected from customary solvents that are inert under the prevailing reaction conditions. Preference is given to solvents such as tetrachloromethane, tetrahydrofuran, acetic acid, for example.

The reaction can be conducted under reduced pressure, at standard pressure or under elevated pressure, and at temperatures of 0° C. to 200° C.

Step c)

The compounds of the formula (Ia) where n is 0 can be prepared by reacting the compounds of the formula (V) with the compounds of the formula (VI) in the presence of a base.

Mercaptan derivatives of the formula (VI), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications 13, 2000, 1163-1164 or Journal of the American Chemical Society, 44, 1922, 1329.

The conversion to the compound of the formula (Ia) where n is 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are inorganic bases from the group consisting of acetates, phosphates, hydrogencarbonates and carbonates of alkali metals or alkaline earth metals. Preference is given to caesium carbonate, sodium carbonate, potassium carbonate and sodium hydrogencarbonate. Further suitable bases are alkali metal hydrides, for example sodium hydride.

The reaction can be conducted under reduced pressure, at standard pressure or under elevated pressure, and at temperatures of 0° C. to 200° C.

In the reaction described, $X^1$ is preferably a fluorine or chlorine atom.

If $X^1$ is bromine, an alternative option is transmetallation with a suitable lithium base, followed by reaction with the appropriate commercially available disulfide. In this regard, see Bioorganic and Medicinal Chemistry Letters, 20 (2010), 2770-2775.

Suitable lithium bases are, for example, n-butyllithium.

The conversion to the compound of the formula (Ia) where n is 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether.

The reaction can be conducted under reduced pressure, at standard pressure or under elevated pressure, and at temperatures of 0° C. to 200° C.

The reaction can be conducted in the microwave.

Step d)

The compounds of the formula (Ia) where n is 1 can be prepared by oxidizing the compounds of the formula (Ia) where n is 0. The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Step e)

The compounds of the formula (Ia) where n is 2 can be prepared by oxidizing the compounds of the formula (Ia) where n is 1. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step f)

The compounds of the formula (Ia) where n is 2 can also be prepared in a one-step process by oxidizing the compounds of the formula (Ia) where n is 0. The oxidation is generally carried out in a solvent.

Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Process B:

The compounds of the formula (Ib) in which Q is Q1, Q2, Q3, Q4, Q5, Q6, Q7, Q8, Q9, Q14, Q15 can be prepared by known methods as described in Scheme 2 below.

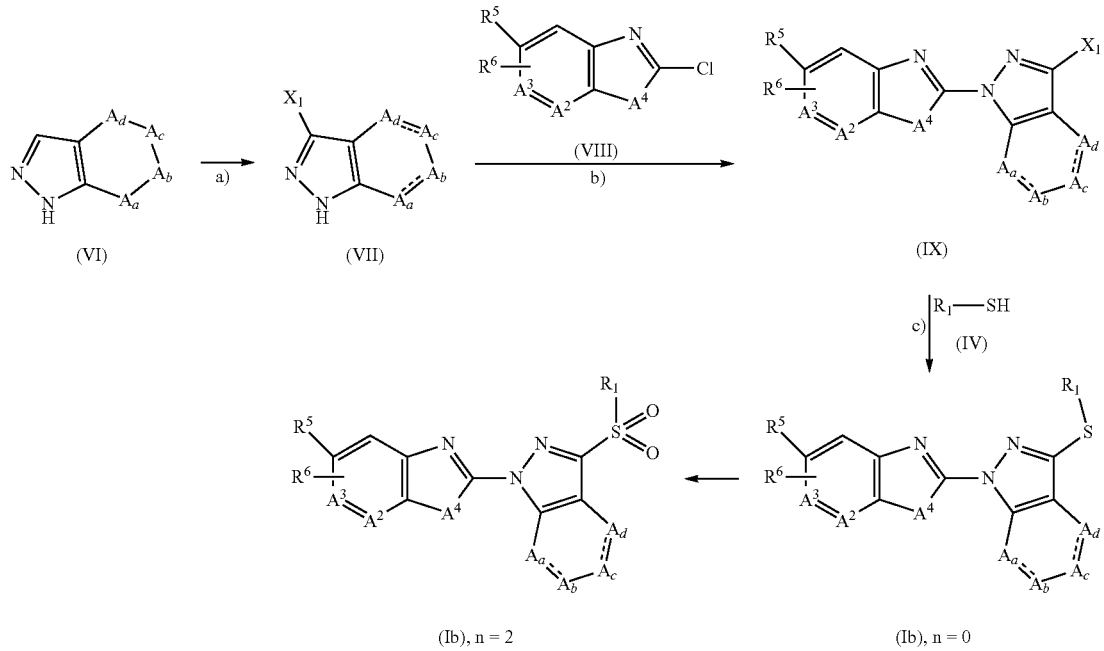

Scheme 2

(VI) (VII) (VIII) (IX) (Ib), n = 2 (Ib), n = 0

Compounds of the formula (Ib) in which Q is Q10, Q11, Q12, Q13 are prepared in an entirely analogous manner.

Step a)

The compounds of the formula (VII) where $X^1$ may be F, Cl, Br or iodine are prepared analogously to commonly known conditions with the aid of an appropriate halogenating reagent. Suitable halogenating reagents are, for example, N-chlorosuccinimide ($X^1$=Cl), N-bromosuccinimide, bromine ($X^1$=Br) or iodine/KOH ($X^1$=I).

The conversion to the compound of the formula (VII) can be carried out neat or in a solvent, preference being given to conducting the reaction in a solvent selected from customary solvents that are inert under the prevailing reaction conditions. Preference is given to using solvents such as tetrachloromethane, tetrahydrofuran, acetic acid, for example.

The reaction can be conducted under reduced pressure, at standard pressure or under elevated pressure, and at temperatures of 0° C. to 200° C.

Step b)

The compound of the formula (IX) is prepared as described, for example, in WO2009/134750 A1, by reaction of compound (VII) with compound (VIII) in the presence of a base. Suitable bases are, for example, sodium hydride, caesium carbonate, potassium carbonate or triethylamine.

The conversion to the compound of the formula (IX) can be carried out neat or in a solvent, preference being given to conducting the reaction in a solvent selected from customary solvents that are inert under the prevailing reaction conditions. Preference is given to solvents such as dimethylformamide, for example.

The reaction can be conducted under reduced pressure, at standard pressure or under elevated pressure, and at temperatures of 0° C. to 200° C.

Compound (VIII) can, if Q=Q1, Q2, Q3, Q4, Q5, Q6, Q7, Q8, Q9, Q14, Q15, be prepared by various universal processes. In this regard, see, for example, WO2009/134750 A1, 2009 or Organic and Biomolecular Chemistry, 2007, vol. 5, #16 p. 2567-2571 or WO2006/116412 A2, 2006

Compound (VIII) can, if Q=Q10, Q11, Q12, Q13, Q15, be prepared by various universal processes. In this regard, see, for example, WO2013/59928 A1, 2013, EP1466527 A1, 2004; KR2016/1508 A, 2016

Step c)

If $X^1$=Br or I, compound (IX) can be converted to (Ib), n=0, by reaction with compound (IV) in the presence of a palladium catalyst and a base. A suitable palladium catalyst is, for example, the combination of $Pd_2(dba)_3$ with Xantphos as ligand. A suitable base is diisopropylethylamine.

If $X^1$=F, Cl, compound (IX) can be converted to (Ib) where n is 0 by reaction with compound (IV) and a strong base. Examples of suitable bases are inorganic bases from the group consisting of acetates, phosphates, hydrogencarbonates and carbonates of alkali metals or alkaline earth metals. Preference is given to caesium carbonate, sodium carbonate, potassium carbonate and sodium hydrogencarbonate. Further suitable bases are alkali metal hydrides, for example sodium hydride.

The conversion to the compound of the formula (Ib) where n is 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Step d)

The compounds of the formula (Ib) where n is 2 or 1 can be prepared by oxidizing the compounds of the formula (Ib) where n is 0. The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Process C

The compounds of the formula (Ia) in which Q is Q1, Q2, Q3, Q4, Q5, Q6, Q7, Q8, Q9, Q14 or Q15, when ⚍ represents exclusively single bonds, Aa is $C(R^{10})(R^{14})$, Ab is $C(R^{11})(R^{15})$, Ac is $C(R^{12})(R^{16})$ and Ad is $C(R^{13})(R^{17})$, can be prepared by known methods as described in Scheme 3 below.

Compounds of the formula (Ia) in which Q is Q10, Q11, 12 or 13 are prepared in an entirely analogous manner.

Step a)

Compound (XI) is commercially available or can be prepared by known methods by cyclization of compound (X) with hydrazine. In this regard, see, for example, US 2015/0225397 A1.

Compound (X) is commercially available or can be prepared by known methods from the corresponding cyclohexanone. In this regard, see, for example, Tetrahedron, 1984, vol. 40, p. 1051 or Journal of Organic Chemistry, 2006, vol. 71, #16 p. 6149-6156.

Step b)

Compounds of the formula (XII) are prepared analogously to commonly known conditions by coupling of compound (VIII) with compounds (XI) in the presence of a base; see WO2009/134750. A suitable base is, for example,

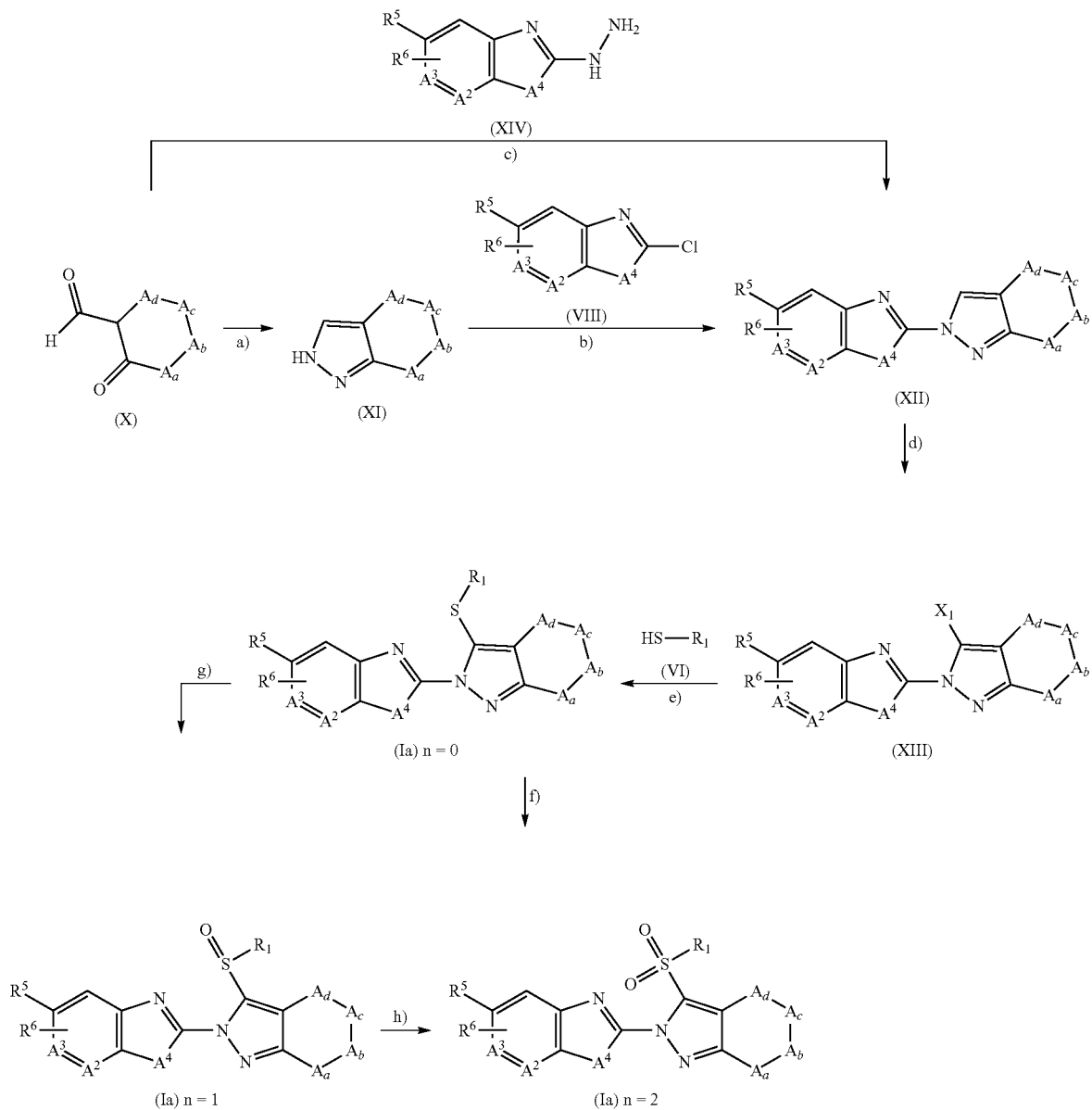

caesium carbonate and further alkali metal carbonates. The conversion to the compound of the formula (XII) can be carried out neat or in a solvent, preference being given to conducting the reaction in a solvent selected from customary solvents that are inert under the prevailing reaction conditions. Preference is given to solvents such as dimethylformamide, for example.

Compound (VIII) can, if Q=Q1, Q2, Q3, Q4, Q5, Q6, Q7, Q8, Q9, Q14, Q15, be prepared by various universal processes. In this regard, see, for example, WO2009/134750 A1, 2009 or Organic and Biomolecular Chemistry, 2007, vol. 5, #16 p. 2567-2571 or WO2006/116412 A2, 2006

Compound (VIII) can, if Q=Q10, Q11, Q12, Q13, Q15, be prepared by various universal processes. In this regard, see, for example, WO2013/59928 A1, 2013, EP1466527 A1, 2004; KR2016/1508 A, 2016

Step c)

As an alternative to the two-stage sequence of step a) and step b), compound (XII) can also be obtained in one stage from compound (X) and compound (XIV). The reaction is typically effected under acid catalysis. Suitable acids are, for example, sulfuric acid, hydrochloric acid, acetic acid or toluenesulfonic acid. As an example see, inter alia, Indian Journal of Chemistry, Section B: Organic Chemistry Including Medicinal Chemistry, 1991, vol. 30, #3 p. 306-312 or Justus Liebigs Annalen der Chemie, 1927, vol. 453, p. 228

If Q=Q1, Q2, Q3, Q4, Q5, Q6, Q7, Q8, Q9, Q14, Q15, the starting material (XIV) can be obtained by reaction with hydrazine from the corresponding halide (VIII). In this regard, see, for example, Bioorganic Chemistry, 2015, vol. 60, p. 19-29 or WO2009/134750 A1, 2009

If Q=Q10, Q11, Q12, Q13, the starting material (XIV) can be obtained, for example, as described in European Journal of Medicinal Chemistry, 2014, vol. 75, p. 492-500 or Arzneimittel-Forschung/Drug Research, 1977, vol. 27, #1 p. 82-89.

Step d)

Compounds of the formula (XIII) where $X^1$ may be F, Cl or Br are prepared analogously to commonly known conditions with the aid of an appropriate halogenating reagent. Suitable halogenating reagents are, for example, N-chlorosuccinimide ($X^1$=Cl), N-bromosuccinimide, bromine ($X^1$=Br).

The conversion to the compound of the formula (XIII) can be carried out neat or in a solvent, preference being given to conducting the reaction in a solvent selected from customary solvents that are inert under the prevailing reaction conditions. Preference is given to solvents such as tetrachloromethane, tetrahydrofuran, acetic acid, for example.

The reaction can be conducted under reduced pressure, at standard pressure or under elevated pressure, and at temperatures of 0° C. to 200° C.

Step e)

The compounds of the formula (Ia) where n is 0 can be prepared by reacting the compounds of the formula (XIII) with the compounds of the formula (VI) in the presence of a base.

Mercaptan derivatives of the formula (VI), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications 13, 2000, 1163-1164 or Journal of the American Chemical Society, 44, 1922, 1329.

The conversion to the compound of the formula (Ia) where n is 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are inorganic bases from the group consisting of acetates, phosphates, hydrogencarbonates and carbonates of alkali metals or alkaline earth metals. Preference is given to caesium carbonate, sodium carbonate, potassium carbonate and sodium hydrogencarbonate. Further suitable bases are alkali metal hydrides, for example sodium hydride.

The reaction can be conducted under reduced pressure, at standard pressure or under elevated pressure, and at temperatures of 0° C. to 200° C.

In the reaction described, $X^1$ is preferably a fluorine or chlorine atom.

If $X^1$ is bromine, an alternative option is transmetallation with a suitable lithium base, followed by reaction with the appropriate commercially available disulfide. In this regard see Bioorganic and Medicinal Chemistry Letters, 20 (2010), 2770-2775.

Suitable lithium bases are, for example, n-butyllithium.

The conversion to the compound of the formula (Ia) where n is 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether.

The reaction can be conducted under reduced pressure, at standard pressure or under elevated pressure, and at temperatures of 0° C. to 200° C.

The reaction can be conducted in the microwave.

Step f)

The compounds of the formula (Ia) where n is 1 can be prepared by oxidizing the compounds of the formula (Ia) where n is 0. The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Step g)

The compounds of the formula (Ia) where n is 2 can be prepared by oxidizing the compounds of the formula (Ia) where n is 1. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step h)

The compounds of the formula (Ia) where n is 2 can also be prepared in a one-step process by oxidizing the compounds of the formula (Ia) where n is 0. The oxidation is generally carried out in a solvent.

Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Methods and Uses

Hereinafter, the term "formula (I)" is synonymous with formula (Ia) and formula (Ib).

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection compositions.

In the context of the present application, the term "pesticide" in each case also always encompasses the term "crop protection composition".

The compounds of the formula (I), given good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The abovementioned pests include:

pests from the phylum of the Arthropoda, in particular from the class of the Arachnida e.g. *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda e.g. *Geophilus* spp., *Scutigera* spp.;

from the order or the class of the Collembola e.g. *Onychiurus armatus; Sminthurus viridis*; from the class of the Diplopoda e.g. *Blaniulus guttulatus;* from the class of the Insecta, for example from the order of the Blattodea e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera e.g. *Acalymma vittatum, Acanthoscelides obtectus, Adoretus* spp., *Aethina tumida, Agelastica alni, Agrilus* spp., e.g. *Agrilus planipennis, Agrilus coxalis, Agrilus bilineatus, Agrilus anxius, Agriotes* spp., e.g. *Agriotes linneatus, Agriotes mancus, Alphitobius diaperinus, Amphimallon solstitialis, Anobium punctatum, Anoplophora* spp., e.g. *Anoplophora glabripennis, Anthonomus* spp., e.g. *Anthonomus grandis, Anthrenus* spp., *Apion* spp., *Apogonia* spp., *Atomaria* spp., e.g. *Atomaria linearis, Attagenus* spp., *Baris caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conoderus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dendroctonus* spp., e.g. *Dendroctonus ponderosae, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., e.g. *Epilachna borealis, Epilachna varivestis, Epitrix* spp., e.g. *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., e.g. *Leucoptera coffeella, Lissorhoptrus oryzophilus, Listronotus (=Hyperodes)* spp., *Lixus* spp., *Luperodes* spp., *Luperomorpha xanthodera, Lyctus* spp., *Megacyllene* spp., e.g. *Megacyllene robiniae, Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., e.g. *Scolytus multistriatus, Sinoxylon perforans, Sitophilus* spp., e.g. *Sitophilus granarius, Sitophilus linearis, Sitophilus oryzae, Sitophilus zeamais, Sphenophorus* spp., *Stegobium paniceum, Sternechus* spp., e.g. *Sternechus paludatus, Symphyletes* spp., *Tanymecus* spp., e.g. *Tanymecus dilaticollis, Tanymecus indicus, Tanymecus palliatus, Tenebrio molitor, Tenebrioides mauretanicus, Tribolium* spp., e.g. *Tribolium audax, Tribolium castaneum, Tribolium confusum, Trogoderma* spp., *Tychius* spp., *Xylotrechus* spp., *Zabrus* spp., e.g. *Zabrus tenebrioides;* from the order of the Dermaptera e.g. *Anisolabis maritime, Forficula auricularia, Labidura riparia;* from the order of the Diptera e.g. *Aedes* spp., e.g. *Aedes aegypti, Aedes albopictus, Aedes sticticus, Aedes vexans, Agromyza* spp., e.g. *Agromyza frontella, Agromyza parvicornis, Anastrepha* spp., *Anopheles* spp., e.g. *Anopheles quadrimaculatus, Anopheles gambiae, Asphondylia* spp., *Bactrocera* spp., e.g. *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., e.g. *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., e.g. *Culex pipiens, Culex quinquefasciatus, Culicoides* spp., *Culiseta* spp., *Cuterebra* spp., *Dacus oleae, Dasineura* spp., e.g. *Dasineura brassicae, Delia* spp., e.g. *Delia antiqua, Delia coarctata, Delia florilega, Delia platura, Delia radicum, Dermatobia hominis, Drosophila* spp., e.g. *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., e.g. *Liriomyza brassicae, Liriomyza huidobrensis, Liriomyza sativae, Lucilia* spp., e.g. *Lucilia cuprina, Lutzomyia* spp., *Mansonia* spp., *Musca* spp., e.g. *Musca domestica, Musca domestica vicina, Oestrus* spp., *Oscinella frit, Paratanytarsus* spp., *Paralauterborniella subcincta, Pegomya* or *Pegomyia* spp., e.g. *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., e.g. *Rhagoletis cingulata, Rhagoletis completa, Rhagoletis fausta, Rhagoletis indifferens, Rhagoletis mendax, Rhagoletis pomonella, Sarcophaga* spp., *Simulium* spp., e.g. *Simulium meridionale, Stomoxys* spp., *Tabanus* spp., *Tetanops* spp., *Tipula* spp., e.g. *Tipula paludosa, Tipula simplex, Toxotrypana curvicauda;* from the order of the Hemiptera e.g. *Acizzia acaciaebaileyanae, Acizzia dodonaeae, Acizzia uncatoides, Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inornata, Aphanostigma piri, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca*

*maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., e.g. *Icerya purchasi, Idiocerus* spp., *Idioscopus* spp., *Laodelphax striatellus, Lecanium* spp., e.g. *Lecanium corni* (=*Parthenolecanium corni*), *Lepidosaphes* spp., e.g. *Lepidosaphes ulmi, Lipaphis erysimi, Lopholeucaspis japonica, Lycorma delicatula, Macrosiphum* spp., e.g. *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., e.g. *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., e.g. *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., e.g. *Paratrioza cockerelli, Parlatoria* spp., *Pemphigus* spp., e.g. *Pemphigus bursarius, Pemphigus populivenae, Peregrinus maidis, Perkinsiella* spp., *Phenacoccus* spp., e.g. *Phenacoccus madeirensis, Phloeomyzus passerinii, Phorodon humuli, Phylloxera* spp., e.g. *Phylloxera devastatrix, Phylloxera notabilis, Pinnaspis aspidistrae, Planococcus* spp., e.g. *Planococcus citri, Prosopidopsylla flava, Protopulvinaria pyriformis, Pseudaulacaspis pentagona, Pseudococcus* spp., e.g. *Pseudococcus calceolariae, Pseudococcus comstocki, Pseudococcus longispinus, Pseudococcus maritimus, Pseudococcus viburni, Psyllopsis* spp., *Psylla* spp., e.g. *Psylla buxi, Psylla mali, Psylla pyri, Pteromalus* spp., *Pulvinaria* spp., *Pyrilla* spp., *Quadraspidiotus* spp., e.g. *Quadraspidiotus juglansregiae, Quadraspidiotus ostreaeformis, Quadraspidiotus perniciosus, Quesada gigas, Rastrococcus* spp., *Rhopalosiphum* spp., e.g. *Rhopalosiphum maidis, Rhopalosiphum oxyacanthae, Rhopalosiphum padi, Rhopalosiphum rufiabdominale, Saissetia* spp., e.g. *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., e.g. *Toxoptera aurantii, Toxoptera citricidus, Trialeurodes vaporariorum, Trioza* spp., e.g. *Trioza diospyri, Typhlocyba* spp., *Unaspis* spp., *Viteus vitifolii, Zygina* spp.;

from the suborder of the Heteroptera e.g. *Aelia* spp., *Anasa tristis, Antestiopsis* spp., *Boisea* spp., *Blissus* spp., *Calocoris* spp., *Campylomma livida, Cavelerius* spp., *Cimex* spp., e.g. *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., e.g. *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., e.g. *Lygocoris pabulinus, Lygus* spp., e.g. *Lygus elisus, Lygus hesperus, Lygus lineolaris, Macropes excavatus, Megacopta cribraria, Miridae,* *Monalonion atratum, Nezara* spp., e.g. *Nezara viridula, Nysius* spp., *Oebalus* spp., *Pentomidae, Piesma quadrata, Piezodorus* spp., e.g. *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera e.g. *Acromyrmex* spp., *Athalia* spp., e.g. *Athalia rosae, Atta* spp., *Camponotus* spp., *Dolichovespula* spp., *Diprion* spp., e.g. *Diprion similis, Hoplocampa* spp., e.g. *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., e.g. *Sirex noctilio, Solenopsis invicta, Tapinoma* spp., *Technomyrmex albipes, Urocerus* spp., *Vespa* spp., e.g. *Vespa crabro, Wasmannia auropunctata, Xeris* spp.;

from the order of the Isopoda e.g. *Armadillidium vulgare, Oniscus asellus, Porcellio scaber;* from the order of the Isoptera e.g. *Coptotermes* spp., e.g. *Coptotermes formosanus, Cornitermes cumulans, Cryptotermes* spp., *Incisitermes* spp., *Kalotermes* spp., *Microtermes obesi, Nasutitermis* spp., *Odontotermes* spp., *Porotermes* spp., *Reticulitermes* spp., e.g. *Reticulitermes flavipes, Reticulitermes hesperus;* from the order of the Lepidoptera e.g. *Achroia grisella, Acronicta major, Adoxophyes* spp., e.g. *Adoxophyes orana, Aedia leucomelas, Agrotis* spp., e.g. *Agrotis segetum, Agrotis ipsilon, Alabama* spp., e.g. *Alabama argillacea, Amyelois transitella, Anarsia* spp., *Anticarsia* spp., e.g. *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., e.g. *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., e.g. *Cydia nigricana, Cydia pomonella, Dalaca noctuides, Diaphania* spp., *Diparopsis* spp., *Diatraea saccharalis, Dioryctria* spp., e.g. *Dioryctria zimmermani, Earias* spp., *Ecdytolopha aurantium, Elasmopalpus lignosellus, Eldana saccharina, Ephestia* spp., e.g. *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., e.g. *Euproctis chrysorrhoea, Euxoa* spp., *Feltia* spp., *Galleria mellonella, Gracillaria* spp., *Grapholitha* spp., e.g. *Grapholita molesta, Grapholita prunivora, Hedylepta* spp., *Helicoverpa* spp., e.g. *Helicoverpa armigera, Helicoverpa zea, Heliothis* spp., e.g. *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., e.g. *Leucoptera coffeella, Lithocolletis* spp., e.g. *Lithocolletis blancardella, Lithophane antennata, Lobesia* spp., e.g. *Lobesia botrana, Loxagrotis albicosta, Lymantria* spp., e.g. *Lymantria dispar, Lyonetia* spp., e.g. *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., e.g. *Ostrinia nubilalis, Panolis flammea, Parnara* spp., *Pectinophora* spp., e.g. *Pectinophora gossypiella, Perileucoptera* spp., *Phthorimaea* spp., e.g. *Phthorimaea operculella, Phyllocnistis citrella, Phyllonorycter* spp., e.g. *Phyllonorycter blancardella, Phyllonorycter crataegella, Pieris* spp., e.g. *Pieris* rapae, Platynota stultana, Plodia interpunctella, Plusia spp., Plutella xylostella (=Plutella maculipennis), Podesia spp., e.g. Podesia syringae, Prays spp., Prodenia spp., Protoparce spp., Pseudaletia spp., e.g. Pseudaletia unipuncta, Pseudoplusia includens, Pyrausta nubilalis, Rachiplusia nu, Schoenobius spp., e.g. Schoenobius bipunctifer, Scirpophaga spp., e.g. Scirpophaga innotata, Scotia segetum, Sesamia spp., e.g. Sesamia inferens, Sparganothis spp., Spodoptera spp., e.g. Spodoptera eradiana, Spodoptera exigua, Spodoptera frugiperda, Spodoptera praefica, Stathmopoda spp., Stenoma spp., Stomopteryx subsecivella, Synanthedon spp., Tecia solanivora, Thaumetopoea spp., Thermesia gemmatalis, Tinea cloacella, Tinea pellionella, Tineola bisselliella, Tortrix spp., Trichophaga tapetzella, Trichoplusia spp., e.g. Trichoplusia ni, Tryporyza incertulas, Tuta absoluta, Virachola spp.;

from the order of the Orthoptera or Saltatoria e.g. Acheta domesticus, Dichroplus spp., Gryllotalpa spp., e.g. Gryllotalpa gryllotalpa, Hieroglyphus spp., Locusta spp., e.g. Locusta migratoria, Melanoplus spp., e.g. Melanoplus devastator, Paratlanticus ussuriensis, Schistocerca gregaria;

from the order of the Phthiraptera e.g. Damalinia spp., Haematopinus spp., Linognathus spp., Pediculus spp., Phylloxera vastatrix, Phthirus pubis, Trichodectes spp.;

from the order of the Psocoptera e.g. Lepinotus spp., Liposcelis spp.;

from the order of the Siphonaptera e.g. Ceratophyllus spp., Ctenocephalides spp., e.g. Ctenocephalides canis, Ctenocephalides felis, Pulex irritans, Tunga penetrans, Xenopsylla cheopis;

from the order of the Thysanoptera e.g. Anaphothrips obscurus, Baliothrips biformis, Chaetanaphothrips leeuweni, Drepanothrips reuteri, Enneothrips flavens, Frankliniella spp., e.g. Frankliniella fusca, Frankliniella occidentalis, Frankliniella schultzei, Frankliniella tritici, Frankliniella vaccinii, Frankliniella williamsi, Haplothrips spp., Heliothrips spp., Hercinothrips femoralis, Kakothrips spp., Rhipiphorothrips cruentatus, Scirtothrips spp., Taeniothrips cardamomi, Thrips spp., e.g. Thrips palmi, Thrips tabaci;

from the order of the Zygentoma (=Thysanura), e.g. Ctenolepisma spp., Lepisma saccharina, Lepismodes inquilinus, Thermobia domestica;

from the class of the Symphyla e.g. Scutigerella spp., e.g. Scutigerella immaculata;

pests from the phylum of the Mollusca, e.g. from the class of the Bivalvia, e.g. Dreissena spp.; and from the class of the Gastropoda e.g. Arion spp., e.g. Arion ater rufus, Biomphalaria spp., Bulinus spp., Deroceras spp., e.g. Deroceras laeve, Galba spp., Lymnaea spp., Oncomelania spp., Pomacea spp., Succinea spp.;

plant pests from the phylum of the Nematoda, i.e. phytoparasitic nematodes, in particular Aglenchus spp., e.g. Aglenchus agricola, Anguina spp., e.g. Anguina tritici, Aphelenchoides spp., e.g. Aphelenchoides arachidis, Aphelenchoides fragariae, Belonolaimus spp., e.g. Belonolaimus gracilis, Belonolaimus longicaudatus, Belonolaimus nortoni, Bursaphelenchus spp., e.g. Bursaphelenchus cocophilus, Bursaphelenchus eremus, Bursaphelenchus xylophilus, Cacopaurus spp., e.g. Cacopaurus pestis, Criconemella spp., e.g. Criconemella curvata, Criconemella onoensis, Criconemella ornata, Criconemella rusium, Criconemella xenoplax (=Mesocriconema xenoplax), Criconemoides spp., e.g. Criconemoides ferniae, Criconemoides onoense, Criconemoides ornatum, Ditylenchus spp., e.g. Ditylenchus dipsaci, Dolichodorus spp., Globodera spp., e.g. Globodera pallida, Globodera rostochiensis, Helicotylenchus spp., e.g. Helicotylenchus dihystera, Hemicriconemoides spp., Hemicycliophora spp., Heterodera spp., e.g. Heterodera avenae, Heterodera glycines, Heterodera schachtii, Hirschmaniella spp., Hoplolaimus spp., Longidorus spp., e.g. Longidorus africanus, Meloidogyne spp., e.g. Meloidogyne chitwoodi, Meloidogyne fallax, Meloidogyne hapla, Meloidogyne incognita, Meloinema spp., Nacobbus spp., Neotylenchus spp., Paralongidorus spp., Paraphelenchus spp., Paratrichodorus spp., e.g. Paratrichodorus minor, Paratylenchus spp., Pratylenchus spp., e.g. Pratylenchus penetrans, Pseudohalenchus spp., Psilenchus spp., Punctodera spp., Quinisulcius spp., Radopholus spp., e.g. Radopholus citrophilus, Radopholus similis, Rotylenchulus spp., Rotylenchus spp., Scutellonema spp., Subanguina spp., Trichodorus spp., e.g. Trichodorus obtusus, Trichodorus primitivus, Tylenchorhynchus spp., e.g. Tylenchorhynchus annulatus, Tylenchulus spp., e.g. Tylenchulus semipenetrans, Xiphinema spp., e.g. Xiphinema index.

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (Mycoplasma-like organisms) and RLO (Rickettsia-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active ingredients into plants. Penetrants are defined in this context by their ability to penetrate from the (generally aqueous) application liquor and/or from the spray coating into the cuticle of the plant and hence to increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active ingredients specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect midgut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins:

Cry1Ab, Cry1Ac, Cry1Fa, Cry1A.105, Cry2Ab, Vip3A, mCry3A, Cry3Ab, Cry3Bb, Cry34 Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active ingredients, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl) pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio] phenyl]amino]carbonyl]indeno[1,2-e][1,3,4]oxadiazine-4a (3H)-carboxylic acid methyl ester (known from CN 102391261 A) (CAS 1370358-69-2); 6-deoxy-3-O-ethyl-2, 4-di-O-methyl-1-[N-[4-[1-[4-(1,1,2,2,2-pentafluoroethoxy) phenyl]-1H-1,2,4-triazole-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9).

Fungicides

The active ingredients specified herein by their common name are known and described, for example, in "Pesticide Manual" (16th Ed. British Crop Protection Council) or on the internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5- dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1 S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3 S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (accession number CNCM 1-952).

Examples of viruses which are used or can be used as biological pesticides are:

*Adoxophyes orana* (summer fruit *Tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), pyrethrum/pyrethrins, *Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safener as mixing components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or nonprotectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active ingredients, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for the protection of seed of any plant variety which is used in agriculture, in greenhouses, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active ingredients. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of agrochemically active ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekäimpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., *Phtirus* spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sar-*

*cophaga* spp., *Simulium* spp., *Stomoxys* spp., *Tabanus* spp., *Tipula* spp., *Wilhelmia* spp., *Wohlfahrtia* spp.;

from the order of Siphonapterida, for example *Ceratophyllus* spp., *Ctenocephalides* spp., *Pulex* spp., *Tunga* spp., *Xenopsylla* spp.;

from the order of heteropterida, for example, *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (Acarina) and the order of Metastigmata, for example from the family of Argasidae, such as *Argas* spp., *Ornithodorus* spp., *Otobius* spp., from the family of Ixodidae, such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata, such as *Dermanyssus* spp., *Ornithonyssus* spp., *Pneumonyssus* spp., *Raillietia* spp., *Sternostoma* spp., *Tropilaelaps* spp., *Varroa* spp.; from the order of Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of Acaridida (Astigmata), for example *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example, *Giardia* spp., *Spironucleus* spp.

Parabasala: from the order of Trichomonadida, for example *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminthes (e.g. Monogenea, cestodes and trematodes).

Exemplary helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) for use as a medicament.

A further aspect relates to the compounds of the formula (I) for use as an antiendoparasitic agent.

A further specific aspect of the invention relates to the compounds of the formula (I) for use as an antithelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and preferably at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active ingredients, especially with endo- and ectoparasiticides, are provided for the field of veterinary medicine.

In the field of animal health, "mixture" means not just that two (or more) different active ingredients are formulated in a common formulation and are correspondingly employed together, but also relates to products comprising formulations separated for each active ingredient. Accordingly, when more than two active ingredients are to be employed, all active ingredients can be formulated in a common formulation or all active ingredients can be formulated in separate formulations; likewise conceivable are mixed forms in which some of the active ingredients are formulated together and some of the active ingredients are formulated separately. Separate formulations allow the separate or successive application of the active ingredients in question.

The active ingredients specified here by their "common names" are known and are described, for example, in the "Pesticide Manual" (see above) or can be searched for on the Internet (e.g.: http://www.alanwood.net/pesticides).

Illustrative active ingredients from the group of the ectoparasiticides as mixing components include, without any intention that this should constitute a restriction, the insecticides and acaricides listed in detail above. Further usable active ingredients are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active ingredients having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive varroa acaricides, for example organic acids, e.g. formic acid, oxalic acid.

Illustrative active ingredients from the group of the endoparasiticides, as mixing components, include, but are not limited to, active anthelmintic ingredients and active antiprotozoic ingredients.

The anthelmintically active ingredients include but are not limited to the following nematicidally, trematicidally and/or cestocidally active ingredients:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole; from the class of the depsipeptides, preferably cyclic depsipeptides, especially 24-membered cyclic depsipeptides, for example: emodepside, PF1022A;

from the class of the tetrahydropyrimidines, for example: morantel, pyrantel, oxantel; from the class of the imidazothiazoles, for example: butamisole, levamisole, tetramisole; from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophene, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel; from the class of the piperazines, for example: piperazine, hydroxyzine;

from the class of the tetracyclines, for example: tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Active antiprotozoic ingredients include, but are not limited to, the following active ingredients:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquine;

from the class of the pyrimidines, for example: pyrimethamine;

from the class of the sulfonamides, for example: sulfaquinoxaline, trimethoprim, sulfaclozin;

from the class of the thiamines, for example: amprolium;

from the class of the lincosamides, for example: clindamycin;

from the class of the carbanilides, for example: imidocarb;

from the class of the nitrofurans, for example: nifurtimox;

from the class of the quinazolinone alkaloids, for example: halofuginone;

from various other classes, for example: oxamniquin, paromomycin;

from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:

1) Mosquitoes

*Anopheles*: malaria, filariasis;

*Culex*: Japanese encephalitis, filariasis, other viral diseases, transmission of other worms;

*Aedes*: yellow fever, dengue fever, further viral disorders, filariasis;

Simuliidae: transmission of worms, especially *Onchocerca volvulus*;
Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borrelioses such as *Borrelia bungdorferi sensu lato., Borrelia duttoni*, tick-borne encephalitis, Q fever (*Coxiella burnetii*), babesioses (*Babesia canis canis*), ehrlichiosis.

Examples of vectors in the context of the present invention are insects, for example aphids, flies, leafhoppers or *Thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

Methods:

The determination of the M+ by LC-MS in the acidic range was carried out at pH 2.7 using the mobile phases 0.1% aqueous formic acid and acetonitrile (contains 0.1% formic acid); linear gradient from 10% acetonitrile to 95% acetonitrile, instrument: Agilent 1100 LC system, Agilent MSD system, HTS PAL.

The determination of the M+ by LC-MS in the neutral range was carried out at pH 7.8 using the mobile phases 0.001 molar aqueous ammonium bicarbonate solution and acetonitrile; linear gradient from 10% acetonitrile to 95% acetonitrile.

The NMR data of selected examples are listed either in conventional form (δ values, multiplet splitting, number of hydrogen atoms) or as NMR peak lists.

In each case, the solvent in which the NMR spectrum was recorded is stated.

2-[6-Chloro-3-(ethylsulfonyl)-2H-indazol-2-yl]-3-methyl-6-(trifluoromethyl)-3H-imidazo[4,5-b]pyridine (Ex. I-1)

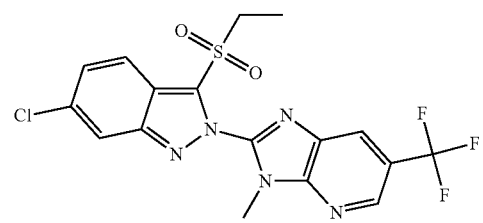 [SMILES: CCS(=O)(=O)c1c2ccc(Cl)cc2nn1-c1nc2cc(C(F)(F)F)cnc2n1C]

At room temperature, formic acid (122 mg, 2.9 mmol, 88%) and hydrogen peroxide (241 mg, 2.1 mmol, 30%) were added to 2-[6-chloro-3-(ethylsulfanyl)-2H-indazol-2-yl]-3-methyl-6-(trifluoromethyl)-3H-imidazo[4,5-b]pyridine (175 mg, 0.43 mmol) in dichloromethane (10 ml), and the mixture was stirred for 2 h. The reaction solution was diluted with ethyl acetate and washed with saturated sodium chloride solution. The organic phase was dried over sodium sulfate, filtered and then concentrated on a rotary evaporator. The residue was purified by column chromatography purification by means of preparative HPLC with a water/acetonitrile gradient as eluent.

MH+: 444; $^1$H-NMR (300 MHz, D6-DMSO) δ ppm: 9.01 (s, 1H), 8.85 (s, 1H), 8.22 (s, 1H), 8.10-8.07 (d, 1H), 7.59-7.55 (d, 1H), 3.97-3.88 (q, 2H), 3.83 (s, 3H), 1.31-1.26 (t, 3H).

2-[6-Chloro-3-(ethylsulfanyl)-2H-indazol-2-yl]-3-methyl-6-(trifluoromethyl)-3H-imidazo[4,5-b]pyridine (Ex. I-8)

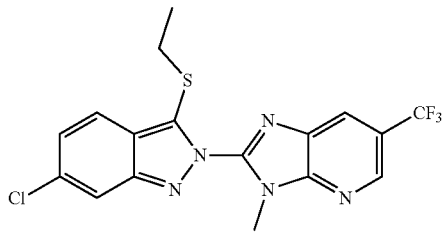 [SMILES: CCSc1c2ccc(Cl)cc2nn1-c1nc2cc(C(F)(F)F)cnc2n1C]

At room temperature, ethyl mercaptan (87 mg, 1.4 mmol), Pd$_2$(dba)$_3$ (36 mg, 0.035 mmol), Xantphos (40 mg, 0.069 mol) and N,N-diisopropylethylamine (270 mg, 2.1 mmol) were added to 2-(3-bromo-6-chloro-2H-indazol-2-yl)-3-methyl-6-(trifluoromethyl)-3H-imidazo[4,5-b]pyridine (300 mg, 0.69 mmol), dissolved in dioxane (8 ml), and the mixture was stirred overnight. The reaction solution was diluted with ethyl acetate and washed with saturated sodium chloride solution. The organic phase was dried over sodium sulfate, filtered and then concentrated on a rotary evaporator. The residue was purified by column chromatography purification by means of preparative HPLC with a water/acetonitrile gradient as eluent.

MH+: 412; $^1$H-NMR (300 MHz, D$_6$-DMSO) δ ppm: 8.97 (s, 1H), 8.81 (s, 1H), 8.00-7.93 (m, 2H), 7.34-7.30 (d, 1H), 3.83 (s, 3H), 3.06-3.03 (q, 2H), 1.13-1.08 (t, 3H).

2-(3-Bromo-6-chloro-2H-indazol-2-yl)-3-methyl-6-(trifluoromethyl)-3H-imidazo[4,5-b]pyridine

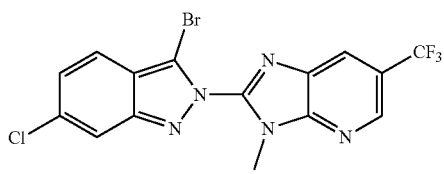 [SMILES: Cn1c(-n2nc3cc(Cl)ccc3c2Br)nc2cc(C(F)(F)F)cnc21]

2-(6-Chloro-2H-indazol-2-yl)-3-methyl-6-(trifluoromethyl)-3H-imidazo[4,5-b]pyridine (460 mg, 1.3 mmol) was dissolved in acetic acid (10 ml), and N-bromoacetamide (773 mg, 13 mmol) was added. The reaction solution was stirred at room temperature overnight. After the solvent had been removed on a rotary evaporator, the residue was purified by chromatography (SiO$_2$, eluent: ethyl acetate/pentane).

MH+: 432; $^1$H-NMR (300 MHz, D$_6$-DMSO) δ ppm: 8.98 (s, 1H), 8.83 (s, 1H), 8.00 (s, 1H), 7.80-7.77 (d, 1H), 7.33-7.30 (d, 1H), 3.91 (s, 3H), 2-(6-Chloro-2H-indazol-2-yl)-3-methyl-6-(trifluoromethyl)-3H-imidazo[4,5-b]pyridine

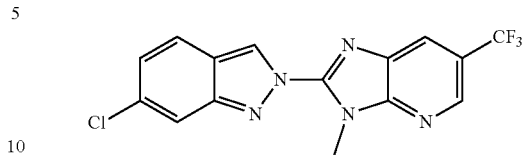

2-Azido-4-chlorobenzaldehyde (366 mg, 2.3 mmol) was dissolved in THF, and 3-methyl-6-(trifluoromethyl)-3H-imidazo[4,5-b]pyridin-2-amine (500 mg, 2.3 mmol) and tetraisopropyl titanate (787 mg, 2.3 mmol) were added. The reaction mixture was heated at 60° C. for 2 h. Then the solvent was distilled off and replaced by 10 ml of toluene. The reaction mixture was heated to 110° C. for a further 12 h. After the solvent had been removed, the residue was purified by chromatography (SiO$_2$, eluent: ethyl acetate/pentane).

MH+: 352; $^1$H-NMR (300 MHz, D$_6$-DMSO) δ ppm: 9.33 (s, 1H), 8.86 (s, 1H), 8.64 (s, 1H), 7.94-7.90 (m, 2H), 7.23-7.20 (m, 1H), 4.24 (s, 3H)

2-Azido-4-chlorobenzaldehyde

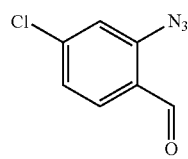 [SMILES: [N-]=[N+]=Nc1cc(Cl)ccc1C=O]

To a solution of 4-chloro-2-fluorobenzaldehyde (1 g, 6.3 mmol) in dimethylformamide (10 ml) was added sodium azide (620 mg, 10 mmol). The mixture was heated to 60° C. for 12 h. The reaction solution was diluted with water and then extracted with ethyl acetate. The combined organic extracts were washed with saturated sodium chloride solution and dried over sodium sulfate. After the solvent had been removed, the crude product was used in the subsequent reaction without further purification.

2-[5-Chloro-3-(ethylsulfonyl)-2H-indazol-2-yl]-3-methyl-6-(trifluoromethyl)-3H-imidazo[4,5-b]pyridine (Ex. I-2)

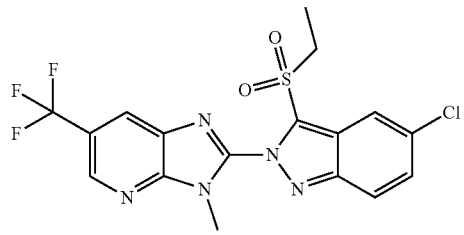 [SMILES: CCS(=O)(=O)c1c2cc(Cl)ccc2nn1-c1nc2cc(C(F)(F)F)cnc2n1C]

2-[5-Chloro-3-(ethylsulfanyl)-2H-indazol-2-yl]-3-methyl-6-(trifluoromethyl)-3H-imidazo[4,5-b]pyridine (150 mg, 0.36 mmol) was dissolved in dichloromethane (10 ml) and cooled to 0° C., and meta-chloroperbenzoic acid (178 mg, 1.0 mmol) was added. The reaction mixture was warmed to room temperature and stirred for a further 4 h. Then the solution was diluted with dichloromethane and washed with saturated sodium hydrogencarbonate solution. The organic phase was dried over sodium sulfate and concentrated on a rotary evaporator. The residue was purified by column chromatography purification by means of preparative HPLC with a water/acetonitrile gradient as eluent.

MH$^+$: 444; $^1$H-NMR (300 MHz, D$_6$-DMSO) δ ppm: 9.02 (s, 1H), 8.85 (s, 1H), 8.12-8.06 (m, 2H), 7.68-7.65 (m, 1H), 3.94-3.89 (q, 2H), 3.83 (s, 3H), 1.32-1.28 (t, 3H).

2-[5-Chloro-3-(ethylsulfanyl)-2H-indazol-2-yl]-3-methyl-6-(trifluoromethyl)-3H-imidazo[4,5-b]pyridine (Ex. I-9)

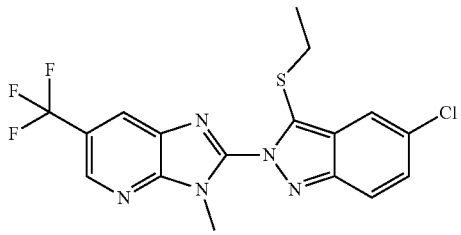 [SMILES: CCSc1c2cc(Cl)ccc2nn1-c1nc2cc(C(F)(F)F)cnc2n1C]

2-(3,5-Dichloro-2H-indazol-2-yl)-3-methyl-6-(trifluoromethyl)-3H-imidazo[4,5-b]pyridine (300 mg, 0.78 mmol) was dissolved in 1,4-dioxane (5 ml), and ethyl mercaptan (120 mg, 2.0 mmol), diisopropylethylamine (258 mg, 2.0 mmol), Pd$_2$(dba)$_3$CHCl$_3$ (55 mg, 0.05 mmol) and Xantphos (55 mg, 0.1 mmol) were added. The reaction mixture was heated at 110° C. for 4 h. After cooling to room temperature, the solution was washed with water and the aqueous phase was extracted twice with ethyl acetate. The combined organic extracts were dried over sodium sulfate and concentrated on a rotary evaporator. The residue was purified by column chromatography via preparative TLC (eluent: dichloromethane/pentane).

MH$^+$: 412; $^1$H-NMR (300 MHz, D$_6$-DMSO) δ ppm: 8.97 (s, 1H), 8.81 (s, 1H), 7.97-7.90 (m, 2H), 7.52-7.49 (d, 1H), 3.83 (s, 3H), 3.10-3.02 (q, 2H), 1.31-1.03 (t, 3H).

2-(3,5-Dichloro-2H-indazol-2-yl)-3-methyl-6-(trifluoromethyl)-3H-imidazo[4,5-b]pyridine

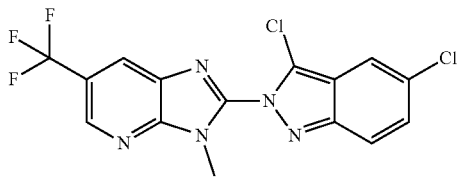 [SMILES: Cn1c(-n2nc3ccc(Cl)cc3c2Cl)nc2cc(C(F)(F)F)cnc21]

2-(5-Chloro-2H-indazol-2-yl)-3-methyl-6-(trifluoromethyl)-3H-imidazo[4,5-b]pyridine (700 mg, 2.0 mmol) was dissolved in acetic acid (10 ml), and N-chlorosuccinimide (1.3 g, 10 mmol) was added. The reaction mixture was stirred at room temperature for 12 h. After the solvent had been removed on a rotary evaporator, the residue was purified by chromatography (SiO$_2$, eluent: dichloromethane, pentane).

MH$^+$: 386; $^1$H-NMR (300 MHz, D$_6$-DMSO) δ ppm: 8.97 (s, 1H), 8.81 (s, 1H), 7.93-7.87 (m, 2H), 7.53-7.49 (d, 1H), 3.96 (s, 3H), 2-(5-Chloro-2H-indazol-2-yl)-3-methyl-6-(trifluoromethyl)-3H-imidazo[4,5-b]pyridine

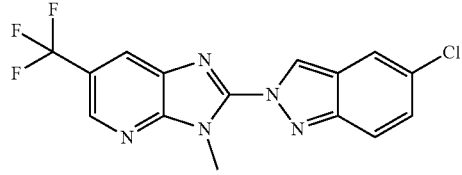 [SMILES: Cn1c(-n2cc3cc(Cl)ccc3n2)nc2cc(C(F)(F)F)cnc21]

2-Azido-5-chlorobenzaldehyde (1 g, 5.5 mmol) and 3-methyl-6-(trifluoromethyl)-3H-imidazo[4,5-b]pyridine-2-amine (1.2 g, 5.5 mmol) were dissolved in THF (15 ml), and tetraisopropyl titanate (1.6 g, 5.5 mmol) was added. The reaction mixture was heated to 60° C. for 6 h and then the solvent was distilled off. Without further purification, the residue was taken up in toluene (15 ml) and heated to 110° C. for 12 h. After the solvent had been removed on a rotary evaporator, the residue was purified by chromatography (SiO$_2$, eluent: dichloromethane, pentane).

MH$^+$: 352; $^1$H-NMR (300 MHz, D$_6$-DMSO) δ ppm: 9.25 (s, 1H), 8.86 (s, 1H), 8.64 (s, 1H), 7.98 (s, 1H), 7.89-7.86 (d, 1H), 7.44-7.40 (d, 1H), 4.24 (s, 3H).

2-Azido-5-chlorobenzaldehyde

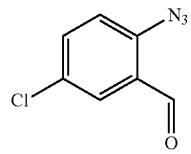 [SMILES: [N-]=[N+]=Nc1ccc(Cl)cc1C=O]

5-Chloro-2-fluorobenzaldehyde (1 g, 6.3 mmol) was dissolved in DMF (10 ml), and sodium azide (620 mg, 10 mmol) was added. The reaction mixture was heated at 60° C. for 12 h. The reaction solution was diluted with water and then extracted with ethyl acetate. The combined organic extracts were washed with saturated sodium chloride solution and dried over sodium sulfate. After the solvent had been removed, the crude product was used in the subsequent reaction without further purification.

2-[3-(Ethylsulfonyl)-4,5,6,7-tetrahydro-2H-indazol-2-yl]-3-methyl-6-(trifluoromethyl)-3H-imidazo[4,5-b]pyridine (Ex. I-10)

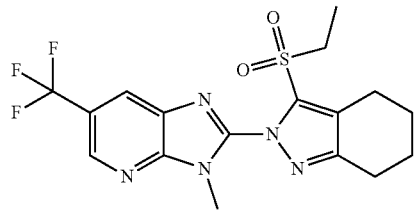 [SMILES: CCS(=O)(=O)c1c2c(nn1-c1nc3cc(C(F)(F)F)cnc3n1C)CCCC2]

Under an inert gas atmosphere, 2-[3-(ethylsulfanyl)-4,5,6,7-tetrahydro-2H-indazol-2-yl]-3-methyl-6-(trifluoromethyl)-3H-imidazo[4,5-b]pyridine (400 mg, 0.99 mmol, 1.00 equiv) were dissolved in 10 ml of dichloromethane, and formic acid (284 mg, 6.9 mmol, 7.00 equiv, 88%) and hydrogen peroxide solution (562 mg, 4.9 mmol, 5.00 equiv, 30%) were added. The reaction mixture was stirred at room temperature overnight and then diluted with 100 ml of dichloromethane. The mixture was washed with 100 ml of water and then with 100 ml of saturated NaCl solution. After the solvent had been removed on a rotary evaporator, the crude product was purified by means of preparative HPLC (SiO$_2$, acetonitrile:water).

MH$^+$: 414; $^1$H-NMR (300 MHz, D$_6$-DMSO) δ ppm: 8.92 (s, 1H), 8.71 (s, 1H9, 3.76 (m, 3H) 2.78 (m, 4H), 1.855 (m, 4H), 1.28 (t, 3H).

2-[3-(Ethylsulfanyl)-4,5,6,7-tetrahydro-2H-indazol-2-yl]-3-methyl-6-(trifluoromethyl)-3H-imidazo[4,5-b]pyridine

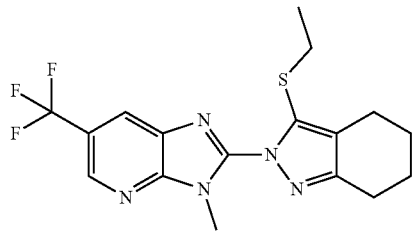 [SMILES: CCSc1c2c(nn1-c1nc3cc(C(F)(F)F)cnc3n1C)CCCC2]

Under an inert gas atmosphere, 2-[3-methyl-6-(trifluoromethyl)-3H-imidazo[4,5-b]pyridin-2-yl]-4,5,6,7-tetrahydro-2H-indazol-3-yl trifluoromethanesulfonate (650 mg, 1.4 mml, 1.0 eq.) were dissolved in 10 ml of dioxane, and ethyl mercaptan (171 mg, 2.77 mmol, 2.00 equiv), Pd$_2$(dba$_3$) CHCl$_3$ (72 mg, 0.07 mmol, 0.05 equiv), Xantphos (80 mg, 0.14 mmol, 0.1 equiv) and diisopropylethylamine (536 mg, 4.2 mmol, 3.00 equiv) were added. The reaction mixture was stirred at room temperature overnight and then diluted with 100 ml of dichloromethane. The mixture was washed with 100 ml of water and then with 100 ml of saturated NaCl solution. After the solvent had been removed on a rotary evaporator, the crude product was purified by column chromatography (SiO$_2$, pentane:ethyl acetate).

2-[3-Methyl-6-(trifluoromethyl)-3H-imidazo[4,5-b]pyridin-2-yl]-4,5,6,7-tetrahydro-2H-indazol-3-yl trifluoromethanesulfonate

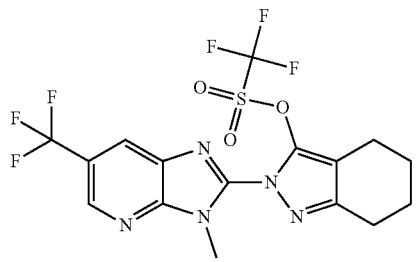 [SMILES: Cn1c(-n2nc3c(c2OS(=O)(=O)C(F)(F)F)CCCC3)nc2cc(C(F)(F)F)cnc21]

Under inert gas atmosphere, 2-[3-methyl-6-(trifluoromethyl)-3H-imidazo[4,5-b]pyridin-2-yl]-4,5,6,7-tetrahydro-2H-indazol-3-ol (400 mg, 1.2 mmol, 1.0 eq.) was dissolved in 10 ml of dry dioxane, and N-phenylbis(trifluoromethanesulfonimide) (636 mg, 1.8 mmol, 1.50 equiv) and diisopropylethylamine (301 mg, 2.4 mmol, 2.00 equiv) were added. The reaction mixture was stirred at room temperature overnight and then diluted with 100 ml of dichloromethane. The mixture was washed with 100 ml of water and then with 100 ml of saturated NaCl solution. After the solvent had been removed on a rotary evaporator, the crude product was purified by column chromatography (SiO$_2$, dichloromethane:methanol).

MH$^+$:470; $^1$H-NMR (300 MHz, D$_6$-DMSO) δ ppm: 8.86 (s, 1H), 8.59 (s, 1H), 3.98 (s, 3H), 2.75 (m, 2H), 2.58 (m, 2H), 1.80 (m, 4H).

2-[3-Methyl-6-(trifluoromethyl)-3H-imidazo[4,5-b]pyridin-2-yl]-4,5,6,7-tetrahydro-2H-indazol-3-ol

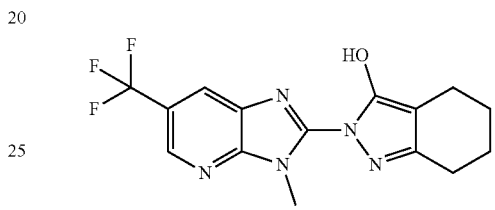

Under inert gas atmosphere, 2-hydrazino-3-methyl-6-(trifluoromethyl)-3H-imidazo[4,5-b]pyridine (1 g, 4.3 mmol, 1.0 eq.) were dissolved in 10 ml of glacial acetic acid, and ethyl 2-oxocyclohexanecarboxylate (1.5 g, 8.7 mmol, 2.0 eq.) was added. The reaction mixture was stirred at 80° C. for 1 h, cooled down to room temperature and then diluted with 100 ml of ethyl acetate. The mixture was washed with 100 ml of water and then with 100 ml of saturated NaCl solution. After the solvent had been removed on a rotary evaporator, the crude product was purified by column chromatography (SiO$_2$, pentane:ethyl acetate).

MH$^+$: 337; $^1$H-NMR (300 MHz, D$_6$-DMSO) δ ppm: 11.32 (s-b, 1H), 8.77 (s, 1H), 8.47 (s, 1H), 3.91 (s, 3H), 2.54 (s, 2H), 2.23 (m, 2H), 1.73 (m, 4H).

2-Hydrazino-3-methyl-6-(trifluoromethyl)-3H-imidazo[4,5-b]pyridine

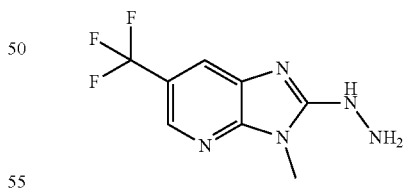

Under inert gas atmosphere, 2-chloro-3-methyl-6-(trifluoromethyl)-3H-imidazo[4,5-b]pyridine (5 g, 21 mmol, 1.0 eq., for preparation see US2015/94329 A1, 2015) were dissolved in 50 ml of dry methanol, and hydrazine hydrate (5.3 g, 11 mmol, 5.0 eq.) was added. The reaction mixture was stirred at room temperature overnight and then diluted with 100 ml of dichloromethane. The mixture was washed with 100 ml of water and then with 100 ml of saturated NaCl solution. After the solvent had been removed on a rotary evaporator, the crude product was used in the next reaction without further purification.

2-[3-(Ethylsulfonyl)-4-(trifluoromethyl)-2H-indazol-2-yl]-3-methyl-6-(trifluoromethyl)-3H-imidazo[4,5-b]pyridine (Ex. I-17)

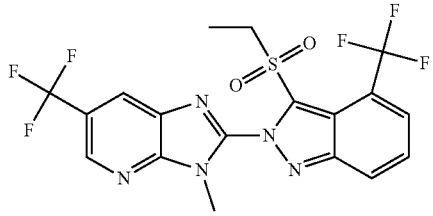 [SMILES: CCS(=O)(=O)c1c2c(C(F)(F)F)cccc2nn1-c1nc2cc(C(F)(F)F)cnc2n1C]

Under inert gas atmosphere, 2-[3-(ethylsulfanyl)-4-(trifluoromethyl)-2H-indazol-2-yl]-3-methyl-6-(trifluoromethyl)-3H-imidazo[4,5-b]pyridine (220 mg, 0.49 mmol, 1 eq.) was dissolved in formic acid (142 mg, 3.5 mmol, 88%, 7 eq.) and aqueous hydrogen peroxide solution (280 mg, 2.5 mmol, 5.00 eq. 30%), and the mixture was stirred at room temperature for 4 h. The reaction mixture was extracted with dichloromethane (2×100 ml). The combined organic extracts were washed with water and saturated sodium chloride solution, and freed of the solvent on a rotary evaporator. The crude product was purified by means of preparative HPLC (SiO$_2$, acetonitrile:water/0.1% formic acid).

$^1$H-NMR (300 MHz, D$_6$-DMSO) δ ppm: 8.97-8.87 (m, 2H), 8.70 (m, 1H), 8.12-8.00 (m, 2H), 4.18 (s, 3H), 3.92-3.87 (q, 2H), 1.45-1.40 (t, 3H).

2-[3-(Ethylsulfanyl)-4-(trifluoromethyl)-2H-indazol-2-yl]-3-methyl-6-(trifluoromethyl)-3H-imidazo[4,5-b]pyridine

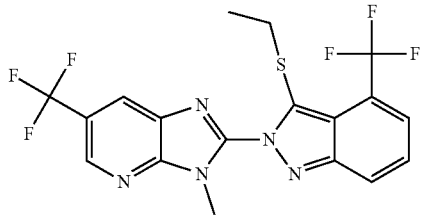 [SMILES: CCSc1c2c(C(F)(F)F)cccc2nn1-c1nc2cc(C(F)(F)F)cnc2n1C]

Under inert gas atmosphere, 2-[3-iodo-4-(trifluoromethyl)-2H-indazol-2-yl]-3-methyl-6-(trifluoromethyl)-3H-imidazo[4,5-b]pyridine (290 mg, 0.57 mmol, 1.00 equiv) was dissolved in dry dioxane (10 ml), and ethyl mercaptan (70 mg, 1.4 mmol, 2.00 equiv), Pd$_2$(dba)$_3$CHCl$_3$ (29 mg, 0.03 mmol, 0.05 equiv), Xantphos (33 mg, 0.057 mmol, 0.1 equiv), and diisopropylethylamine (220 mg, 1.7 mmol, 3.00 equiv) were added. The reaction mixture was heated at 80° C. for 2 h and cooled down to room temperature, then diluted with dichloromethane (100 ml). The solution was washed with water and saturated sodium chloride solution, and freed of the solvent on a rotary evaporator. The crude product was purified by means of preparative HPLC (SiO$_2$, acetonitrile:water/0.1% formic acid).

MH$^+$: 446; $^1$H-NMR (300 MHz, D$_6$-DMSO) δ ppm: 8.93-8.88 (m, 1H), 8.77 (d, 1H), 8.52 (d, 1H), 4.20 (s, 3H), 3.44-3.36 (q, 2H), 1.47 (t, 3H).

2-[3-Iodo-4-(trifluoromethyl)-2H-indazol-2-yl]-3-methyl-6-(trifluoromethyl)-3H-imidazo[4,5-b]pyridine

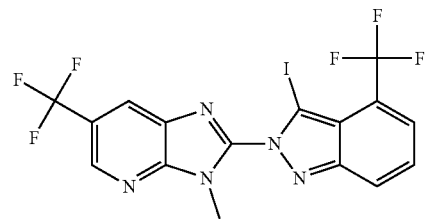 [SMILES: Cn1c(-n2nc3cccc(C(F)(F)F)c3c2I)nc2cc(C(F)(F)F)cnc21]

Under an inert gas atmosphere, 3-iodo-4-(trifluoromethyl)-2H-indazole (300 mg, 0.96 mmol, 1.00 equiv) was dissolved in DMF (10 ml) and cooled to 0° C. Over a period of 30 min, sodium hydride (38 mg, 0.96 mmol, 1.00 equiv) was added, followed by 2-chloro-3-methyl-6-(trifluoromethyl)-3H-imidazo[4,5-b]pyridine (339 mg, 1.4 mmol, 1.50 equiv). The reaction mixture was heated at 80° C. for 1 h. After cooling to room temperature, the solution was diluted with ethyl acetate. The mixture was washed with water and saturated sodium chloride solution, and freed of the solvent on a rotary evaporator. The crude product was purified by column chromatography (SiO$_2$, pentane:ethyl acetate).

MH$^+$: 512; $^1$H-NMR (300 MHz, D$_6$-DMSO) δ ppm: 8.82 (m, 2H), 8.57 (s, 1H), 7.94-7.86 (m, 2H), 4.04 (s, 3H).

3-Iodo-4-(trifluoromethyl)-2H-indazole

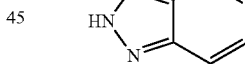

Under an inert gas atmosphere, 4-(trifluoromethyl)-2H-indazole (500 mg, 2.7 mmol, 1.00 equiv) were dissolved in DMF (10 ml), and iodine (1.4 g, 5.4 mmol, 2.00 equiv) and potassium hydroxide (378 mg, 6.8 mmol, 2.50 equiv) were added. The mixture was stirred at room temperature for 30 min. The solution was diluted with dichloromethane (100 ml) and washed first with sodium thiosulfate solution and then with saturated sodium chloride solution. After the solvent had been removed on a rotary evaporator, the crude product was used in the subsequent reaction without further purification.

MH$^+$: 313; $^1$H-NMR (300 MHz, D$_6$-DMSO) δ ppm: 14.10 (s, 1H), 7.96 (d, 1H), 7.64-7.53 (m, 2H).

N-{3-(Ethylsulfonyl)-2-[3-methyl-6-(trifluoromethyl)-3H-imidazo[4,5-b]pyridin-2-yl]-2H-indazol-6-yl}acetamide (Ex. I-18)

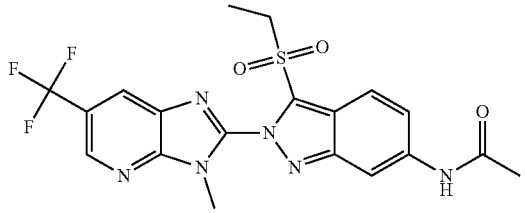 [SMILES: CCS(=O)(=O)c1c2ccc(NC(C)=O)cc2nn1-c1nc2cc(C(F)(F)F)cnc2n1C]

N-{3-(Ethylsulfanyl)-2-[3-methyl-6-(trifluoromethyl)-3H-imidazo[4,5-b]pyridin-2-yl]-2H-indazol-6-yl}acetamide (35 mg, 0.1 mmol) was dissolved in dichloromethane (2 ml) and cooled to 0° C., and aqueous hydrogen peroxide solution (0.2 ml, 1.0 mmol, 30%) and formic acid (60 mg, 1 mmol, 88%) were added. The reaction mixture was stirred at room temperature for 48 h and then diluted with dichloromethane. The mixture was washed with saturated sodium hydrogencarbonate solution. The organic phase was dried over sodium sulfate and freed of the solvent on a rotary evaporator. The crude product was purified by preparative TLC (SiO$_2$, pentane/ethyl acetate).

MH$^+$: 467; $^1$H-NMR (300 MHz, D$_6$-DMSO) δ ppm: 10.70 (s, 1H), 9.49 (s, 1H), 8.92 (s, 1H), 8.71 (s, 1H), 8.33-8.25 (m, 2H), 4.33 (s, 3H), 3.86-3.83 (m, 2H), 2.56 (s, 3H), 1.30-1.25 (t, 3H).

N-{3-(Ethylsulfanyl)-2-[3-methyl-6-(trifluoromethyl)-3H-imidazo[4,5-b]pyridin-2-yl]-2H-indazol-6-yl}acetamide

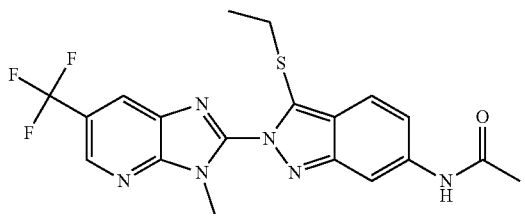 [SMILES: CCSc1c2ccc(NC(C)=O)cc2nn1-c1nc2cc(C(F)(F)F)cnc2n1C]

Under an inert gas atmosphere, N-{3-chloro-2-[3-methyl-6-(trifluoromethyl)-3H-imidazo[4,5-b]pyridin-2-yl]-2H-indazol-6-yl}acetamide (60 mg, 0.2 mmol) was dissolved in 1,4-dioxane (2 ml), and ethyl mercaptan (60 mg, 1.0 mmol), diisopropylethylamine (129 mg, 1.0 mmol), Pd$_2$(dba)$_3$CHCl$_3$ (55 mg, 0.05 mmol) and Xantphos (55 mg, 0.1 mmol) were added. The reaction mixture was heated to 110° C. for 12 h. After being cooled down to room temperature, the reaction solution was washed with water. The aqueous phase was extracted repeatedly with ethyl acetate. The combined organic extracts were dried over sodium sulfate and freed of the solvent on a rotary evaporator. The crude product was purified by preparative TLC (SiO$_2$, pentane/ethyl acetate).

MH$^+$: 435; $^1$H-NMR (300 MHz, D$_6$-DMSO) δ ppm: 9.61 (s, 1H), 9.28 (s, 1H), 8.84 (s, 1H), 8.62 (s, 1H), 7.78 (m, 1H), 7.55 (m, 1H), 4.29 (s, 3H), 3.34-3.18 (q, 2H), 2.15 (s, 3H), 1.23-1.11 (t, 3H).

N-{3-Chloro-2-[3-methyl-6-(trifluoromethyl)-3H-imidazo[4,5-b]pyridin-2-yl]-2H-indazol-6-yl}acetamide

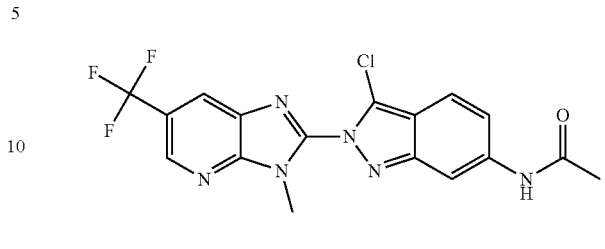

N-{2-[3-Methyl-6-(trifluoromethyl)-3H-imidazo[4,5-b]pyridin-2-yl]-2H-indazol-6-yl}acetamide (150 mg, 0.4 mmol) was dissolved in glacial acetic acid (5 ml), N-chlorosuccinimide (120 mg, 1 mmol) was added and the mixture was stirred at room temperature for 12 h. The reaction mixture was freed of the solvent and the crude product was purified by column chromatography (SiO$_2$, pentane/dichloromethane).

MH$^+$: 409; $^1$H-NMR (300 MHz, D$_6$-DMSO) δ ppm: 8.72 (s, 1H), 8.35-8.32 (m, 1H), 8.26 (s, 2H) 7.71-7.64 (m, 2H), 3.82 (s, 3H), 2.21 (s, 3H).

N-{2-[3-Methyl-6-(trifluoromethyl)-3H-imidazo[4,5-b]pyridin-2-yl]-2H-indazol-6-yl}acetamide

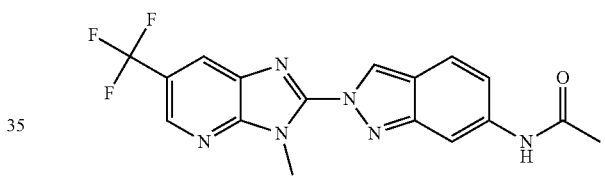

Under an inert gas atmosphere, in a pressure vessel, 2-(6-bromo-2H-indazol-2-yl)-3-methyl-6-(trifluoromethyl)-3H-imidazo[4,5-b]pyridine (0.8 g, 2 mmol), acetamide (0.3 g, 5 mmol), caesium carbonate (1.6 g, 5 mmol), Pd$_2$(dba)$_3$CHCl$_3$ (0.12 g, 0.1 mmol) and Xantphos (0.11 g, 0.2 mmol) were dissolved in 1,4-dioxane (10 ml) and heated to 110° C. for 2 h. The reaction mixture was diluted with dichloromethane and washed with saturated sodium chloride solution. The organic phase was dried over sodium sulfate and freed of the solvent on a rotary evaporator. The crude product was purified by column chromatography (SiO$_2$, pentane/ethyl acetate).

MH$^+$: 375; $^1$H-NMR (300 MHz, D$_6$-DMSO) δ ppm: 10.37 (s, 1H), 8.88 (s, 1H), 8.77 (s, 1H), 8.58 (s, 1H), 8.47 (s, 1H), 7.87 (d, 1H), 7.60 (d, 1H), 4.16 (s, 3H), 2.12 (s, 3H).

2-(6-Bromo-2H-indazol-2-yl)-3-methyl-6-(trifluoromethyl)-3H-imidazo[4,5-b]pyridine

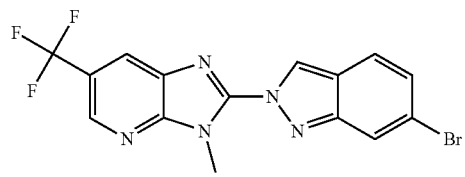 [SMILES: Cn1c(-n2cc3ccc(Br)cc3n2)nc2cc(C(F)(F)F)cnc21]

Under inert gas atmosphere, 4-bromo-2-fluorobenzaldehyde (4 g, 20 mmol) was dissolved in DMF (20 ml), and sodium azide (1.240 g, 20 mmol) was added. The reaction mixture was heated to 60° C. for 12 h. The reaction solution was diluted with water and extracted twice with ethyl acetate. The combined organic extracts were freed of the solvent.

The crude product (4 g, 18 mmol) was dissolved in THF (30 ml) under an inert gas atmosphere, and 3-methyl-6-(trifluoromethyl)-3H-imidazo[4,5-b]pyridine-2-amine (4.2 g, 20 mmol) and titanium triisopropoxide (6 g, 21 mmol) were added. The reaction mixture was heated to 60° C. for 6 h.

After the solvent had been removed under reduced pressure, the residue was taken up in toluene (30 ml) and heated to 110° C. for 12 h. The solvent was removed on a rotary evaporator and the crude product was purified by column chromatography (SiO$_2$, pentane/dichloromethane).

MH$^+$: 397; $^1$H-NMR (600 MHz, D$_6$-DMSO) δ ppm: 9.32 (s, 1H), 8.90 (s, 1H), 8.65 (s, 1H), 8.12 (s, 1H), 7.85 (d, 1H), 7.35 (d, 1H), 4.23 (s, 3H).

3-(Ethylsulfonyl)-2-[3-methyl-6-(trifluoromethyl)-3H-imidazo[4,5-b]pyridin-2-yl]-2H-pyrazolo[3,4-c]pyridine (Ex. I-19)

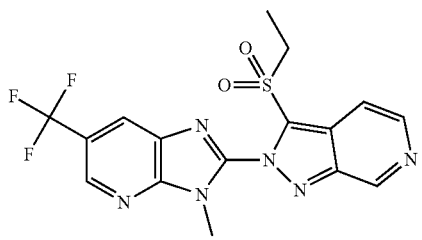 [SMILES: CCS(=O)(=O)c1c2ccncc2nn1-c1nc2cc(C(F)(F)F)cnc2n1C]

3-(Ethylsulfanyl)-2-[3-methyl-6-(trifluoromethyl)-3H-imidazo[4,5-b]pyridin-2-yl]-2H-pyrazolo[3,4-c]pyridine (100 mg, 0.27 mmol) was dissolved in dichloromethane (20 ml), cooled to 0° C. and admixed with formic acid (5 ml) and then slowly with aqueous hydrogen peroxide solution (0.5 mL, 30%). The reaction mixture was stirred at room temperature for 2 h. The mixture was washed first with saturated sodium hydrogencarbonate solution and then with saturated sodium chloride solution. The combined organic phases were dried over sodium sulfate and freed of the solvent on a rotary evaporator. The crude product was purified by preparative HPLC.

MH$^+$: 411; $^1$H-NMR (600 MHz, D6-DMSO) δ ppm: 9.82 (s, 1H), 9.44 (s, 1H), 8.94 (s, 1H), 8.75 (s, 1H), 8.70 (s, 1H), 4.25 (s, 3H), 3.60-3.54 (m, 2H), 1.19 (t, 3H).

3-(Ethylsulfanyl)-2-[3-methyl-6-(trifluoromethyl)-3H-imidazo[4,5-b]pyridin-2-yl]-2H-pyrazolo[3,4-c]pyridine

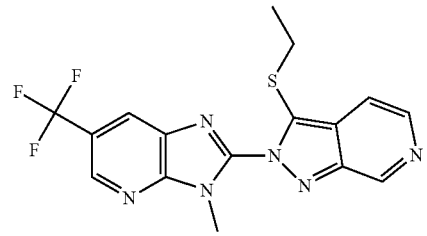 [SMILES: CCSc1c2ccncc2nn1-c1nc2cc(C(F)(F)F)cnc2n1C]

3-Bromo-2-[3-methyl-6-(trifluoromethyl)-3H-imidazo[4,5-b]pyridin-2-yl]-2H-pyrazolo[3,4-c]pyridine (300 mg, 0.76 mmol), ethyl mercaptan (54 mg, 0.87 mmol), Pd$_2$(dba)$_3$ CHCl$_3$ (124 mg, 0.12 mmol), Xantphos (140 mg, 0.24 mmol) and diisopropylethylamine (312 mg, 2.4 mmol) were dissolved in 10 ml of 1,4-dioxane and heated in a closed pressure vessel at 80° C. for 2 h. After cooling to room temperature, the reaction solution was poured into 50 ml of water and the mixture was extracted twice with ethyl acetate. The combined organic extracts were washed with saturated sodium chloride solution, dried over sodium sulfate and concentrated on a rotary evaporator. The crude product was purified by column chromatography.

MH$^+$: 379; $^1$H-NMR (600 MHz, D6-DMSO) δ ppm: 9.233 (s, 1H), 9.26 (s, 1H), 8.92 (s, 1H), 8.70 (m, 1H), 8.15 (s, 1H), 4.22 (s, 3H), 3.35-3.21 (m, 2H), 1.32 (t, 3H).

3-Bromo-2-[3-methyl-6-(trifluoromethyl)-3H-imidazo[4,5-b]pyridin-2-yl]-2H-pyrazolo[3,4-c]pyridine

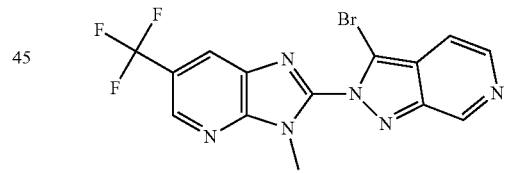

2-[3-Methyl-6-(trifluoromethyl)-3H-imidazo[4,5-b]pyridin-2-yl]-2H-pyrazolo[3,4-c]pyridine (500 mg, 1.57 mmol) was dissolved in 5 ml of glacial acetic acid and admixed at 0° C. with portions of N-bromosuccinimide (280 mg, 1.57 mmol). The reaction mixture was stirred at room temperature for 2 h. Following addition of 50 ml of water, a pH of 8 was set by addition of sodium hydrogencarbonate. The mixture was extracted three times with ethyl acetate. The combined organic extracts were washed three times with saturated sodium chloride solution, dried over sodium sulfate and concentrated on a rotary evaporator. The crude product was purified by preparative TLC (ethyl acetate/petroleum ether).

MH$^+$: 399; $^1$H-NMR (600 MHz, D6-DMSO) δ ppm: 9.45 (s, 1H), 9.37 (s, 1H), 8.93 (s, 1H), 8.73 (s, 1H), 8.43 (s, 1H), 4.21 (s, 3H).

2-[3-Methyl-6-(trifluoromethyl)-3H-imidazo[4,5-b]pyridin-2-yl]-2H-pyrazolo[3,4-c]pyridine

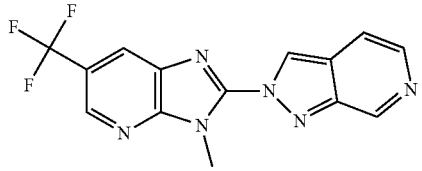 [SMILES: Cn1c(-n2cc3ccncc3n2)nc2cc(C(F)(F)F)cnc21]

3-Fluoroisonicotinaldehyde (800 mg, 6.4 mmol) and sodium azide (416 mg, 6.4 mmol) were dissolved in 10 ml of DMF and stirred at 50° C. for 4 h. The mixture was poured into water and extracted three times with ethyl acetate. The combined organic extracts were dried over sodium sulfate and concentrated on a rotary evaporator. The crude 3-azidoisonicotinaldehyde product was obtained as a yellow solid and was used without further purification in the subsequent reaction.

3-Azidoisonicotinaldehyde (620 mg, 4.16 mmol) and 3-methyl-6-(trifluoromethyl)-3H-imidazo[4,5-b]pyridin-2-amine (910 mg, 4.2 mmol) were dissolved in 30 ml of toluene, and tetraisopropyl orthotitanate (2.4 g, 8.4 mmol) was added. The reaction solution was heated in a microwave at 120° C. for 2 h. After cooling to room temperature, the reaction was ended by addition of 100 ml of water. The mixture was extracted three times with ethyl acetate. The combined organic extracts were washed with saturated sodium chloride solution, dried over sodium sulfate and concentrated on a rotary evaporator. The crude product was purified by column chromatography (ethyl acetate/petroleum ether).

MH$^+$: 319; $^1$H-NMR (600 MHz, D6-DMSO) δ ppm: 9.43 (s, 1H), 9.09 (s, 1H), 8.75 (s, 1H), 8.31-8.255 (m, 2H), 7.64 (m, 1H), 4.44 (s, 3H).

In analogy to the examples and according to the above-described preparation processes, it is also possible to obtain the other compounds of the formula (Ia) or (Ib) listed in Table 1:

Ia

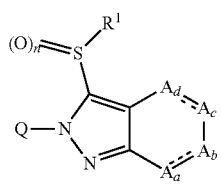

Ib

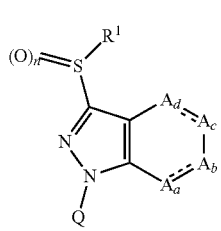

TABLE 1

| Ex. No. | Structure |
|---|---|
| I-1 | ![structure] |
| I-2 | ![structure] |
| I-3 | ![structure] |
| I-4 | ![structure] |
| I-5 | ![structure] |
| I-6 | ![structure] |

TABLE 1-continued

| Ex. No. | Structure |
|---|---|
| I-7 | 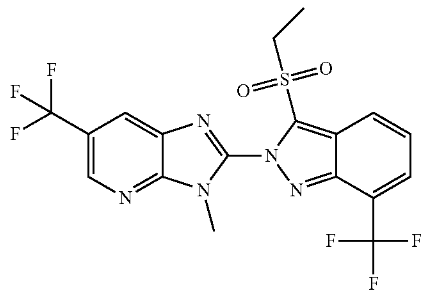 [SMILES: CCS(=O)(=O)c1c2cccc(C(F)(F)F)c2nn1-c1nc2cc(C(F)(F)F)cnc2n1C] |
| I-8 | 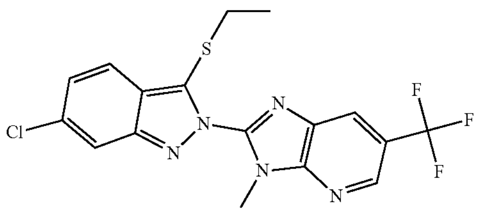 [SMILES: CCSc1c2ccc(Cl)cc2nn1-c1nc2cc(C(F)(F)F)cnc2n1C] |
| I-9 | 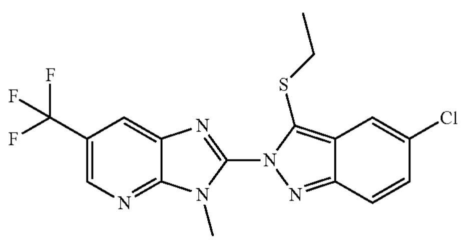 [SMILES: CCSc1c2cc(Cl)ccc2nn1-c1nc2cc(C(F)(F)F)cnc2n1C] |
| I-10 | 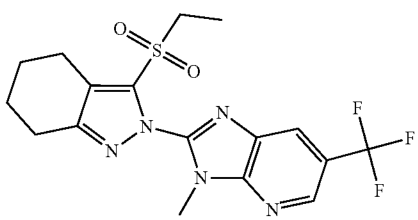 [SMILES: CCS(=O)(=O)c1c2c(nn1-c1nc3cc(C(F)(F)F)cnc3n1C)CCCC2] |
| I-11 | 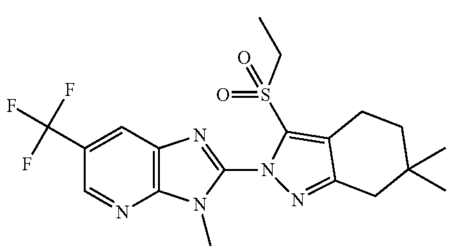 [SMILES: CCS(=O)(=O)c1c2c(nn1-c1nc3cc(C(F)(F)F)cnc3n1C)CC(C)(C)CC2] |
| I-12 | 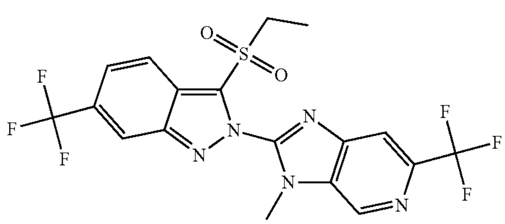 [SMILES: CCS(=O)(=O)c1c2ccc(C(F)(F)F)cc2nn1-c1nc2cc(C(F)(F)F)ncc2n1C] |
| I-13 | |
| I-14 | |
| I-15 | |
| I-16 | |
| I-17 | |
| I-18 | |

TABLE 1-continued

| Ex. No. | Structure |
|---|---|
| I-19 | (structure image) |

NMR Data of Selected Examples

NMR Peak List Method

The 1H-NMR data of selected examples are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of:

$\delta_1$ (intensity$_1$); $\delta_2$ (intensity$_2$); ... ; $\delta_i$ (intensity); ... ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

When stating compound signals in the delta range of solvents and/or water, in our lists of 1H NMR peaks, the usual solvent peaks, for example peaks of DMSO in DMSO-$D_6$ and the peak of water are shown, which usually have on average a high intensity.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

TABLE 2

NMR data of selected examples

Example I-1: $^1$H-NMR(300.1 MHz, d$_6$-DMSO):
δ = 9.021(2.0); 9.016(2.2); 8.851(2.1); 8.845(2.0); 8.219(2.2); 8.216(2.4); 8.214(2.3); 8.104(2.0); 8.102(2.0); 8.073(2.3); 8.071(2.3); 7.594(1.5); 7.589(1.5); 7.564(1.4); 7.558(1.4); 3.937(0.9); 3.913(3.2); 3.888(3.2); 3.864(1.0); 3.828(16.0); 3.322(9.4); 2.515(4.6); 2.509(9.2); 2.503(12.3); 2.497(8.4); 2.492(3.8); 2.076(0.3); 1.311(3.3); 1.286(7.7); 1.262(3.2); 0.000(7.0)

Example I-2: $^1$H-NMR(400.2 MHz, d$_6$-DMSO):
δ = 9.022(2.5); 9.019(2.5); 8.856(2.6); 8.853(2.5); 8.122(2.3); 8.099(2.6); 8.060(2.7); 8.057(2.8); 7.678(2.0); 7.673(1.9); 7.654(1.8); 7.650(1.7); 3.943(1.0); 3.925(3.4); 3.906(3.4); 3.888(1.1); 3.834(16.0); 3.329(14.6); 2.510(6.8); 2.506(9.1); 2.501(6.7); 1.319(3.6); 1.300(7.8); 1.282(3.4); 0.001(5.1)

Example I-3: $^1$H-NMR(400.2 MHz, d$_6$-DMSO):
δ = 9.018(2.5); 9.015(2.5); 8.848(2.6); 8.843(2.4); 8.081(1.9); 8.060(2.1); 8.037(2.0); 8.014(2.2); 7.675(1.0); 7.674(1.0); 7.659(1.4); 7.657(1.4); 7.637(1.2); 7.590(1.4); 7.568(1.4); 7.552(0.9); 3.968(0.3); 3.906(1.1); 3.888(3.5); 3.870(3.6); 3.851(1.3); 3.824(16.0); 3.335(11.0); 2.512(4.6); 2.508(5.9); 2.504(4.3); 2.081(1.4); 1.307(3.7); 1.288(7.8); 1.270(3.5); 0.001(2.4)

Example I-4: $^1$H-NMR(300.1 MHz, d$_6$-DMSO):
δ = 9.033(1.8); 9.031(2.0); 9.027(2.1); 8.863(2.2); 8.858(2.0); 8.050(1.8); 8.047(2.0); 8.021(2.2); 8.019(2.1); 7.823(1.8); 7.820(2.0); 7.798(2.3); 7.796(2.2); 7.568(1.8); 7.543(1.7); 7.539(1.8); 7.514(1.4); 5.756(1.1); 3.913(0.8); 3.888(3.0); 3.864(3.2); 3.837(16.0); 3.316(22.0); 2.514(10.8); 2.508(21.5); 2.502(28.6); 2.496(19.5); 2.490(8.8); 1.305(3.2); 1.281(7.4); 1.256(3.1); 1.235(0.5); 0.011(0.6); 0.000(17.5); −0.011(0.6)

Example I-5: $^1$H-NMR(300.1 MHz, d$_6$-DMSO):
δ = 9.036(2.4); 9.031(2.5); 8.875(2.5); 8.870(2.4); 8.431(2.4); 8.308(1.6); 8.277(1.9); 7.902(1.6); 7.897(1.6); 7.872(1.4); 7.866(1.4); 4.013(1.0); 3.988(3.3); 3.964(3.4); 3.939(1.0); 3.849(16.0); 3.321(16.8); 2.515(6.1); 2.510(11.6); 2.504(15.1); 2.498(10.7); 2.077(0.8); 1.337(3.5); 1.313(7.9); 1.288(3.4); 0.000(1.8)

Example I-6: $^1$H-NMR(300.1 MHz, d$_6$-DMSO):
δ = 9.037(2.0); 9.035(2.2); 9.030(2.2); 8.871(2.3); 8.866(2.2); 8.590(2.3); 8.587(2.2); 8.310(1.5); 8.279(1.7); 7.819(1.5); 7.814(1.5); 7.788(1.4); 7.784(1.4); 3.959(0.9); 3.934(3.1); 3.910(3.2); 3.885(1.0); 3.845(16.0); 3.319(14.0); 2.516(3.4); 2.511(6.7); 2.505(8.8); 2.499(6.0); 2.493(2.7); 1.325(3.3); 1.300(7.6); 1.276(3.1); 0.000(6.8)

Example I-7: $^1$H-NMR(400.2 MHz, d$_6$-DMSO):
δ = 9.036(3.2); 8.874(3.3); 8.384(2.2); 8.362(2.3); 8.139(2.0); 8.122(2.1); 7.730(1.3); 7.711(1.8); 7.691(1.2); 3.967(1.3); 3.949(3.8); 3.930(3.8); 3.912(1.3); 3.844(16.0); 3.329(35.2); 2.674(0.4); 2.505(53.4); 2.332(0.3); 1.325(4.1); 1.306(8.2); 1.288(3.8); 0.002(19.8)

Example I-10: $^1$H-NMR(300.1 MHz, d$_6$-DMSO):
δ = 8.9232 (2.1); 8.9189 (2.2); 8.7100 (2.2); 8.7047 (2.2); 3.7751 (16.0); 3.7594 (3.3); 3.7347 (3.2); 3.7102 (0.9); 3.3171 (13.7); 2.8629 (1.1); 2.8424 (2.4); 2.8234 (1.2); 2.8017 (1.1); 2.7824 (2.4); 2.7620 (1.2); 2.5137 (6.7); 2.5078 (13.1); 2.5019 (17.2); 2.4960 (11.8); 1.8549 (1.0); 1.8309 (1.4); 1.8138 (1.6); 1.7988 (1.4); 1.7740 (0.9); 1.3034 (3.3); 1.2789 (7.4); 1.2542 (3.1); −0.0001 (6.9)

Example I-11: $^1$H-NMR(300.1 MHz, d$_6$-DMSO):
δ = 8.9269 (1.8); 8.9225 (1.9); 8.7139 (1.9); 8.7089 (1.9); 3.7944 (0.8); 3.7635 (13.8); 3.7451 (2.8); 3.7208 (0.8); 3.3243 (4.0); 2.8691 (1.0); 2.8475 (2.1); 2.8254 (1.0); 2.5732 (4.6); 2.5144 (5.6); 2.5086 (11.1); 2.5026 (14.7); 2.4967 (10.0); 2.4910 (4.6); 2.0762 (0.7); 1.6309 (1.0); 1.6090 (2.1); 1.5870 (0.9); 1.2981 (2.7); 1.2736 (6.3); 1.2489 (2.6); 1.0318 (16.0); 0.0000 (6.7)

TABLE 2-continued

NMR data of selected examples

Example I-12: ¹H-NMR(400.1 MHz, d₆-DMSO):
δ = 15.9016 (0.3); 9.4083 (5.0); 8.9769 (0.4); 8.5945 (4.2); 8.4655 (5.3); 8.2965 (2.3); 8.2729 (2.7); 7.8162 (2.6); 7.7937 (2.5); 6.5178 (0.8); 3.9481 (16.0); 3.9271 (1.6); 3.9095 (4.0); 3.8904 (4.0); 3.8736 (1.4); 3.6357 (0.4); 3.5058 (0.5); 3.4200 (0.4); 3.3164 (132.2); 3.1674 (0.3); 2.7077 (0.3); 2.6710 (2.0); 2.5863 (0.5); 2.5005 (301.4); 2.3273 (1.8); 1.7702 (0.4); 1.4486 (0.4); 1.3382 (0.5); 1.3048 (4.3); 1.2865 (8.5); 1.2683 (4.3); 1.2339 (4.5); 1.1527 (0.5); 0.9399 (0.5); 0.9136 (0.4); 0.8475 (0.5); 0.8175 (0.5); 0.8038 (0.6); 0.1460 (0.7); 0.1309 (0.4); 0.0666 (0.5); −0.0003 (104.1); −0.1513 (0.4)

Example I-13: ¹H-NMR(300.1 MHz, d₆-DMSO):
δ = 9.0101 (2.3); 9.0057 (2.4); 8.8248 (2.5); 8.8200 (2.4); 8.0548 (2.1); 8.0283 (2.3); 8.0261 (2.3); 7.7307 (1.7); 7.7086 (2.8); 7.7066 (2.7); 7.6583 (2.2); 7.6337 (1.4); 7.6296 (2.0); 7.6051 (1.2); 3.8655 (1.1); 3.8408 (3.6); 3.8161 (3.6); 3.7916 (1.2); 3.7374 (16.0); 3.3212 (5.6); 2.5144 (5.2); 2.5088 (10.2); 2.5029 (13.3); 2.4971 (9.4); 1.3261 (3.9); 1.3014 (8.8); 1.2767 (3.8); 0.0104 (0.4); −0.0001 (7.8)

Example I-14: ¹H-NMR(300.1 MHz, d₆-DMSO):
δ = 8.8861 (2.4); 8.8822 (2.4); 8.7844 (1.7); 8.7546 (2.0); 8.7160 (2.6); 8.7107 (2.5); 8.4781 (2.7); 8.2267 (1.4); 8.2217 (1.4); 8.1913 (1.3); 4.1658 (16.0); 4.1430 (0.4); 3.7941 (1.1); 3.7695 (3.6); 3.7451 (3.7); 3.7207 (1.2); 3.3255 (18.8); 2.5418 (0.4); 2.5081 (22.4); 2.5023 (29.0); 2.4966 (20.2); 2.0761 (1.0); 1.3553 (3.9); 1.3309 (8.6); 1.3064 (3.7); 0.0000 (12.1); −0.0112 (0.4)

Example I-15: ¹H-NMR(300.1 MHz, d₆-DMSO):
δ = 8.9277 (2.5); 8.8793 (2.1); 8.8752 (2.2); 8.7966 (2.4); 8.7916 (2.1); 8.4293 (1.6); 8.4006 (1.8); 7.9974 (1.4); 7.9933 (1.4); 7.9685 (1.2); 7.9645 (1.2); 4.1616 (16.0); 3.7664 (1.0); 3.7419 (3.4); 3.7174 (3.5); 3.6929 (1.1); 3.3207 (6.9); 2.5141 (6.8); 2.5083 (13.1); 2.5024 (17.1); 2.4965 (11.7); 2.0758 (1.0); 1.3470 (3.8); 1.3226 (8.4); 1.2981 (3.6); 0.0108 (0.5); −0.0001 (11.5); −0.0111 (0.4)

Example I-16: ¹H-NMR(300.1 MHz, d₆-DMSO):
δ = 8.9701 (1.6); 8.9419 (1.8); 8.8942 (2.2); 8.8900 (2.3); 8.8756 (0.4); 8.7063 (2.4); 8.7011 (2.3); 8.1221 (1.1); 8.0976 (2.0); 8.0528 (1.2); 8.0262 (1.6); 7.9997 (0.6); 4.1837 (1.8); 4.1671 (16.0); 3.9236 (1.0); 3.8989 (3.2); 3.8745 (3.3); 3.8502 (1.0); 3.3284 (22.6); 2.5420 (0.4); 2.5142 (9.8); 2.5085 (19.2); 2.5026 (25.2); 2.4968 (17.4); 2.0766 (0.4); 1.4551 (3.4); 1.4308 (7.8); 1.4063 (3.3); 1.3170 (0.3); 1.2923 (0.7); 1.2676 (0.3); 0.0109 (0.5); −0.0001 (12.0); −0.0111 (0.4)

Example I-17: ¹H-NMR(300.1 MHz, d₆-DMSO):
δ = 10.0529 (0.3); 9.0191 (2.3); 9.0037 (0.4); 8.9938 (0.4); 8.8346 (2.4); 8.3995 (1.7); 8.3701 (2.0); 8.1492 (1.5); 8.1249 (1.7); 7.8265 (1.0); 7.7981 (1.3); 7.7752 (0.9); 6.5318 (1.4); 5.7574 (0.8); 3.8205 (0.9); 3.7957 (3.7); 3.7863 (16.0); 3.7709 (3.2); 3.7464 (1.0); 3.6282 (0.4); 3.5977 (1.6); 3.5044 (0.7); 3.4591 (0.8); 3.4428 (0.9); 3.4279 (1.1); 3.3272 (2865.2); 3.2293 (0.7); 3.2216 (0.6); 2.7335 (2.7); 2.7276 (3.9); 2.7216 (3.0); 2.6179 (0.4); 2.5847 (0.8); 2.5131 (255.1); 2.5074 (494.6); 2.5015 (649.9); 2.4957 (454.5); 2.3976 (0.5); 2.3740 (0.3); 2.2770 (2.8); 2.2714 (3.8); 2.2653 (2.9); 2.0744 (1.4); 1.5058 (0.3); 1.4768 (0.4); 1.3220 (3.4); 1.2976 (7.2); 1.2729 (3.5); 1.2339 (7.3); 1.1482 (0.8); 1.1306 (0.3); 1.0771 (0.3); 0.9032 (0.4); 0.8725 (0.5); 0.8528 (0.9); 0.8267 (0.6); 0.8050 (0.6); 0.7800 (0.4); 0.1947 (1.0); 0.0107 (10.9); −0.0002 (273.0); −0.0112 (10.3); −0.0537 (0.4); −0.1988 (1.0)

Example I-18: ¹H-NMR(300 MHz, D₆-DMSO) δ = 10.70 (1), 9.49 (1), 8.92 (1), 8.71 (1), 8.33-8.25 (2), 4.33 (3), 3.86-3.83 (2), 2.56 (3), 1.30-1.25 (3)

Example I-19: ¹H-NMR(600 MHz, D6-DMSO) δ ppm: 9.82 (s, 1H), 9.44 (s, 1H), 8.94 (s, 1H), 8.75 (s, 1H), 8.70 (s, 1H), 4.25 (s, 3H), 3.60-3.54 (m, 2H), 1.19 (t, 3H).

USE EXAMPLES

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 μl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm², given homogeneous distribution, an area-based dose of 5 μg/cm² is achieved.

After the solvent has evaporated off, the glass tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 μg/cm². 100% efficacy means that all the fleas were dead or moribund. 0% efficacy means that no fleas were harmed.

In this test, for example, the following compounds from the preparation examples show an efficacy of 100% at an application rate of 5 μg/cm² (=500 g/ha): I-2, I-6, I-5, I-10

*Rhipicephalus sanguineus*—In Vitro Contact Tests with Adult Brown Dog Ticks

For the coating of the test tubes, 9 mg of active ingredient are first dissolved in 1 ml of acetone p.a. and then diluted to the desired concentration with acetone p.a. 250 μl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm², given homogeneous distribution, an area-based dose of 5 μg/cm² is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the base of the tube and incubated on a hotplate at 45-50° C. for not more than 5 min. Ticks which remain motionless on the base or move in such an uncoordinated manner that they are unable to deliberately avoid the heat by climbing upwards are considered to be dead or moribund.

A substance shows good efficacy against *Rhipicephalus sanguineus* when at least 80% efficacy at an application rate of 5 μg/cm² was achieved in this test. An efficacy of 100% means that all the ticks were dead or moribund. 0% efficacy means that none of the ticks were harmed.

In this test, for example, the following compounds from the preparation examples show an efficacy of 100% at an application rate of 5 µg/cm² (=500 g/ha): I-10

*Ctenocephalides felis*—Oral Test

Solvent: dimethyl sulfoxide

To produce a suitable active ingredient formulation, 10 mg of active ingredient are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

After 2 days, the kill in % is determined. 100% means that all of the fleas have been killed; 0% means that none of the fleas have been killed.

In this test, for example, the following compound from the preparation examples shows an efficacy of 80% at an application rate of 100 ppm: I-2

*Lucilia cuprina* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active ingredient formulation of the desired concentration.

After 2 days, the kill in % is determined. 100% means that all the larvae have been killed; 0% means that no larvae have been killed.

In this test, for example, the following compound from the preparation examples shows an efficacy of 100% at an application rate of 100 ppm: I-1, I-2, I-3, I-5, I-6, I-10

*Musca domestica* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined. 100% means that all of the flies have been killed; 0% means that none of the flies have been killed.

In this test, for example, the following compound from the preparation examples shows an efficacy of 90% at an application rate of 100 ppm: I-6

*Myzus persicae*—Oral Test

Solvent: 100 parts by weight of acetone

To produce a suitable active ingredient formulation, 1 part by weight of active ingredient is dissolved with the stated parts by weight of solvent and made up to the desired concentration with water. 50 µl of the active ingredient formulation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution through it.

After 5 days, the efficacy in % is determined. 100% means that all the aphids have been killed; 0% means that no aphids have been killed.

In this test, for example, the following compounds from the preparation examples show an efficacy of 100% at an application rate of 20 ppm: I-2, I-6

In this test, for example, the following compounds from the preparation examples show an efficacy of 100% at an application rate of 4 ppm: I-2, I-5, I-6, I-10, I-11, I-12

In this test, for example, the following compounds from the preparation examples show an efficacy of 90% at an application rate of 4 ppm: I-1, I-3, I-4

*Myzus persicae*—Spray Test

Solvent: 78 parts by weight of acetone 1.5 parts by weight of dimethylformamide

Emulsifier: alkylaryl polyglycol ether

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 5 days, the efficacy in % is determined. 100% means that all the aphids have been killed; 0% means that no aphids have been killed.

In this test, for example, the following compound from the preparation examples shows an efficacy of 100% at an application rate of 100 g/ha: I-3

In this test, for example, the following compound from the preparation examples shows an efficacy of 90% at an application rate of 100 g/ha: 1-10, I-11

*Phaedon cochleariae*—Spray Test

Solvent: 78.0 parts by weight of acetone 1.5 parts by weight of dimethylformamide Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compound from the preparation examples shows an efficacy of 100% at an application rate of 100 g/ha: I-1, I-2, I-3, I-4, I-5, I-6, I-12

*Spodoptera frugiperda*—Spray Test

Solvent: 78.0 parts by weight of acetone 1.5 parts by weight of dimethylformamide Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compound from the preparation examples shows an efficacy of 100% at an application rate of 100 g/ha: I-1, I-2, I-5, I-6, I-12

The invention claimed is:

1. A compound of formula (Ia) or (Ib)

where ⫽ represent single bonds or double bonds, in which, if ⫽ represent exclusively double bonds and hence Aa to Ad together with the carbon atoms adjacent to Aa and Ad in each case form an aromatic ring, Aa is nitrogen or $C(R^{10})$,
Ab is nitrogen or $C(R^{11})$,
Ac is nitrogen or $C(R^{12})$, and
Ad is nitrogen or $C(R^{13})$,
where not more than two of Aa, Ab, Ac and Ad are nitrogen, or, if ⫽ represent exclusively single bonds, Aa is $C(R^{10})(R^{14})$,
Ab is $C(R^{11})(R^{15})$,
Ac is $C(R^{12})(R^{16})$ and
Ad is $C(R^{13})(R^{17})$, $R^1$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$alkyl, $(C_1-C_6)$alkylsulfinyl-$(C_1-C_6)$alkyl, $(C_1-C_6)$haloalkylsulfinyl-$(C_1-C_6)$alkyl, $(C_1-C_6)$alkylsulfonyl-$(C_1-C_6)$alkyl, $(C_1-C_6)$haloalkylsulfonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulfinyl-$(C_1-C_6)$alkyl, $(C_1-C_6)$alkoxy-$(C_1-C_6)$alkylsulfonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulfonylamino, aminosulfonyl-$(C_1-C_6)$alkyl, $(C_1-C_6)$alkylaminosulfonyl-$(C_1-C_6)$alkyl, di$(C_1-C_6)$alkylaminosulfonyl-$(C_1-C_6)$alkyl, or is in each case singly or multiply, identically or differently aryl-, hetaryl- or heterocyclyl-substituted $(C_1-C_6)$alkyl, $(C_1-C_6)$alkoxy, $(C_2-C_6)$alkenyl, $(C_2-C_6)$alkynyl, $(C_3-C_8)$cycloalkyl, where aryl, hetaryl or heterocyclyl may each optionally be mono- or polysubstituted identically or differently by halogen, cyano, nitro, hydroxyl, amino, carboxyl, carbamoyl, aminosulfonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulfinyl, $(C_1-C_6)$alkylsulfonyl, $(C_1-C_6)$alkylsulfimino, $(C_1-C_6)$alkylsulfimino-$(C_1-C_6)$alkyl, $(C_1-C_6)$alkylsulfimino-$(C_2-C_6)$alkylcarbonyl, $(C_1-C_6)$alkylsulfoximino, $(C_1-C_6)$alkylsulfoximino-$(C_1-C_6)$alkyl, $(C_1-C_6)$alkylsulfoximino-$(C_2-C_6)$alkylcarbonyl, $(C_1-C_6)$alkoxycarbonyl, $(C_1-C_6)$alkylcarbonyl, $(C_3-C_6)$trialkylsilyl or benzyl, or $R^1$ is aryl, hetaryl or heterocyclyl, each optionally mono- or polysubstituted identically or differently by halogen, cyano, nitro, hydroxyl, amino, carboxyl, carbamoyl, $(C_1-C_6)$alkyl, $(C_3-C_8)$cycloalkyl, $(C_1-C_6)$-alkoxy, $(C_1-C_6)$haloalkyl, $(C_1-C_6)$haloalkoxy, $(C_1-C_6)$alkylthio, $(C_1-C_6)$alkylsulfinyl, $(C_1-C_6)$alkylsulfonyl, $(C_1-C_6)$alkylsulfimino, $(C_1-C_6)$alkylsulfimino-$(C_1-C_6)$alkyl, $(C_1-C_6)$alkylsulfimino-$(C_2-C_6)$alkylcarbonyl, $(C_1-C_6)$alkylsulfoximino, $(C_1-C_6)$alkylsulfoximino-$(C_1-C_6)$alkyl, $(C_1-C_6)$alkylsulfoximino-$(C_2-C_6)$alkylcarbonyl, $(C_1-C_6)$alkoxycarbonyl, $(C_1-C_6)$alkylcarbonyl, $(C_3-C_6)$trialkylsilyl, (=O) (in the case of heterocyclyl only) or $(=O)_2$ (in the case of heterocyclyl only), $R^{10}$, $R^{11}$, $R^{12}$, $R^{13}$, $R^{14}$, $R^{15}$, $R^{16}$, $R^{17}$ are independently hydrogen, cyano, halogen, nitro, hydroxyl, amino, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di$(C_1-C_6)$alkylaminocarbonyl, di$(C_1-C_6)$alkylaminothiocarbonyl, $(C_2-C_6)$alkenylaminocarbonyl, di$(C_2-C_6)$alkenylaminocarbonyl, $(C_3-C_8)$cycloalkylaminocarbonyl, $(C_1-C_6)$alkylsulfonylamino, $(C_1-C_6)$alkylamino, di$(C_1-C_6)$alkylamino, aminosulfonyl, $(C_1-C_6)$alkylaminosulfonyl, di$(C_1-C_6)$alkylaminosulfonyl, $(C_1-C_6)$alkylsulfoximino, aminothiocarbonyl, $(C_1-C_6)$alkylaminothiocarbonyl, di$(C_1-C_6)$alkylaminothiocarbonyl, $(C_3-C_8)$cycloalkylamino, $(C_1-C_6)$alkylcarbamoyl (including —NHCOO$(C_1-C_6)$alkyl, —N$(C_1-C_6)$alkyl-COO$(C_1-C_6)$alkyl, —OCONH$(C_1-C_6)$alkyl or —OCON$(C_1-C_6)$dialkyl), $(C_1-C_6)$alkylcarbonylamino ($(C_1-C_6)$alkylCONH), $(C_1-C_6)$alkylurea (including —NHCONH$(C_1-C_6)$alkyl, and —NHCON$(C_1-C_6)$dialkyl) or is in each case optionally singly or multiply, identically or differently substituted aryl or hetaryl, where (in the case of hetaryl) at least one carbonyl group may optionally be present and where possible substituents in each case are as follows: cyano, carboxyl, halogen, nitro, hydroxyl, amino, tri-$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di$(C_1-C_6)$alkylaminocarbonyl, $(C_2-C_6)$alkenylaminocarbonyl, di$(C_2-C_6)$alkenylaminocarbonyl, $(C_3-C_8)$cycloalkylaminocarbonyl, $(C_1-C_6)$alkylsulfonylamino, $(C_1-C_6)$alkylamino, di$(C_1-C_6)$alkylamino, aminosulfonyl, $(C_1-C_6)$alkylaminosulfonyl, di$(C_1-C_6)$alkylaminosulfonyl, $(C_1-C_6)$alkylsulfoximino, aminothiocarbonyl, $(C_1-C_6)$alkylaminothiocarbonyl, di$(C_1-C_6)$alkylaminothiocarbonyl, $(C_3-C_8)$cycloalkylamino or $(C_1-C_6)$alkylcarbonylamino, where only one or two of the $R^{10}$, $R^{11}$, $R^{12}$, $R^{13}$, $R^{14}$, $R^{15}$, $R^{16}$ and $R^{17}$ radicals are a substituent other than hydrogen, and, if any of $R^{10}$ and $R^{14}$, $R^{11}$ and $R^{15}$, $R^{12}$ and $R^{16}$ or $R^{13}$ and $R^{17}$ are both not hydrogen, $R^{14}$, $R^{15}$, $R^{16}$ and $R^{17}$ are each independently only cyano, halogen, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl or $(C_1-C_6)$cyanoalkyl, Q is a partly saturated or saturated heterocyclic or heteroaromatic 8-, 9-, 11- or 12-membered fused bicyclic or tricyclic ring system, where at least one carbonyl group may optionally be present and where the ring system may optionally be mono- or polysubstituted identically or differently, and where the substituents may independently be selected from cyano, halogen, nitro, hydroxyl, amino, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$alkynyloxy-$(C_1-C_4)$alkyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$haloalkoxy-$(C_1-C_6)$alkyl, $(C_2-C_6)$alkenyloxy-$(C_1-C_6)$alkyl, $(C_2-C_6)$haloalkenyloxy-$(C_1-C_6)$alkyl, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkyl sulfinyl, $(C_1-C_6)$haloalkyl sulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkyl sulfonyl, $(C_1-C_6)$haloalkyl sulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$alkylcarbonyl-$(C_1-C_6)$alkyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di$(C_1-C_6)$alkylaminocarbonyl, di$(C_1-C_6)$alkylaminothiocarbonyl, $(C_2-C_6)$alkenylaminocarbonyl, di$(C_2-C_6)$alkenylaminocarbonyl, $(C_3-C_8)$cycloalkylaminocarbonyl, $(C_1-C_6)$alkyl sulfonylamino, $(C_1-C_6)$alkylamino, di$(C_1-C_6)$alkylamino, aminosulfonyl, $(C_1-C_6)$alkylaminosulfonyl, di$(C_1-C_6)$alkylaminosulfonyl, $(C_1-C_6)$alkyl sulfoximino, aminothiocarbonyl, $(C_1-C_6)$alkylaminothiocarbonyl, di$(C_1-C_6)$alkylaminothiocarbonyl, $(C_3-C_8)$cycloalkylamino or $(C_1-C_6)$alkylcarbonylamino or where the substituents may independently be selected from phenyl or a 5- or 6-membered heteroaromatic ring, where phenyl or the ring may optionally be mono- or polysubstituted identically or differently by $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, $C_1-C_4$-alkoxy, $C_1-C_4$-haloalkoxy, n is 0, 1 or 2.

2. The compound of formula (Ia) or (Ib) according to claim 1, in which, if ⫽ represent exclusively double bonds and hence Aa to Ad together with the carbon atoms adjacent to Aa and Ad in each case form an aromatic ring, Aa is nitrogen or C($R^{10}$), Ab is nitrogen or C($R^{11}$), Ac is nitrogen or C($R^{12}$), and Ad is nitrogen or C($R^{13}$), where not more than two of Aa, Ab, Ac and Ad are nitrogen, or, if ⫽ represent exclusively single bonds, Aa is C($R^{10}$)($R^{14}$), Ab is C($R^{11}$)($R^{15}$), Ac is C(R$^{12}$)(R$^{16}$) and
Ad is C(R$^{13}$)(R$^{17}$),
R$^1$ is (C$_1$-C$_4$)alkyl, (C$_1$-C$_4$)hydroxyalkyl, (C$_1$-C$_4$)haloalkyl, (C$_1$-C$_4$)cyanoalkyl, (C$_1$-C$_4$)alkoxy-(C$_1$-C$_4$)alkyl, (C$_1$-C$_4$)haloalkoxy-(C$_1$-C$_4$)alkyl, (C$_2$-C$_4$)alkenyl, (C$_2$-C$_4$)alkenyloxy-(C$_1$-C$_4$)alkyl, (C$_2$-C$_4$)haloalkenyloxy-(C$_1$-C$_4$)alkyl, (C$_2$-C$_4$)haloalkenyl, (C$_2$-C$_4$)cyanoalkenyl, (C$_2$-C$_4$)alkynyl, (C$_2$-C$_4$)alkynyloxy-(C$_1$-C$_4$)alkyl, (C$_2$-C$_4$)haloalkynyloxy-(C$_1$-C$_4$)alkyl, (C$_2$-C$_4$)haloalkynyl, (C$_2$-C$_4$)cyanoalkynyl, (C$_3$-C$_6$)cycloalkyl, (C$_3$-C$_6$)cycloalkyl(C$_3$-C$_6$)cycloalkyl, (C$_1$-C$_4$)alkyl-(C$_3$-C$_6$)cycloalkyl, halo(C$_3$-C$_6$)cycloalkyl, (C$_1$-C$_4$)alkylamino, di(C$_1$-C$_4$)alkylamino, (C$_3$-C$_6$)cycloalkylamino, (C$_1$-C$_4$)alkylcarbonylamino, (C$_1$-C$_4$)alkylthio-(C$_1$-C$_4$)alkyl, (C$_1$-C$_4$)haloalkylthio-(C$_1$-C$_4$)alkyl, (C$_1$-C$_4$)alkylsulfinyl-(C$_1$-C$_4$)alkyl, (C$_1$-C$_4$)haloalkylsulfinyl-(C$_1$-C$_4$)alkyl, (C$_1$-C$_4$)alkylsulfonyl-(C$_1$-C$_4$)alkyl, (C$_1$-C$_4$)alkylcarbonyl-(C$_1$-C$_4$)alkyl, (C$_1$-C$_4$)haloalkylcarbonyl-(C$_1$-C$_4$)alkyl or (C$_1$-C$_4$)alkylsulfonylamino, R$^{10}$, R$^{11}$, R$^{12}$, R$^{13}$, R$^{14}$, R$^{15}$, R$^{16}$, R$^{17}$ are independently hydrogen, cyano, halogen, nitro, hydroxyl, amino, tri(C$_1$-C$_4$)alkylsilyl, (C$_3$-C$_6$)cycloalkyl, (C$_3$-C$_6$)cycloalkyl-(C$_3$-C$_6$)cycloalkyl, (C$_1$-C$_4$)alkyl-(C$_3$-C$_6$)cycloalkyl, halo(C$_3$-C$_6$)cycloalkyl, (C$_1$-C$_4$)alkyl, (C$_1$-C$_4$)haloalkyl, (C$_1$-C$_4$)cyanoalkyl, (C$_1$-C$_4$)hydroxyalkyl, (C$_1$-C$_4$)alkoxy-(C$_1$-C$_4$)alkyl, (C$_2$-C$_4$)alkenyl, (C$_2$-C$_4$)haloalkenyl, (C$_2$-C$_4$)cyanoalkenyl, (C$_2$-C$_4$)alkynyl, (C$_2$-C$_4$)haloalkynyl, (C$_2$-C$_4$)cyanoalkynyl, (C$_1$-C$_4$)alkoxy, (C$_1$-C$_4$)haloalkoxy, (C$_1$-C$_4$)cyanoalkoxy, (C$_1$-C$_4$)alkoxy-(C$_1$-C$_4$)alkoxy, (C$_1$-C$_4$)alkylhydroxyimino, (C$_1$-C$_4$)alkoxyimino, (C$_1$-C$_4$)alkyl-(C$_1$-C$_4$)alkoxyimino, (C$_1$-C$_4$)haloalkyl-(C$_1$-C$_4$)alkoxyimino, (C$_1$-C$_4$)alkylthio, (C$_1$-C$_4$)haloalkylthio, (C$_1$-C$_4$)alkylthio-(C$_1$-C$_4$)alkyl, (C$_1$-C$_4$)alkylsulfinyl, (C$_1$-C$_4$)haloalkylsulfinyl, (C$_1$-C$_4$)alkylsulfinyl-(C$_1$-C$_4$)alkyl, (C$_1$-C$_4$)alkylsulfonyl, (C$_1$-C$_4$)haloalkylsulfonyl, (C$_1$-C$_4$)alkylsulfonyl-(C$_1$-C$_4$)alkyl, (C$_1$-C$_4$)alkylsulfonyloxy, (C$_1$-C$_4$)alkylcarbonyl, (C$_1$-C$_4$)haloalkylcarbonyl, aminocarbonyl, aminothiocarbonyl, (C$_1$-C$_4$)alkylaminocarbonyl, di(C$_1$-C$_4$)alkylaminocarbonyl, (C$_3$-C$_6$)cycloalkylaminocarbonyl, (C$_1$-C$_4$)alkylsulfonylamino, (C$_1$-C$_4$)alkylamino, di(C$_1$-C$_4$)alkylamino, aminosulfonyl, (C$_1$-C$_4$)alkylaminosulfonyl, di(C$_1$-C$_4$)alkylaminosulfonyl, aminothiocarbonyl, (C$_1$-C$_4$)alkylcarbamoyl (including —NHCOO(C$_1$-C$_4$)alkyl, —N(C$_1$-C$_4$)alkyl-COO(C$_1$-C$_4$)alkyl, —OCONH(C$_1$-C$_4$)alkyl or —OCON(C$_1$-C$_4$)dialkyl), (C$_1$-C$_4$)alkylcarbonylamino, (C$_1$-C$_4$)alkylurea (including —NHCONH(C$_1$-C$_4$)alkyl, and —NHCON(C$_1$-C$_4$)dialkyl)

or are phenyl or hetaryl, each of which is optionally mono- or disubstituted identically or differently, where (in the case of hetaryl) at least one carbonyl group may optionally be present and where possible substituents are in each case as follows: cyano, halogen, nitro, acetyl, amino, (C$_3$-C$_6$)cycloalkyl, (C$_3$-C$_6$)cycloalkyl-(C$_3$-C$_6$)cycloalkyl, (C$_1$-C$_4$)alkyl-(C$_3$-C$_6$)cycloalkyl, halo(C$_3$-C$_6$)cycloalkyl, (C$_1$-C$_4$)alkyl, (C$_1$-C$_4$)haloalkyl, (C$_1$-C$_4$)cyanoalkyl, (C$_1$-C$_4$)hydroxyalkyl, (C$_1$-C$_4$)alkoxy-(C$_1$-C$_4$)alkyl, (C$_2$-C$_4$)alkenyl, (C$_2$-C$_4$)haloalkenyl, (C$_2$-C$_4$)cyanoalkenyl, (C$_2$-C$_4$)alkynyl, (C$_2$-C$_4$)haloalkynyl, (C$_2$-C$_4$)cyanoalkynyl, (C$_1$-C$_4$)alkoxy, (C$_1$-C$_4$)haloalkoxy, (C$_1$-C$_4$)cyanoalkoxy, (C$_1$-C$_4$)alkoxy-(C$_1$-C$_4$)alkoxy, (C$_1$-C$_4$)alkylhydroxyimino, (C$_1$-C$_4$)alkoxyimino, (C$_1$-C$_4$)alkyl-(C$_1$-C$_4$)alkoxyimino, (C$_1$-C$_4$)haloalkyl-(C$_1$-C$_4$)alkoxyimino, (C$_1$-C$_4$)alkylthio, (C$_1$-C$_4$)haloalkylthio, (C$_1$-C$_4$)alkylthio-(C$_1$-C$_4$)alkyl, (C$_1$-C$_4$)alkylsulfinyl, (C$_1$-C$_4$)haloalkylsulfinyl, (C$_1$-C$_4$)alkylsulfinyl-(C$_1$-C$_4$)alkyl, (C$_1$-C$_4$)alkylsulfonyl, (C$_1$-C$_4$)haloalkylsulfonyl, (C$_1$-C$_4$)alkylsulfonyl-(C$_1$-C$_4$)alkyl, (C$_1$-C$_4$)alkylsulfonyloxy, (C$_1$-C$_4$)alkylcarbonyl, (C$_1$-C$_4$)haloalkylcarbonyl, aminocarbonyl, (C$_1$-C$_4$)alkylaminocarbonyl, di(C$_1$-C$_4$)alkylaminocarbonyl, (C$_1$-C$_4$)alkylsulfonylamino, (C$_1$-C$_4$)alkylamino, di(C$_1$-C$_4$)alkylamino, aminosulfonyl, (C$_1$-C$_4$)alkylaminosulfonyl, di(C$_1$-C$_4$)alkylaminosulfonyl or (C$_1$-C$_4$)alkylcarbonylamino, where only one or two of the R$^{10}$, R$^{11}$, R$^{12}$, R$^{13}$, R$^{14}$, R$^{15}$, R$^{16}$, R$^{17}$ radicals are a substituent other than hydrogen, and, if any of R$^{10}$ and R$^{14}$, R$^{11}$ and R$^{15}$, R$^{12}$ and R$^{16}$ or R$^{13}$ and R$^{17}$ are both not hydrogen, R$^{14}$, R$^{15}$, R$^{16}$ and R$^{17}$ are each independently only cyano, halogen, (C$_3$-C$_6$)cycloalkyl, (C$_3$-C$_6$)cycloalkyl-(C$_3$-C$_6$)cycloalkyl, (C$_1$-C$_4$)alkyl-(C$_3$-C$_6$)cycloalkyl, halo(C$_3$-C$_6$)cycloalkyl, (C$_1$-C$_4$)alkyl, (C$_1$-C$_4$)haloalkyl or (C$_1$-C$_4$)cyanoalkyl, Q is a heteroaromatic 9-membered or 12-membered fused bicyclic or tricyclic ring system from the group of Q1 to Q15:

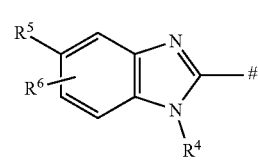

Q1

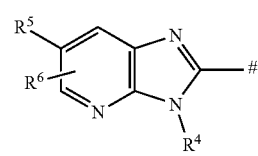

Q2

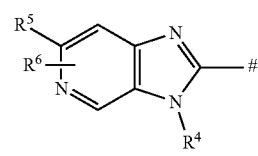

Q3

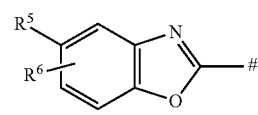

Q4

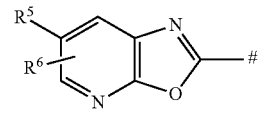

Q5

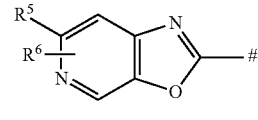

Q6

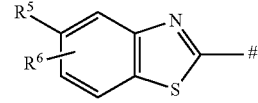

Q7

-continued

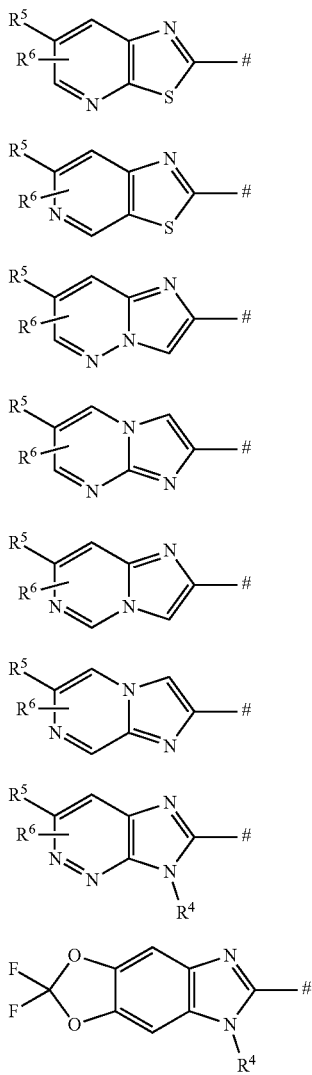

where
R⁴ is hydrogen, (C₁-C₄)alkyl, (C₁-C₄)haloalkyl, (C₁-C₄)cyanoalkyl, (C₁-C₄)hydroxyalkyl, (C₁-C₄)alkoxy-(C₁-C₄)alkyl, (C₁-C₄)haloalkoxy-(C₁-C₄)alkyl, (C₂-C₄)alkenyl, (C₂-C₄)alkenyloxy-(C₁-C₄)alkyl, (C₂-C₄)haloalkenyloxy-(C₁-C₄)alkyl, (C₂-C₄)haloalkenyl, (C₂-C₄)cyanoalkenyl, (C₂-C₄)alkynyl, (C₂-C₄)haloalkynyl or (C₃-C₆)cycloalkyl and R⁵, R⁶ are independently hydrogen, cyano, halogen, (C₁-C₄)alkyl, (C₁-C₄)haloalkyl, (C₂-C₄)alkenyl, (C₂-C₄)haloalkenyl, (C₂-C₄)alkynyl, (C₂-C₄)haloalkynyl, (C₃-C₆)cycloalkyl, (C₃-C₆)cycloalkyl-(C₃-C₆)cycloalkyl, (C₁-C₄)alkyl-(C₃-C₆)cycloalkyl, (C₁-C₄)haloalkyl-(C₃-C₆)cycloalkyl, cyano-(C₃-C₆)cycloalkyl, halo-(C₃-C₆)cycloalkyl, (C₁-C₄)alkoxy, (C₁-C₄)haloalkoxy, (C₁-C₄)alkoxyimino, (C₁-C₄)haloalkoxyimino, (C₁-C₄)alkylthio, (C₁-C₄)haloalkylthio, (C₁-C₄)alkylsulfinyl, (C₁-C₄)haloalkylsulfinyl, (C₁-C₄)alkylsulfonyl, (C₁-C₄)haloalkylsulfonyl, (C₁-C₄)alkylsulfonyloxy, (C₁-C₄)haloalkylsulfonyloxy, (C₁-C₄)alkylcarbonyl, (C₁-C₄)haloalkylcarbonyl, aminocarbonyl, (C₁-C₄)alkylaminocarbonyl, di(C₁-C₄)alkylaminocarbonyl, (C₁-C₄)alkylsulfonylamino, (C₁-C₄)alkylamino, di(C₁-C₄)alkylamino, aminosulfonyl, (C₁-C₄)alkylaminosulfonyl or di(C₁-C₄)alkylaminosulfonyl and
n is 0, 1 or 2.

3. The compound of formula (Ia) or (Ib) according to claim 2,
in which,
if ⁄⁄ represent exclusively double bonds and hence Aa to Ad together with the carbon atoms adjacent to Aa and Ad in each case form an aromatic ring,
Aa is nitrogen or C(R¹⁰),
Ab is nitrogen or C(R¹¹),
Ac is nitrogen or C(R¹²), and
Ad is nitrogen or C(R¹³),
where not more than two of Aa, Ab, Ac and Ad are nitrogen,
or, if ⁄⁄ represent exclusively single bonds,
Aa is C(R¹⁰)(R¹⁴),
Ab is C(R)(R¹⁵),
Ac is C(R¹²)(R¹⁶) and
Ad is C(R¹³)(R¹⁷),
R¹ is (C₁-C₄)alkyl, (C₁-C₄)hydroxyalkyl, (C₁-C₄)haloalkyl, (C₂-C₄)alkenyl, (C₂-C₄)haloalkenyl, (C₂-C₄)alkynyl, (C₂-C₄)haloalkynyl, (C₃-C₆)cycloalkyl, (C₁-C₄)alkylthio-(C₁-C₄)alkyl, (C₁-C₄)alkylsulfinyl-(C₁-C₄)alkyl or (C₁-C₄)alkylsulfonyl-(C₁-C₄)alkyl,
R¹⁰, R¹¹, R¹², R¹³, R¹⁴, R¹⁵, R¹⁶, R¹⁷ are independently hydrogen, cyano, halogen, nitro, hydroxyl, amino, tri(C₁-C₄)alkylsilyl, (C₃-C₆)cycloalkyl, (C₃-C₆)cycloalkyl-(C₃-C₆)cycloalkyl, (C₁-C₄)alkyl-(C₃-C₆)cycloalkyl, halo(C₃-C₆)cycloalkyl, (C₁-C₄)alkyl, (C₁-C₄)haloalkyl, (C₁-C₄)cyanoalkyl, (C₁-C₄)alkoxy-(C₁-C₄)alkyl, (C₂-C₄)alkenyl, (C₂-C₄)haloalkenyl, (C₂-C₄)cyanoalkenyl, (C₂-C₄)alkynyl, (C₂-C₄)haloalkynyl, (C₂-C₄)cyanoalkynyl, (C₁-C₄)alkoxy, (C₁-C₄)haloalkoxy, (C₁-C₄)cyanoalkoxy, (C₁-C₄)alkylthio, (C₁-C₄)haloalkylthio, (C₁-C₄)alkylsulfinyl, (C₁-C₄)haloalkylsulfinyl, (C₁-C₄)alkylsulfonyl, (C₁-C₄)haloalkylsulfonyl, (C₁-C₄)alkylsulfonyloxy, (C₁-C₄)alkylcarbonyl, (C₁-C₄)haloalkylcarbonyl, aminocarbonyl, (C₁-C₄)alkylaminocarbonyl, di(C₁-C₄)alkylaminocarbonyl, (C₃-C₆)cycloalkylaminocarbonyl, (C₁-C₄)alkylsulfonylamino, (C₁-C₄)alkylamino, di(C₁-C₄)alkylamino, aminosulfonyl, (C₁-C₄)alkylaminosulfonyl, di(C₁-C₄)alkylaminosulfonyl, (C₁-C₄)alkylcarbamoyl (including —NHCOO(C₁-C₄)alkyl and —N(C₁-C₄)alkylCOO(C₁-C₄)alkyl), (C₁-C₄)alkylcarbonylamino, (C₁-C₄)alkylurea (including —NHCONH(C₁-C₄)alkyl and —NHCON(C₁-C₄)dialkyl) or are phenyl or hetaryl, each of which is optionally mono- or disubstituted identically or differently, where (in the case of hetaryl) at least one carbonyl group may optionally be present and where possible substituents are in each case as follows: cyano, halogen, (C₃-C₆)cycloalkyl, (C₃-C₆)cycloalkyl-(C₃-C₆)cycloalkyl, (C₁-C₄)alkyl-(C₃-C₆)cycloalkyl, halo(C₃-C₆)cycloalkyl, (C₁-C₄)alkyl, (C₁-C₄)haloalkyl, (C₁-C₄)cyanoalkyl, (C₂-C₄)alkenyl, (C₂-C₄)haloalkenyl, (C₂-C₄)cyanoalkenyl, (C₂-C₄)alkynyl, (C₂-C₄)haloalkynyl, (C₂-C₄)cyanoalkynyl, (C₁-C₄)alkoxy, (C₁-C₄)haloalkoxy, (C₁-C₄)alkylthio, (C₁-C₄)haloalkylthio, (C₁-C₄)alkylsulfinyl, (C₁-C₄)haloalkylsulfinyl, (C₁-C₄)alkylsulfonyl, (C₁-C₄)haloalkylsulfonyl, (C₁-C₄)alkylsulfonyloxy, (C₁-C₄)alkylcarbonyl, (C₁-C₄)haloalkylcarbonyl, aminocarbonyl, (C₁-C₄)alkylaminocarbonyl, di(C₁-C₄)alkylaminocarbonyl, (C₁-C₄)alkylsulfonylamino, (C₁-C₄)alkylamino, di(C₁-C₄)alkylamino, aminosulfonyl, ($C_1$-$C_4$)alkylaminosulfonyl, di($C_1$-$C_4$)alkylaminosulfonyl, ($C_1$-$C_4$)alkylcarbonylamino,
where only one or two of the $R^{10}$, $R^{11}$, $R^{12}$, $R^{13}$, $R^{14}$, $R^{15}$, $R^{16}$, $R^{17}$ radicals are a substituent other than hydrogen,
and, if any of $R^{10}$ and $R^{14}$, $R^{11}$ and $R^{15}$, $R^{12}$ and $R^{16}$ or $R^{13}$ and $R^{17}$ are both not hydrogen, $R^{14}$, $R^{15}$, $R^{16}$ and $R^{17}$ are each independently only cyano, halogen, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl or ($C_1$-$C_4$)cyanoalkyl, Q is a heteroaromatic 9-membered or 12-membered fused bicyclic or tricyclic ring system from the group of Q1 to Q15,
where
$R^4$ is hydrogen, ($C_1$-$C_4$)alkyl, ($C_3$-$C_6$)cycloalkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)haloalkenyl, ($C_2$-$C_4$)alkynyl or ($C_2$-$C_4$)haloalkynyl and
$R^5$, $R^6$ are independently hydrogen, cyano, halogen, ($C_1$-$C_4$)alkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)haloalkyl-($C_3$-$C_6$)cycloalkyl, cyano-($C_3$-$C_6$)cycloalkyl, halo($C_3$-$C_6$)cycloalkyl, ($C_1$-$C_4$)alkoxy, ($C_1$-$C_4$)haloalkoxy, ($C_1$-$C_4$)alkoxyimino, ($C_1$-$C_4$)haloalkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)haloalkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl or di($C_1$-$C_4$)alkylaminosulfonyl
and
n is 0, 1 or 2.

4. The compound of formula (Ia) or (Ib) according to claim 2,
in which,
if ⫽ represent exclusively double bonds and hence Aa to Ad together with the carbon atoms adjacent to Aa and Ad in each case form an aromatic ring,
Aa is nitrogen or C($R^{10}$),
Ab is nitrogen or C($R^1$),
Ac is nitrogen or C($R^{12}$), and
Ad is nitrogen or C($R^{13}$),
where not more than two of Aa, Ab, Ac and Ad are nitrogen,
or, if ⫽ represent exclusively single bonds,
Aa is C($R^{10}$)($R^{14}$),
Ab is C($R^1$)($R^{15}$),
Ac is C($R^{12}$)($R^{16}$) and
Ad is C($R^{13}$)($R^{17}$),
$R^1$ is methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl,
$R^{10}$, $R^{11}$, $R^{12}$, $R^{13}$, $R^{14}$, $R^{15}$, $R^{16}$, $R^{17}$ are independently hydrogen, cyano, halogen, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)alkylsulfinyl, ($C_1$-$C_4$)alkyl sulfonyl, ($C_1$-$C_4$)haloalkylthio, ($C_1$-$C_4$)haloalkylsulfinyl, ($C_1$-$C_4$)haloalkylsulfonyl, aminocarbonyl, ($C_1$-$C_4$)alkylaminocarbonyl, ($C_3$-$C_6$)cycloalkylaminocarbonyl, ($C_1$-$C_4$)alkylcarbamoyl (including —NHCOO($C_1$-$C_4$)alkyl and —N($C_1$-$C_4$)alkylCOO($C_1$-$C_4$)alkyl), ($C_1$-$C_4$)alkylcarbonylamino or ($C_1$-$C_4$)alkylurea (including —NHCONH($C_1$-$C_4$)alkyl and —NHCON($C_1$-$C_4$)dialkyl),
where only one or two of the $R^{10}$, $R^{11}$, $R^{12}$, $R^{13}$, $R^{14}$, $R^{15}$, $R^{16}$, $R^{17}$ radicals are a substituent other than hydrogen,
and, if any of $R^{10}$ and $R^{14}$, $R^{11}$ and $R^{15}$, $R^{12}$ and $R^{16}$ or $R^{13}$ and $R^{17}$ are both not hydrogen, $R^{14}$, $R^{15}$, $R^{16}$ and $R^{17}$ are each independently only cyano, halogen, ($C_1$-$C_4$)alkyl or ($C_1$-$C_4$)haloalkyl,
Q is a heteroaromatic 9-membered or 12-membered fused bicyclic or tricyclic ring system from the group of Q1, Q2, Q3, Q5, Q6, Q8, Q9, Q14 or Q15,
where
$R^4$ is ($C_1$-$C_4$)alkyl, ($C_1$-$C_4$)haloalkyl, ($C_3$-$C_6$)cycloalkyl or ($C_1$-$C_4$)alkoxy-($C_1$-$C_4$)alkyl,
$R^5$ is cyano, halogen, ($C_1$-$C_4$)haloalkyl, halo-($C_3$-$C_6$)cycloalkyl, ($C_1$-$C_4$)haloalkoxy, ($C_1$-$C_4$)haloalkylthio, ($C_1$-$C_4$)haloalkylsulfinyl, ($C_1$-$C_4$)alkylsulfonyl, ($C_1$-$C_4$)haloalkylsulfonyl, ($C_1$-$C_4$)haloalkylcarbonyl or ($C_1$-$C_4$)haloalkylsulfonyloxy,
$R^6$ is hydrogen, cyano, halogen, ($C_1$-$C_4$)alkyl, ($C_1$-$C_4$)haloalkyl or ($C_3$-$C_6$)cycloalkyl and
n is 0, 1 or 2.

5. The compound of formula (Ia) or (Ib) according to claim 2,
in which,
if ⫽ represent exclusively double bonds and hence Aa to Ad together with the carbon atoms adjacent to Aa and Ad in each case form an aromatic ring,
Aa is C($R^{10}$),
Ab is C($R^{11}$),
Ac is C($R^{12}$) and
Ad is C($R^{13}$),
or, if ⫽ represent exclusively single bonds,
Aa is C($R^{10}$)($R^{14}$),
Ab is C($R^{11}$)($R^{15}$),
Ac is C($R^{12}$)($R^{16}$) and
Ad is C($R^{13}$)($R^{17}$),
$R^1$ is ethyl,
$R^{10}$, $R^{11}$, $R^{12}$, $R^{13}$ are independently hydrogen, fluorine, chlorine, bromine, iodine, cyano, methyl, ethyl, trifluoromethyl, trifluoromethoxy, 2,2,2-trifluoroethoxy, acetylamino (methylcarbonylamino), cyclopropylamido (cyclopropylaminocarbonyl), methylcarbamoyl (—NHCOOMe), methylurea (—NHCONHMe) or cyclopropyl,
where only one or two of the $R^{10}$, $R^{11}$, $R^{12}$, $R^{13}$ radicals are a substituent other than hydrogen,
$R^{14}$, $R^{15}$, $R^{16}$, $R^{17}$ are independently hydrogen or ($C_1$-$C_4$)alkyl,
Q is a heteroaromatic 9-membered fused bicyclic ring system from the group of Q2, Q3 and Q14

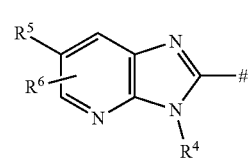

Q2

-continued

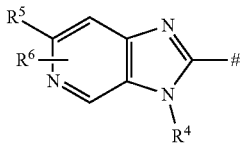
Q3

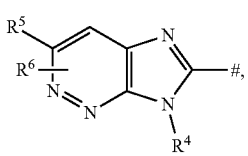
Q14 where
R⁴ is methyl,
R⁵ is trifluoromethyl or pentafluoroethyl,
R⁶ is hydrogen and
n is 0, 1 or 2.

6. The compound of formula (Ia) or (Ib) according to claim 2,
in which,
if ⁓ represent exclusively double bonds and hence Aa to Ad together with the carbon atoms adjacent to Aa and Ad in each case form an aromatic ring,
Aa is C(R¹⁰),
Ab is nitrogen or C(R¹¹),
Ac is C(R¹²) and
Ad is C(R¹³), where
R¹⁰ is hydrogen, chlorine or trifluoromethyl,
R¹¹ is hydrogen, chlorine, —NHCOMe or trifluoromethyl,
R¹² is hydrogen, chlorine or trifluoromethyl,
R¹³ is hydrogen, chlorine or trifluoromethyl,
or, if ⁓ represent exclusively single bonds,
Aa is C(R¹⁰)(R¹⁴),
Ab is C(R¹¹)(R¹⁵),
Ac is C(R¹²)(R¹⁶) and
Ad is C(R¹³)(R¹⁷), where
R¹⁰, R¹², R¹³, R¹⁴, R¹⁶, R¹⁷ are hydrogen,
R¹¹ is hydrogen or methyl and
R¹⁵ is hydrogen or methyl,
R¹ is ethyl,
Q is a heteroaromatic 9-membered fused bicyclic ring system from the group of Q2 and Q3

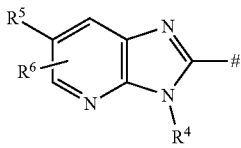
Q2

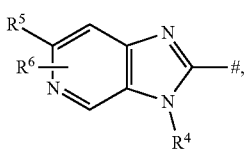
Q3 where
R⁴ is methyl,
R⁵ is trifluoromethyl or pentafluoroethyl,
R⁶ is hydrogen and
n is 0, 1 or 2.

7. The compound of formula (Ia) or (Ib) according to claim 2,
in which
Q is Q2, Q3, Q5, Q6, Q8, Q9, Q14 or Q15,
where
R⁴ is (C₁-C₄)alkyl, (C₁-C₄)haloalkyl, (C₃-C₆)cycloalkyl or (C₁-C₄)alkoxy-(C₁-C₄)alkyl,
R⁵ is cyano, halogen, (C₁-C₄)haloalkyl, halo-(C₃-C₆)cycloalkyl, (C₁-C₄)haloalkoxy, (C₁-C₄)haloalkylthio, (C₁-C₄)haloalkylsulfinyl, (C₁-C₄)alkylsulfonyl, (C₁-C₄)haloalkylsulfonyl, (C₁-C₄)haloalkylcarbonyl or (C₁-C₄)haloalkylsulfonyloxy,
R⁶ is hydrogen, cyano, halogen, (C₁-C₄)alkyl, (C₁-C₄)haloalkyl or (C₃-C₆)cycloalkyl and and Aa, Ab, Ac, Ad, R¹, R¹⁰ R¹¹, R¹², R¹³, R¹⁴, R¹⁵, R¹⁶, R¹⁷ and n have the definitions according to claim 2.

8. The compound of formula (Ia) or (Ib) according to claim 2,
in which
Q is Q2, Q3 or Q14

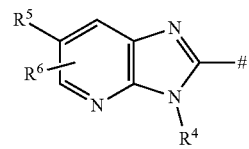
Q2

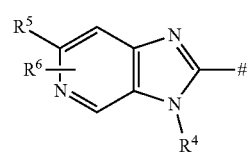
Q3

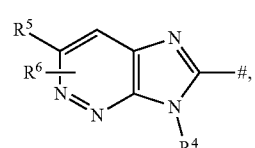
Q14 where
R⁴ is methyl,
R⁵ is trifluoromethyl or pentafluoroethyl,
R⁶ is hydrogen
and Aa, Ab, Ac, Ad, R¹, R¹⁰ R¹¹, R¹², R¹³, R¹⁴, R¹⁵, R¹⁶, R¹⁷ and n have the definitions according to claim 2.

9. The compound of formula (Ia) or (Ib) according to claim 2,
in which
Q is Q2 or Q3

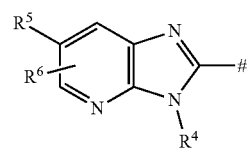
Q2

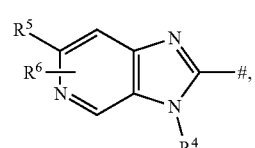
Q3 where

R⁴ is methyl,

R⁵ is trifluoromethyl or pentafluoroethyl,

R⁶ is hydrogen and Aa, Ab, Ac, Ad, R¹, R¹⁰ R¹¹, R¹², R¹³, R¹⁴, R¹⁵, R¹⁶, R¹⁷ and n have the definitions according to claim 2.

10. The compound of formula (Ia) or (Ib) according to claim 2, in which R¹ is ethyl and Aa, Ab, Ac, Ad, R¹⁰ R¹¹, R¹², R¹³, R¹⁴, R¹⁵, R¹⁶, R¹⁷ Q, R⁴, R⁵, R⁶ and n have the definitions according to claim 2.

11. The compound of formula (Ia) or (Ib) according to claim 2, where the formulae (Ia) and (Ib) give rise to the following structures (Ia1) to (Ia4) and (Ib1)

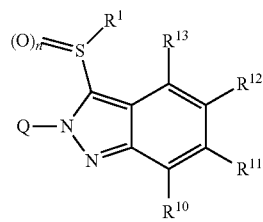
(Ia1)

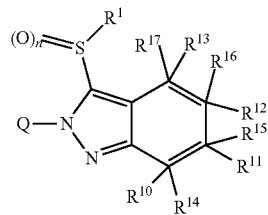
(Ia2)

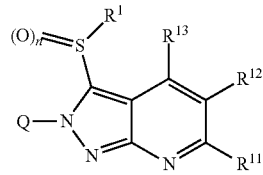
(Ia3)

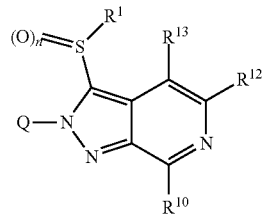
(Ia4)

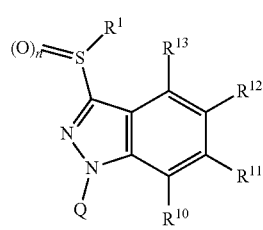
(Ib1)

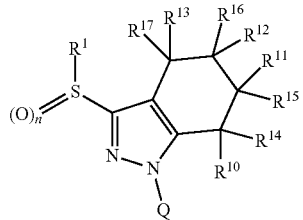
(Ib2)

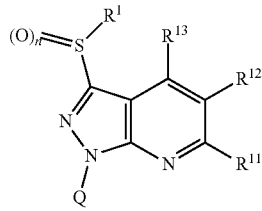
(Ib3)

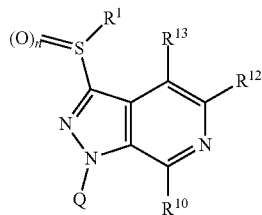
(Ib4)

where R¹, R¹⁰, R¹¹, R¹², R¹³, R¹⁴, R¹⁵, R¹⁶, R¹⁷, Q, R⁴, R⁵, R⁶ and n have the definitions described in claim 2.

12. A compound selected from the group consisting of

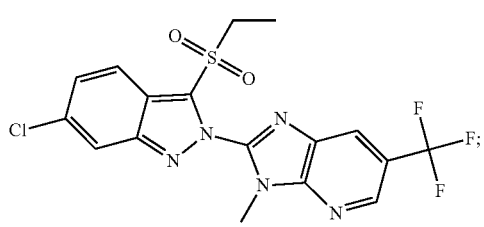
I-1

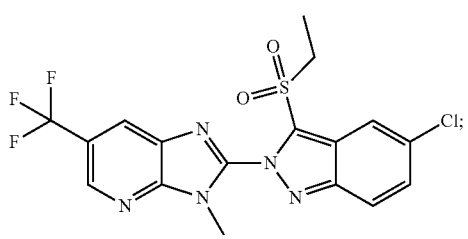
I-2

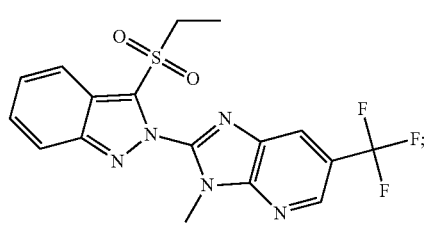
I-3

-continued

-continued

I-17
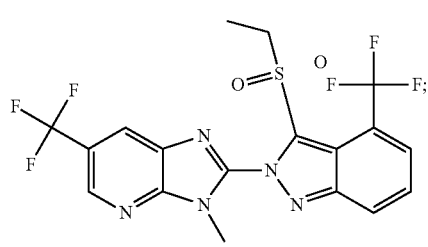

I-18
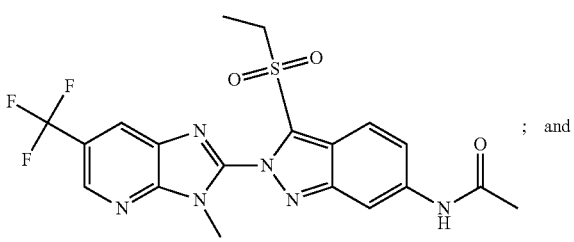
; and

I-19
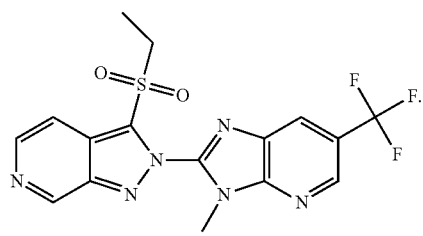

13. The compound of formula (Ia) or (Ib) according to claim 1, characterized in that, if for the compound of the formula (Ia)

⚞ represents exclusively double bonds, $R^1$ is $C_1$-$C_6$ alkyl,

Aa and Ad are CH,

Ab is $C(R^{11})$,

Ac is $C(R^{12})$ and

Q is Q2

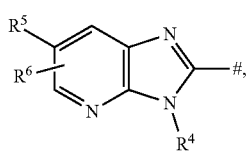

Q2 where $R^4$ is $C_1$-$C_6$ alkyl, $R^6$ is hydrogen and $R^5$ is $(C_1$-$C_6)$haloalkyl, $(C_1$-$C_6)$haloalkylthio, $(C_1$-$C_6)$haloalkylsulfinyl or $(C_1$-$C_6)$haloalkylsulfonyl, at least one of the radicals $R^{11}$ or $R^{12}$ is not hydrogen, halogen or $(C_1$-$C_6)$haloalkyl.

14. A compound of formulae (Ia) or (Ib) according to claim 1, characterized in that, if for the compound of the formula (Ia)

⚞ represents exclusively double bonds, $R^1$ is $C_1$-$C_6$ alkyl,

Aa and Ad are CH,

Ab is $C(R^{11})$,

Ac is $C(R^{12})$ $R^{11}$ and $R^{12}$ are independently hydrogen, halogen or $(C_1$-$C_6)$haloalkyl and Q is Q2

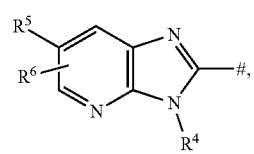

Q2 where $R^4$ is $C_1$-$C_6$ alkyl and $R^6$ is hydrogen, $R^5$ is not $(C_1$-$C_6)$haloalkyl, $(C_1$-$C_6)$haloalkylthio, $(C_1$-$C_6)$haloalkylsulfinyl or $(C_1$-$C_6)$haloalkylsulfonyl.

15. The compound of formula (Ia) or (Ib) according to claim 1, wherein the compound is not a compound of formula (Y)

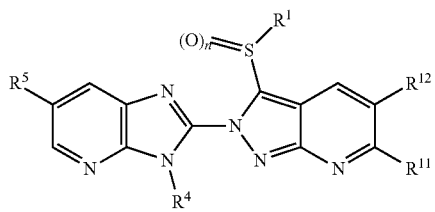

(Y)

in which $R^1$ is $(C_1$-$C_6)$alkyl, $R^4$ is $(C_1$-$C_6)$alkyl, $R^5$ is $(C_1$-$C_6)$haloalkyl, $(C_1$-$C_6)$haloalkylthio, $(C_1$-$C_6)$haloalkylsulfinyl or $(C_1$-$C_6)$haloalkylsulfonyl, $R^{11}$ and $R^{12}$ are independently each hydrogen, halogen or $(C_1$-$C_6)$ haloalkyl and n is 0, 1 or 2.

16. The compound of formula (Ia) according to claim 1, characterized in that ⚞ represents exclusively single bonds.

17. An agrochemical formulation comprising at least one compound of formula (Ia) or (Ib) according to claim 1 and also extenders and/or surfactants.

18. The agrochemical formulation according to claim 17, additionally comprising a further agrochemically active ingredient.

19. A method for controlling animal pests comprising allowing a compound of formula (Ia) or (Ib) according to claim 1 to act on the animal pests and/or their habitat.

20. A method for controlling animal pests comprising allowing an agrochemical formulation according to claim 17 to act on the animal pests and/or their habitat.

* * * * *